(12) United States Patent
Kaku et al.

(10) Patent No.: US 12,369,717 B2
(45) Date of Patent: Jul. 29, 2025

(54) SEAT APPLICATION MANAGEMENT DEVICE, SEAT EXPERIENCING SYSTEM, AND SEAT APPLICATION MANAGEMENT PROGRAM

(71) Applicant: TS TECH CO., LTD., Asaka (JP)

(72) Inventors: Hiroyuki Kaku, Tochigi (JP); Yosuke Higashi, Tochigi (JP)

(73) Assignee: TS TECH CO., LTD., Saitama (JP)

( * ) Notice: Subject to any disclaimer, the term of this patent is extended or adjusted under 35 U.S.C. 154(b) by 456 days.

(21) Appl. No.: 17/997,136

(22) PCT Filed: Apr. 19, 2021

(86) PCT No.: PCT/JP2021/015918
§ 371 (c)(1),
(2) Date: Oct. 26, 2022

(87) PCT Pub. No.: WO2021/220870
PCT Pub. Date: Nov. 4, 2021

(65) Prior Publication Data
US 2023/0180937 A1    Jun. 15, 2023

(30) Foreign Application Priority Data

Apr. 27, 2020  (JP) ................................ 2020-078242
Sep. 25, 2020  (JP) ................................ 2020-160776
(Continued)

(51) Int. Cl.
*A47C 7/72*      (2006.01)
*A47C 15/00*    (2006.01)
(Continued)

(52) U.S. Cl.
CPC ............ *A47C 7/727* (2018.08); *A47C 15/004* (2013.01); *A63F 13/218* (2014.09); *A63F 13/28* (2014.09);
(Continued)

(58) Field of Classification Search
CPC ..... A47C 7/727; A47C 15/004; A63F 13/218; A63F 13/28; A63F 13/79; A63F 2300/5546
See application file for complete search history.

(56) References Cited

U.S. PATENT DOCUMENTS 6,089,663 A  *  7/2000  Hill .......................... A47C 7/72
                                                       297/217.3
9,083,780 B2    7/2015  Miura et al.
(Continued)

FOREIGN PATENT DOCUMENTS

CN    109606316 A    4/2019
JP    2004229845 A    8/2004
(Continued)

OTHER PUBLICATIONS

Office Action issued for corresponding Japanese Patent Application No. 2020-078242, date of mailing: Dec. 5, 2023, 6 pages including machine translation.
(Continued)

*Primary Examiner* — Reginald A Renwick
(74) *Attorney, Agent, or Firm* — HSML P.C.

(57) ABSTRACT

A seat application management device for managing an application for offering an experience using a seat is provided. The seat application management device for managing a usage pattern of a seat provided with a sensor is configured to execute, in response to an operation of a user, an application execution process of providing an interface that allows the user to select at least one application from
(Continued)

among a plurality of applications each of which utilizes data acquired from the sensor to offer an experience using the seat to a seated occupant, and executing the selected application, and a record presentation process of retrieving and presenting an execution result of an executed application.

19 Claims, 35 Drawing Sheets

(30) Foreign Application Priority Data

Sep. 25, 2020 (JP) ................................ 2020-161143
Sep. 28, 2020 (JP) ................................ 2020-162095

(51) Int. Cl.
*A63F 13/218* (2014.01)
*A63F 13/28* (2014.01)
*A63F 13/79* (2014.01)

(52) U.S. Cl.
CPC ...... *A63F 13/79* (2014.09); *A63F 2300/5546* (2013.01)

(56) References Cited

U.S. PATENT DOCUMENTS

| | | | |
|---|---|---|---|
| 2013/0122968 A1 | 5/2013 | Miura et al. | |
| 2015/0367789 A1 | 12/2015 | Drake et al. | |
| 2021/0046391 A1* | 2/2021 | Board | A63G 31/16 |
| 2021/0188131 A1 | 6/2021 | Kaku | |
| 2021/0237617 A1 | 8/2021 | Kaku et al. | |

FOREIGN PATENT DOCUMENTS

| | | | |
|---|---|---|---|
| JP | 2011115362 | A | 6/2011 |
| JP | 2014132782 | A | 7/2014 |
| JP | 3194304 | U | 11/2014 |
| JP | 2017065504 | A | 4/2017 |
| JP | 2019077220 | A | 5/2019 |
| JP | 2019151251 | A | 9/2019 |
| JP | 2019153135 | A | 9/2019 |
| JP | 3225235 | U | 2/2020 |
| WO | 2019235462 | A1 | 12/2019 |

OTHER PUBLICATIONS

Notice of Reasons for Refusal issued for Japanese Patent Application No. 2020-078242, Dispatch date: Jun. 25, 2024, 8 pages including English machine translation.
Notice of Reasons for Refusal issued for Japanese Patent Application No. 2020-160776, Dispatch date: Jun. 25, 2024, 8 pages including English machine translation.
Notice of Reasons for Refusal issued for Japanese Patent Application No. 2020-162095, Dispatch date: Jul. 2, 2024, 4 pages including English machine translation.
International Search Report issued for International Patent Application No. PCT/JP2021/015918, Date of mailing: Jul. 13, 2021, 7 pages including English translation.
Written Opinion issued for International Patent Application No. PCT/JP2021/015918, Date of mailing: Jul. 13, 2021, 8 pages including English translation.

* cited by examiner

FIG.4

(a) USER TABLE

| USER ID | USER NAME | PASSWORD | COUNTRY | CITY | SEX | BIRTHDAY | 100m TARGET 1 | 100m TARGET 2 | ... |
|---|---|---|---|---|---|---|---|---|---|
| 23591 | user1 | ・・・・・・ | Japan | Tokyo | M | ・・・ | ○○sec.○○ | ○○rank | ・ |
| 23592 | user2 | ・・・・・・ | China | Beijing | F | ・・・ | | | ・ |
| ・ | ・ | ・ | ・ | ・ | ・ | ・ | ・ | ・ | ・ |

(b) APP EXPERIENCE TABLE

| USER ID | EXECUTION DATE & TIME | APP NAME | EVALUATION 1 | EVALUATION 2 | CALORIES BURNED | POINTS |
|---|---|---|---|---|---|---|
| 23591 | 2020-03-05-22:01 | 100m | 15"12 | | 50 | 1pt |
| 23591 | 2020-03-04-12:15 | SEATED ZEN | 85 | | 0 | 1pt |
| 23592 | 2020-03-04-13:35 | RACE | 2'01"10'91 | 03"11 | 210 | 2pt |
| ・ | ・ | ・ | ・ | ・ | ・ | ・ |

(c) USAGE HISTORY TABLE

| USER ID | EXECUTION DATE & TIME | ACTION | EXECUTING PERSON | ... |
|---|---|---|---|---|
| 23591 | 2020-03-09-14:10 | PRINT | ADMINISTRATOR | ・ |
| 23591 | 2020-03-09-14:00 | VIEW | EXPERIENCED USER | ・ |
| ・ | ・ | ・ | ・ | ・ |

FIG.10

RECORDS OF YOURSELF  PRINT —BP
—SP
—DSP

☐ RUN ←— BA

| DATE OF EXPERIENCE | CATEGORY | TIME |
|---|---|---|
| 2020 - 3 - 5 | 100m | 15"12 |
| 2020 - 2 - 6 | 200m | 35"25 |
| 2020 - 1 - 1 | 100m | 14"38 |

⋮

☐ AUTO RACE ←— BA

| DATE OF EXPERIENCE | RANK | TIME | BEST LAP TIME |
|---|---|---|---|
| 2019 - 12 - 20 | 1 | 1:45'12"11 | 03"21 |
| 2019 - 10 - 1 | 5 | 1:50'11"25 | 03"25 |

⋮

MAIN SCREEN —BM

FIG.23

| | 25R | 26R | 25L | 26L | 21R | 22R | 23R | 21L | 22L | 23L |
|---|---|---|---|---|---|---|---|---|---|---|
| FIRST ROUND | 1 | 389 | 1 | 457 | 693 | 559 | 393 | 636 | 517 | 379 |
| SECOND ROUND | 2 | 271 | 2 | 356 | 672 | 528 | 375 | 657 | 496 | 392 |
| THIRD ROUND | 1 | 280 | 2 | 364 | 674 | 521 | 365 | 650 | 498 | 391 |
| AVERAGE | 1 | 313 | 2 | 392 | 680 | 536 | 378 | 648 | 504 | 387 |
| AVERAGE +2σ | 3 | 421 | 3 | 485 | 699 | 570 | 401 | 666 | 523 | 400 |
| AVERAGE −2σ | 0 | 206 | 0 | 300 | 660 | 502 | 354 | 630 | 484 | 375 |

FIG.24

|  | USER GOT SEATED ON THE SEAT | | | | |
|---|---|---|---|---|---|
|  | A | B | C | D | E |
| THE NUMBER OF SENSORS OF WHICH MEASUREMENT VALUES FALL WITHIN SCREENING RANGE FOR USER A | 10 | 8 | 6 | 4 | 5 |
| THE NUMBER OF SENSORS OF WHICH MEASUREMENT VALUES FALL WITHIN SCREENING RANGE FOR USER B | 7 | 10 | 5 | 3 | 4 |
| THE NUMBER OF SENSORS OF WHICH MEASUREMENT VALUES FALL WITHIN SCREENING RANGE FOR USER C | 6 | 5 | 10 | 2 | 3 |
| THE NUMBER OF SENSORS OF WHICH MEASUREMENT VALUES FALL WITHIN SCREENING RANGE FOR USER D | 3 | 1 | 2 | 10 | 6 |
| THE NUMBER OF SENSORS OF WHICH MEASUREMENT VALUES FALL WITHIN SCREENING RANGE FOR USER E | 6 | 6 | 3 | 2 | 10 |

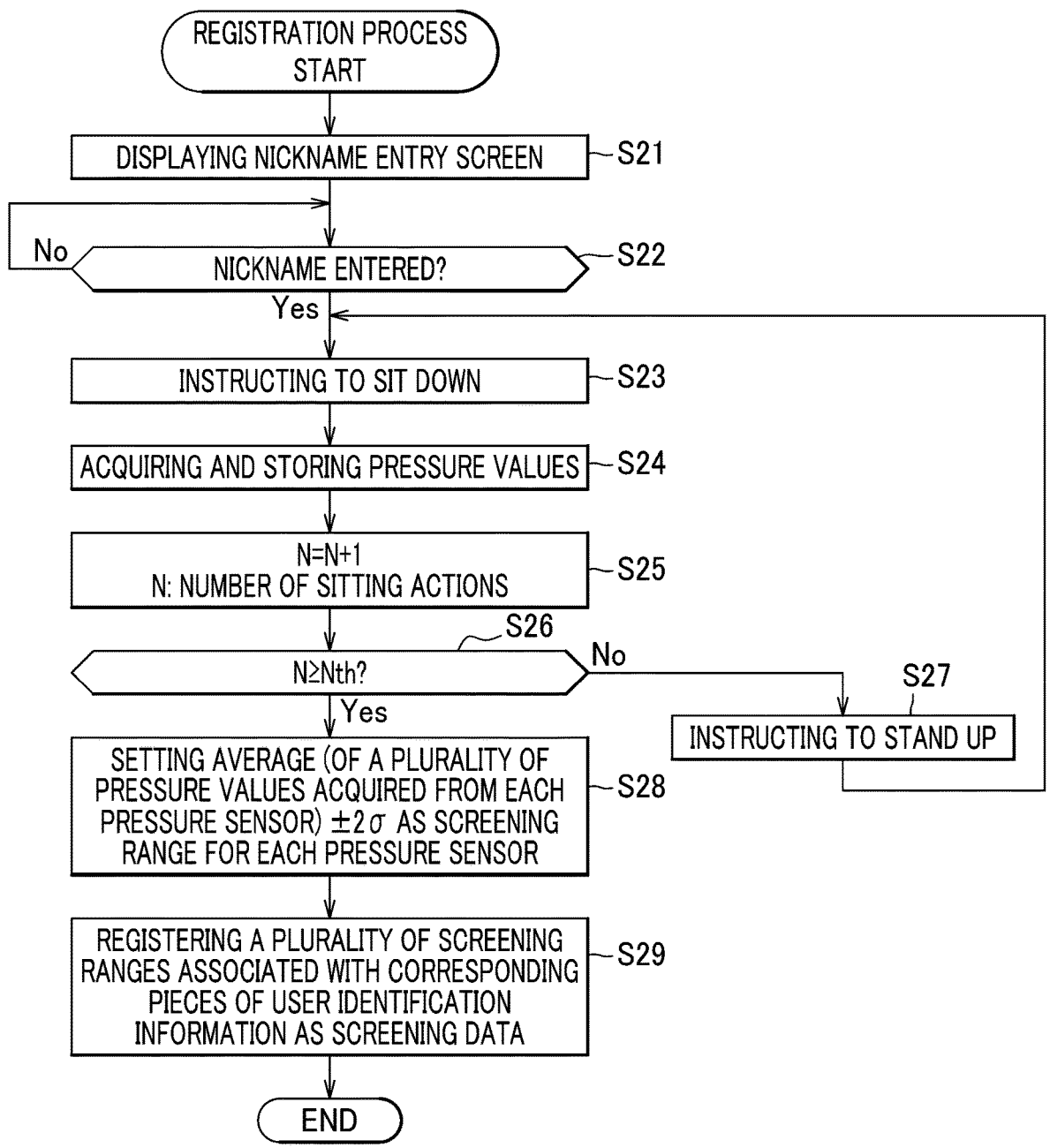

FIG.27
(a)
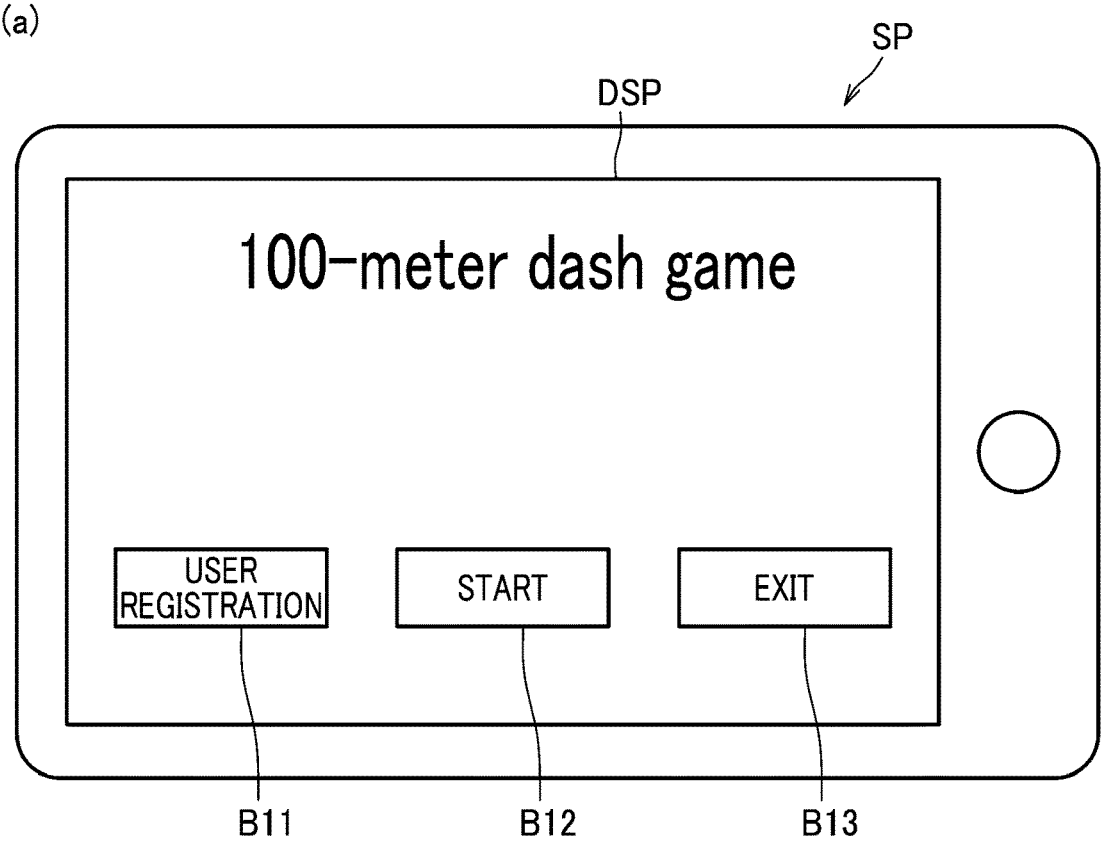
(b)
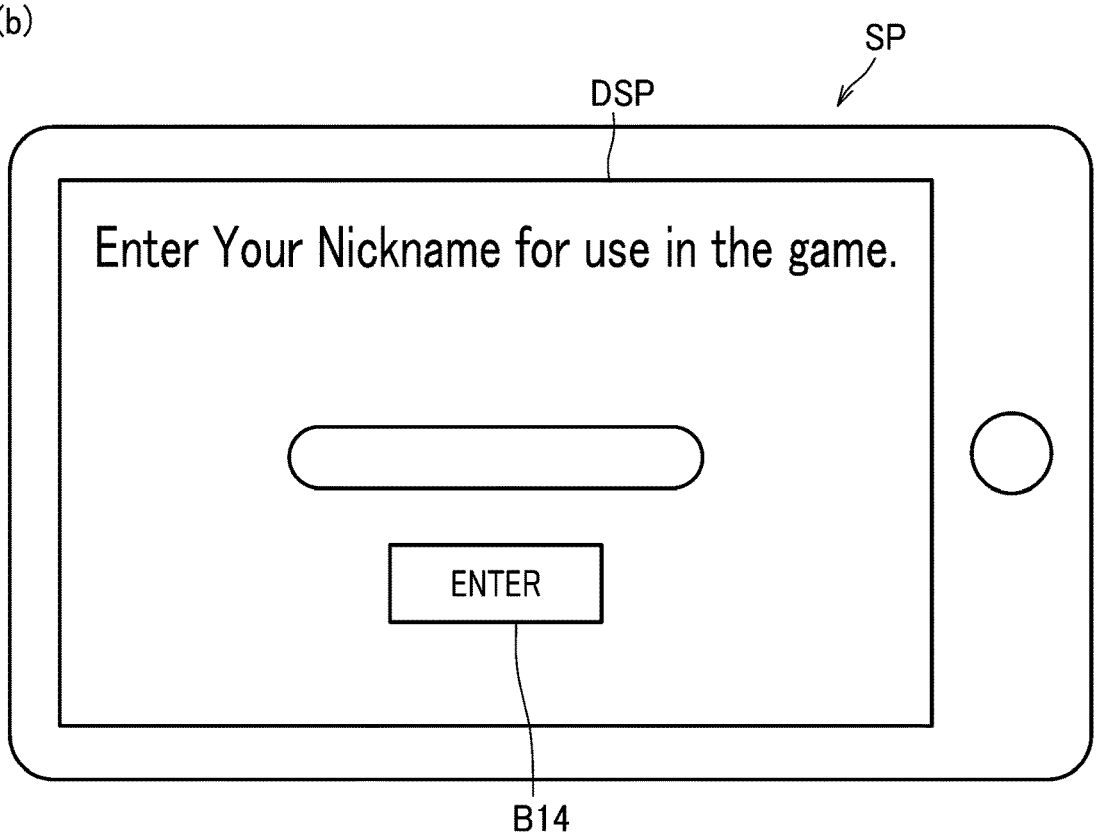

FIG.28
(a)
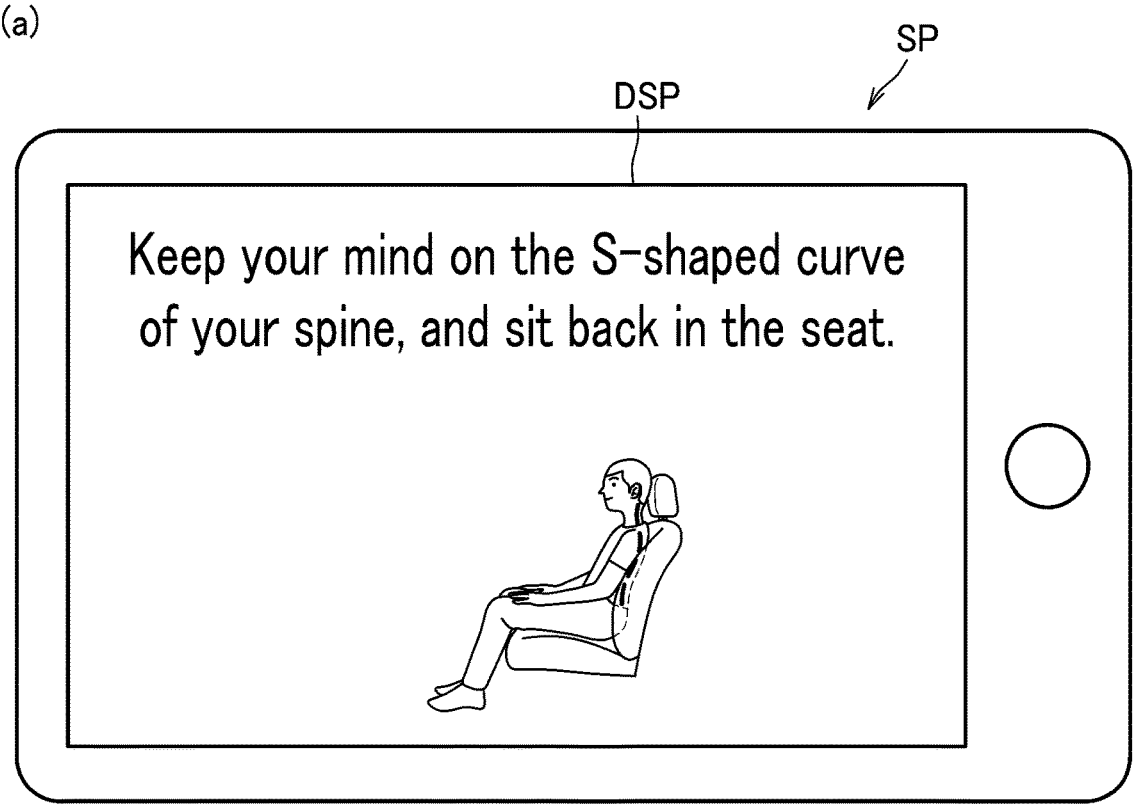
(b)
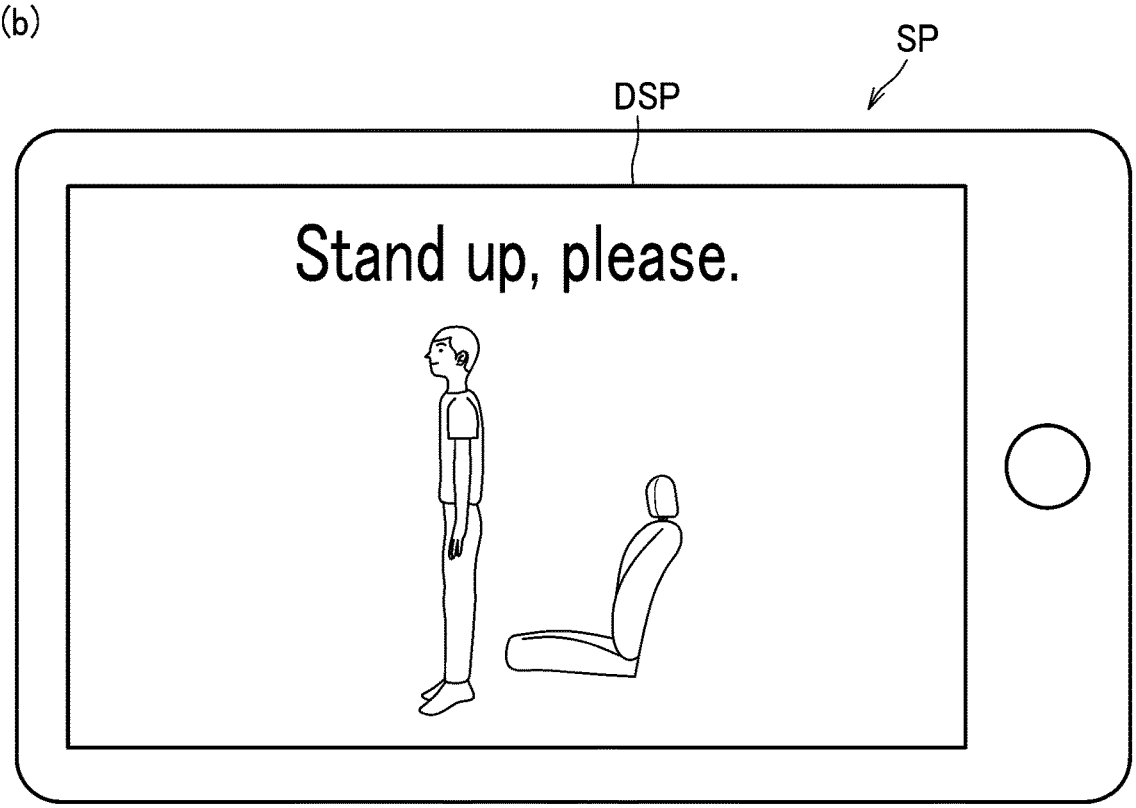

FIG.34
(a)
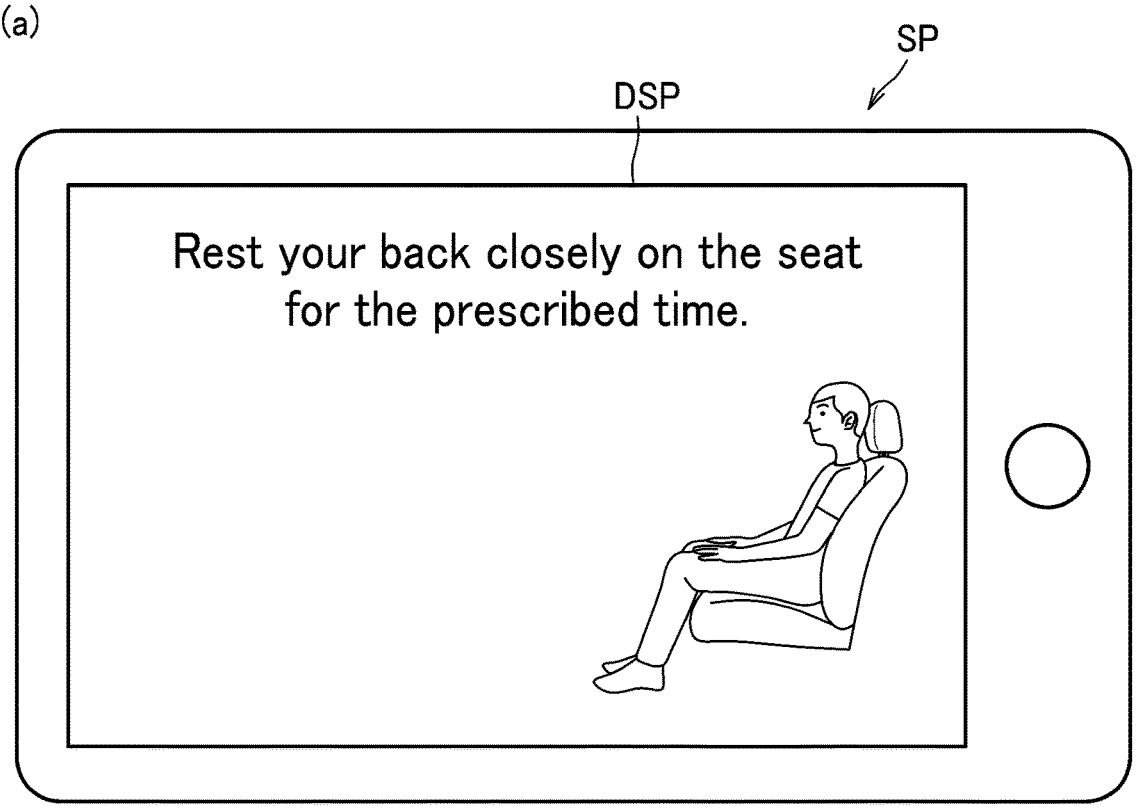
(b)
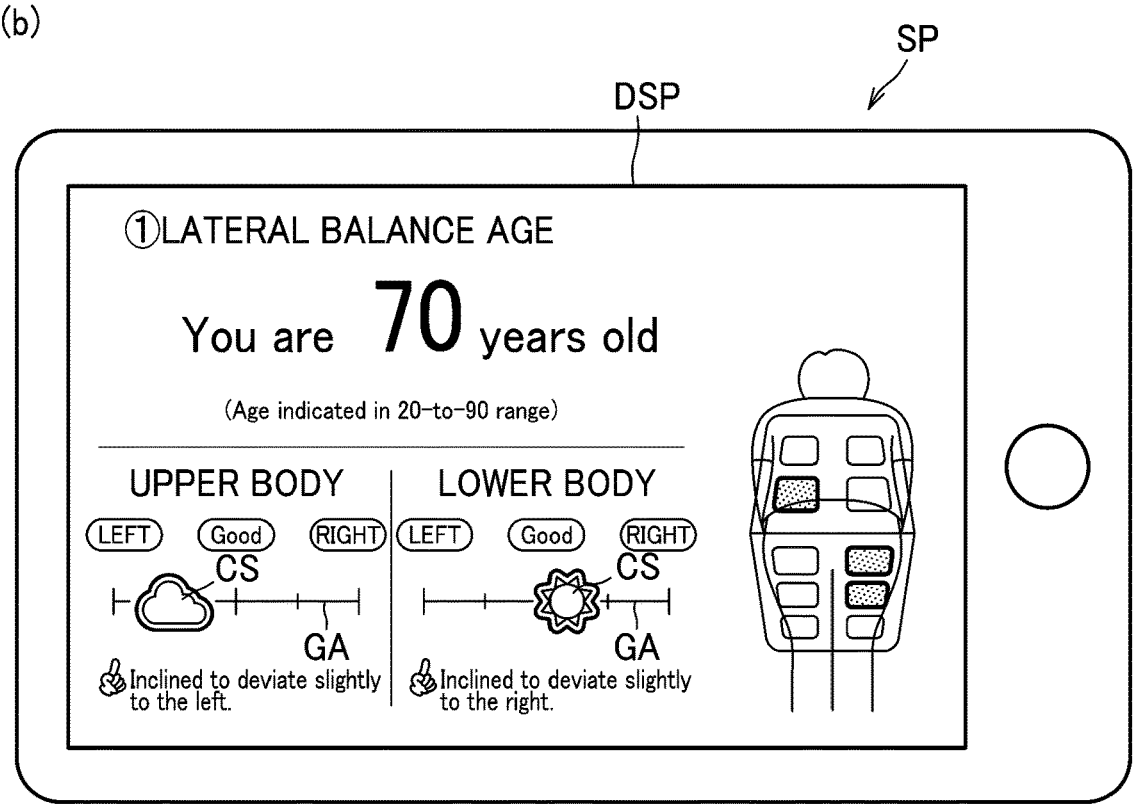

FIG.35
(a)
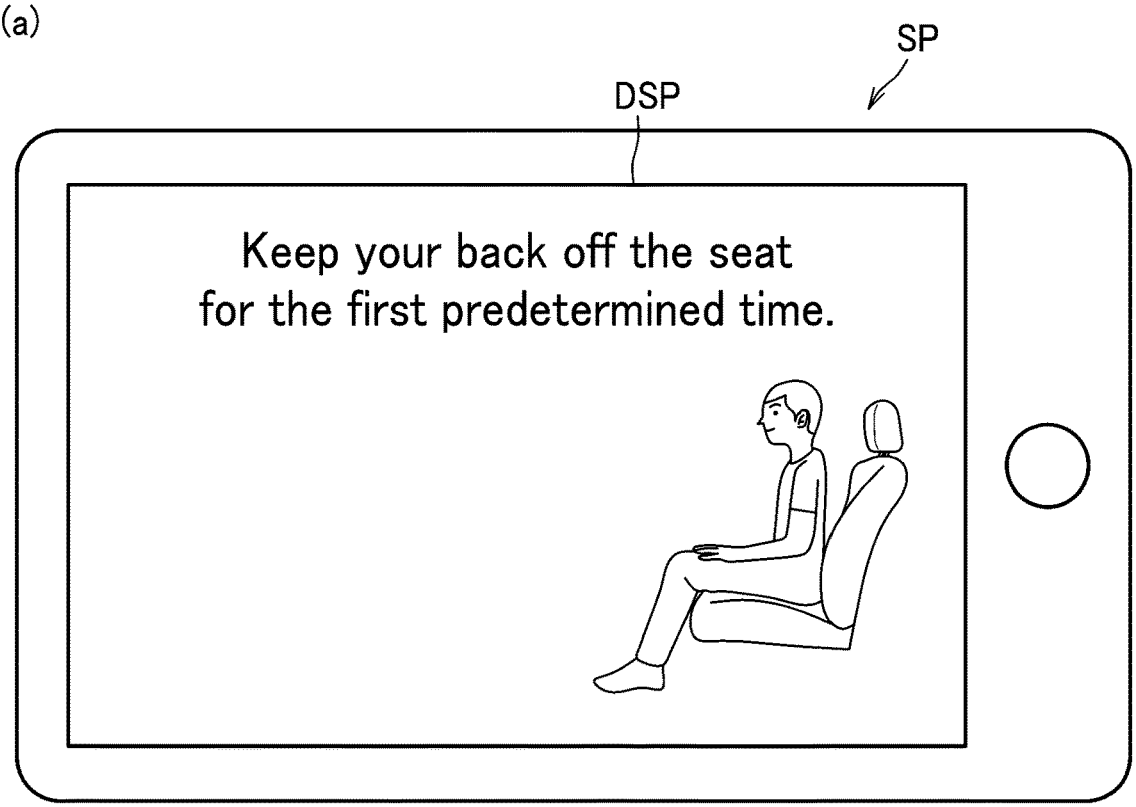
(b)
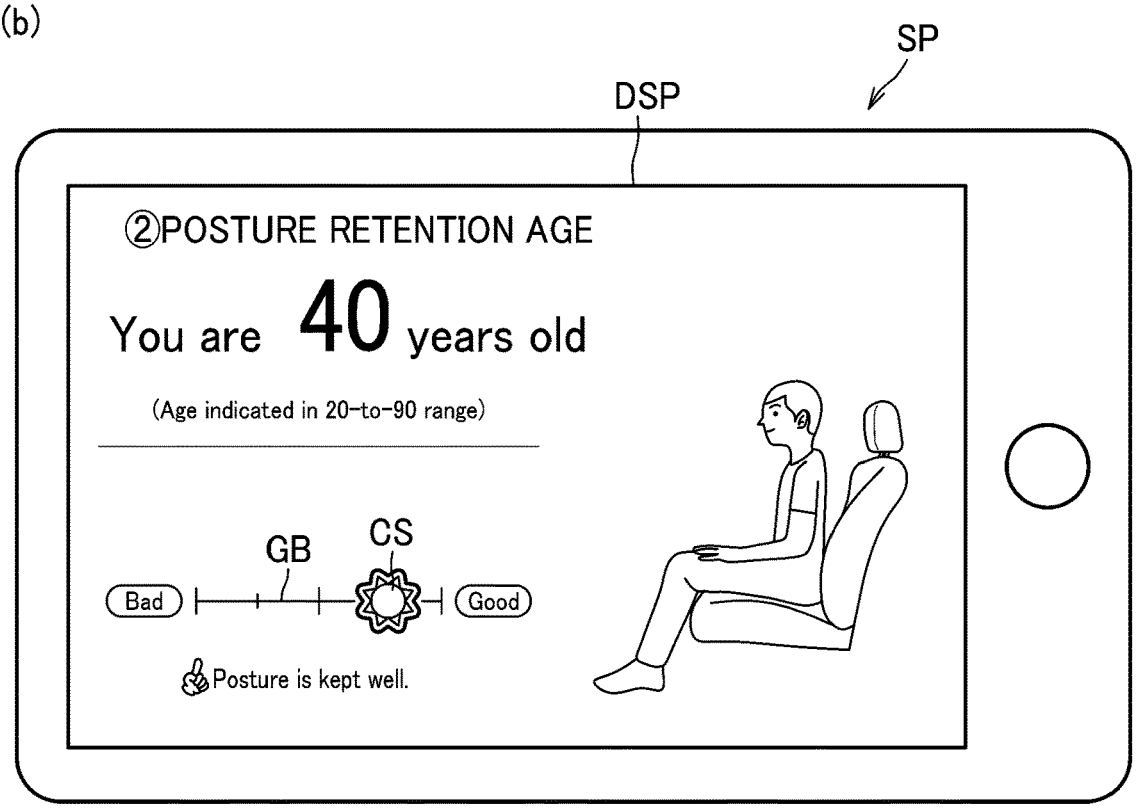

FIG.36
(a)
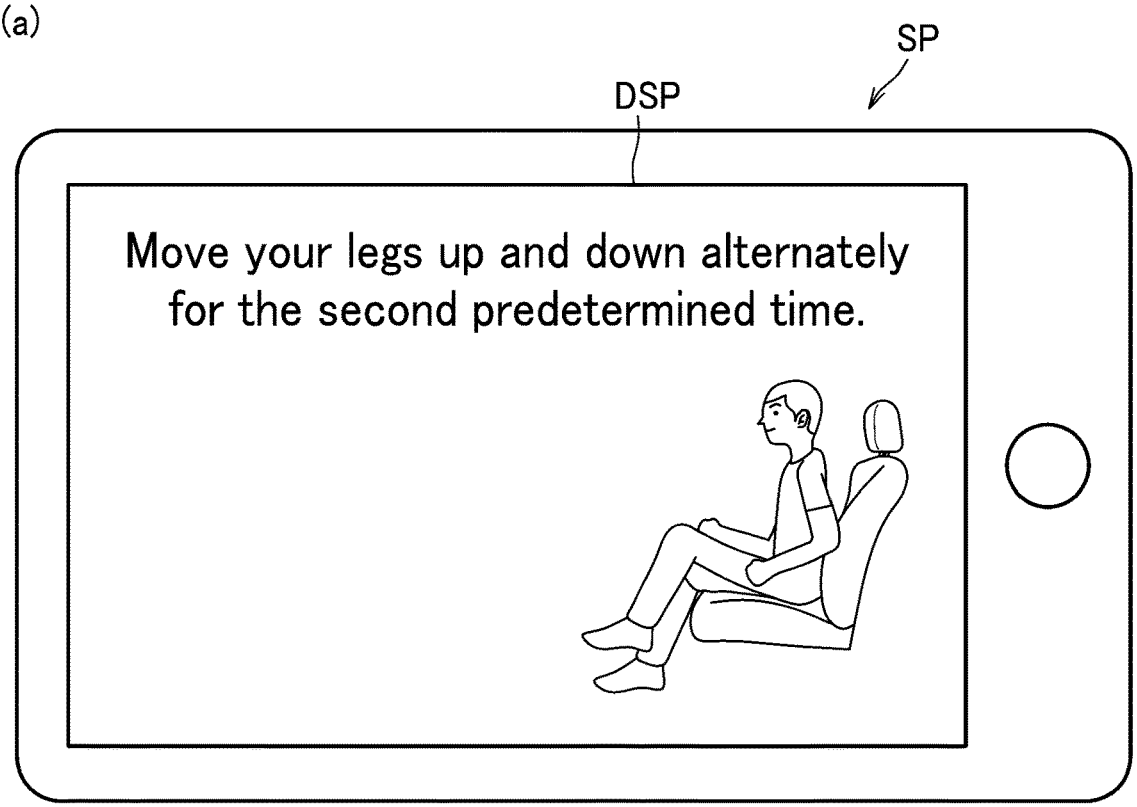
(b)
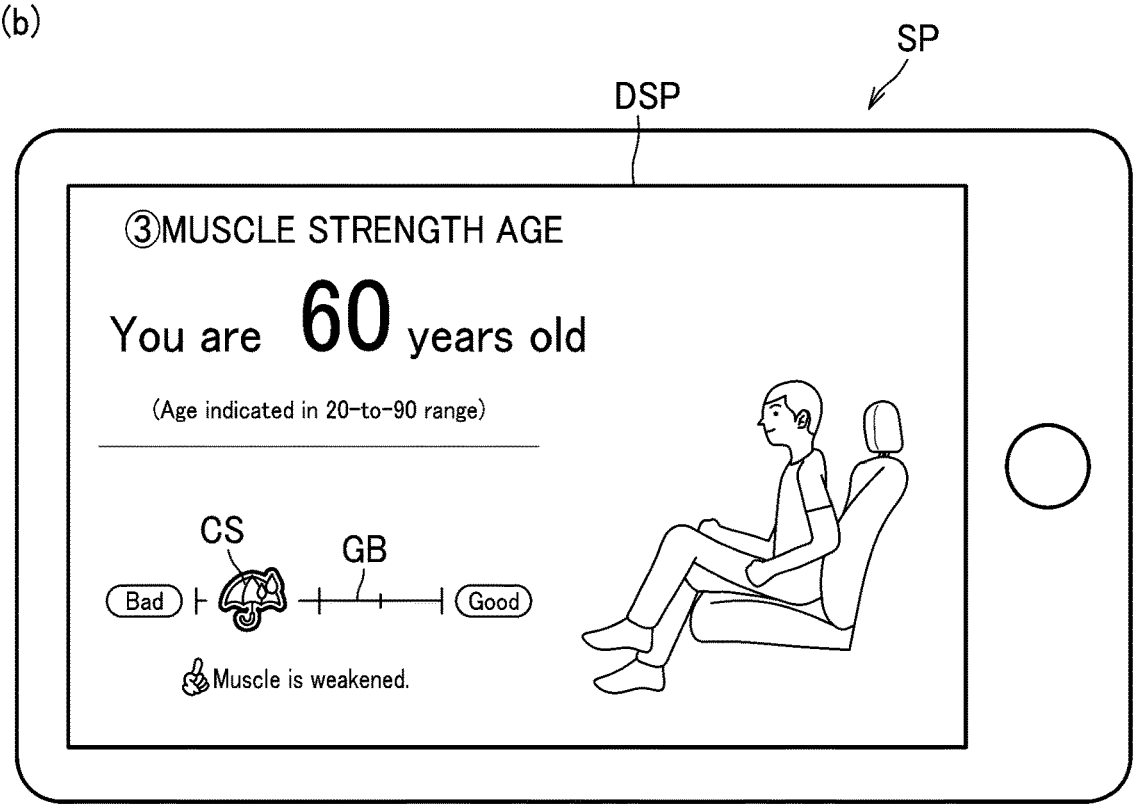

SEAT APPLICATION MANAGEMENT DEVICE, SEAT EXPERIENCING SYSTEM, AND SEAT APPLICATION MANAGEMENT PROGRAM

TECHNICAL FIELD

This disclosure relates to a seat application management device, a seat experiencing system, and a seat application management program.

BACKGROUND ART

As a device for offering an experience using a seat having sensors, a device for experiencing a proper seating posture (Patent Document 1), a device for experiencing a foot-lift exercise (Patent Document 2), and a device for experiencing a 100-meter dash game (Patent Document 3) are known in the art.

A system provided with a sensor for detecting whether or not a person is seated on a seat of a chair, for measuring time using the sensor connected to a time-measuring device is known in the art (Patent Document 4). In this technical scheme, the sensor detects a separate state of a person having risen apart from the chair, then outputs a detection signal in response to which the time-measuring device starts measuring time, and detects a sitting state of a person seated on the chair, then outputs a detection signal in response to which the time-measuring device stops measuring time, so that the elapsed time is measured.

A car seat with a plurality of pressure sensors arranged on a seat to detect a seating posture of an occupant is known in the art (Patent Document 5).

CITATION LIST

Patent Literature

Patent Document 1: JP 2019-077220 A
Patent Document 2: JP 2019-151251 A
Patent Document 3: JP 2019-153135 A
Patent Document 4: JP2011-115362 A
Patent Document 5: JP 2017-065504 A

SUMMARY OF INVENTION

When a plurality of applications for experiences using a seat are provided, in-seat experience may be enjoyed through each of those applications, but such individual experience alone would possibly not be pieced together, and the state of experience could not be grasped as a whole. From this point of view, it would be desirable to manage applications for offering experiences using a seat.

The system disclosed in Patent Document 4 uses a single sensor to detect whether or not there is a person seated, and thus could not nicely discriminate between the seated and standing states. It would thus be desirable that, in a seat experiencing system comprising a seat body on which a person is to be seated and a sensor for detecting the person seated on the seat body, the seated and standing states be discriminately detected with precision. It would also be desirable to measure time with precision.

The car seat disclosed in Patent Document 5 merely presenting the results of evaluation made on the posture of a seated driver would not make the seated person very well motivated to use its features, of which full exploitation would thus be an issue to be addressed.

The inventors of this application are contemplating causing applications such as games to be executed by using a seat having a sensor. The inventors of this application are also contemplating providing a seat installed, for example, in a lounge of nursing-care facilities or the like, for use by any one of unspecific users. Furthermore, the inventors of this application are contemplating providing a game using information identifying a user seated on a seat for the user to play a game using the seat. To this end, for example, a pull-down menu may be provided on a screen, which requests a user to select his/her user name, at the start of the game; however, if a long list of an increased number of the users appear therein, the operation of selecting his/her own user name would disadvantageously become burdensome to the user. In this respect, the inventors of this application are contemplating, for the purpose of creating a new value of a seat with a seat experiencing system comprising a seat including a sensor, means for making it easier for a user seated on the seat to select his/her own user identification information.

Furthermore, the inventors of this application are contemplating, for the purpose of creating a new value of a seat with a seat experiencing system comprising a seat including a sensor, determining a sitting posture age corresponding to a posture or a motion of a user seated on the seat.

A seat application management device for managing a usage pattern of a seat provided with a sensor is proposed, which seat application management device is configured to execute, in response to an operation of a user: an application execution process of providing an interface that allows the user to select at least one application from among a plurality of applications each of which utilizes data acquired from the sensor to offer an experience using the seat to a seated occupant, and executing the selected application; and a record presentation process of retrieving and presenting an execution result of an executed application.

With this seat application management device, options of selectable applications can be offered for execution, and thus the experiences using the seat can be enjoyed with ease. Furthermore, the execution result of the executed application can be presented, and thus user's own in-seat experiences can be pieced together, so that the state of the experiences can be grasped as a whole.

The seat application management device may be capable of communicating with a server, and the record presentation process may comprise retrieving, from the server, execution results of applications executed by the user and by another user.

With this configuration, the user can look into the other user's execution result(s) as well as his/her own execution result, and thus can compare his/her own execution result with the other user's execution result; through such comparison, and/or otherwise, the user can be motivated into the in-seat experience.

In the seat application management device, the record presentation process may comprise presenting a record of the user and a record of the another user, arranged in a ranking list.

With this configuration, the record of the user and the record of the other user(s) can be viewed in the ranking list, so that the user can be more motivated into the in-seat experience. It is to be understood that depending on the contents of ranking of records, only the user's own records may be presented, or only the another user's records may be presented.

The sensor may comprise a plurality of pressure sensors.

The execution result may comprise a usage history of the plurality of applications. The record presentation process may comprise presenting the usage history of the plurality of applications associated with a specific user.

With this configuration, the usage history of the plurality of applications associated with a specific user can be viewed in to-to; therefore, the specific user's in-seat experience can be pieced together and grasped as a whole.

The application may comprise a game using the seat. Moreover, in this configuration, the execution result may comprise a game score.

The execution result may comprise at least one of pieces of data selected from: an amount of calories burned, an application execution date, an application execution time, the number of times of execution of the application, an application execution place, and an application title.

A seat experiencing system comprising a seat provided with as sensor, and a seat application management device for managing a usage pattern of the seat is proposed. In this seat experiencing system, the seat application management device is configured to execute, in response to an operation of a user: an application execution process of providing an interface that allows the user to select at least one application from among a plurality of applications each of which utilizes data acquired from the sensor to offer an experience using the seat to a seated occupant, and executing the selected application; and a record presentation process of retrieving and presenting an execution result of an executed application.

Further proposed is a seat application management program for managing a usage pattern of a seat provided with a sensor, which seat application management program is configured to cause a computer to execute, in response to an operation of a user: an application execution process of providing an interface that allows the user to select at least one application from among a plurality of applications each of which utilizes data acquired from the sensor to offer an experience using the seat to a seated occupant, and executing the selected application; and a record presentation process of retrieving and presenting an execution result of an executed application.

Further proposed is a seat experiencing system comprising a seat body on which a person is to be seated, a plurality of sensors for detecting a person seated on the seat body, the plurality of sensors including a first sensor and a second sensor located in a position different from a position in which the first sensor is located, and a seating determination unit configured to make a determination, based on detection results of the sensors, as to whether or not a person has got seated on the seat body, in such a manner that: the seating determination unit determines that a person has got seated on the seat body, on condition that the person seated on the seat body has been detected by the first sensor and the person seated on the seat body has been detected by the second sensor, and the seating determination unit determines that a person has risen from the seat body, on condition that the person seated on the seat body has become undetected by the first sensor and the person seated on the seat body has become undetected by the second sensor.

With this configuration, in which the plurality of sensors are used to detect sit-down and rise-up motions, the sit-down and rise-up motions can be detected precisely.

The seat experiencing system described above may be configured such that: the first sensor and the second sensor are pressure sensors, and the seating determination unit is configured: to determine that a person has got seated on the seat body, on condition that a measurement value from the first sensor has become equal to or greater than a first sitting threshold and a measurement value from the second sensor has become equal to or greater than a second sitting threshold, and to determine that a person has risen from the seat body, on condition that the measurement value from the first sensor has become equal to or smaller than a first rising threshold smaller than the first sitting threshold and the measurement value from the second sensor has become equal to or smaller than a second rising threshold smaller than the second sitting threshold.

The seat experiencing system described above may be configured such that the seat body comprises a seat bottom on which a person is to be seated, and the first sensor is located in a position corresponding to buttocks of a person to be seated on the seat bottom, and the second sensor is located in a position corresponding to thighs of a person to be seated on the seat bottom.

With this configuration, the sensors are located in positions on which high pressure is exerted when a person is seated on the seat body, and thus the sit-down and rise-up motions can be detected more precisely.

The seat experiencing system described above may be configured such that the first sensor comprises at least one right first sensor and at least one left first sensor, and the second sensor comprises at least one right second sensor and at least one left second sensor.

With this configuration, arrangement of the increased number of sensors used to detect sit-down and rise-up motions can make it possible to detect the sit-down and rise-up motions more precisely.

The seat experiencing system described above may be configured to comprise a time-measuring unit configured to measure time based on a result of the determination made by the seating determination unit, wherein the time-measuring unit starts measurement of time at a time when the seating determination unit has determined that a person has risen from the seat body, ends the measurement of time at a time when the seating determination unit has determined that a person has got seated on the seat body, and determines by calculation an elapsed time that has elapsed from the time of starting the measurement of time to the time of ending the measurement of time.

With this configuration, the sit-down and rise-up motions can be detected precisely, and a period of time that has elapsed from a time at which a person has risen from the seat body to a time at which a person has got seated on the seat body can be measured precisely.

The seat experiencing system described above may be configured to comprise a time-measuring unit configured to measure time based on a result of the determination made by the seating determination unit, wherein the time-measuring unit starts measurement of time at a time when the seating determination unit has determined that a person has got seated on the seat body, and executes a predetermined operation for prompting the person seated on the seat body to rise from the seat body after a lapse of a predetermined time period from the time of starting the measurement of time, and stops the predetermined operation at a time when the seating determination unit has determined that the person has risen from the seat body.

With this configuration, the sit-down and rise-up motions can be detected more precisely, and a period of time that has elapsed from a time at which a person has got seated on the seat body can be measured precisely. Accordingly, the predetermined operation can be executed with precise timing. The person seated on the seat body is thus prompted by the executed predetermined operation to rise up, and can be prevented from remaining seated over an extended period of time.

In the seat experiencing system described above, the predetermined operation comprises an operation of producing a predetermined sound, which may for example include playing music.

The seat experiencing system described above may be configured to comprise a time-measuring unit configured to measure time based on a result of the determination made by the seating determination unit, such that the time-measuring unit starts measurement of time at a time when the seating determination unit has determined that a person has got seated on the seat body, ends the measurement of time at a time when the seating determination unit has determined that a person has risen from the seat body, and determines by calculation an elapsed time that has elapsed from the time of starting the measurement of time to the time of ending the measurement of time.

With this configuration, the sit-down and rise-up motions can be detected more precisely, and a period of time that has elapsed from a time at which a person has got seated on the seat body to a time at which a person has risen from the seat body can be measured precisely.

The seat experiencing system described above may be configured such that the seating determination unit determines that a person has risen from the seat body when a first time period has elapsed from a time at which the person seated on the seat body has become undetected by the first sensor and the person seated on the seat body has become undetected by the second sensor.

With this configuration, a determination that a person has risen from the seat body is not made until the person has assumed a complete standing posture; therefore, the rise-up motion can be detected more precisely.

The seat experiencing system described above may be configured such that the seating determination unit determines that a person has got seated on the seat body when a second time period has elapsed from a time at which the person seated on the seat body has been detected by the first sensor and the person seated on the seat body has been detected by the second sensor.

With this configuration, a determination that a person has got seated on the seat body is not made until the person has assumed a complete sitting posture; therefore, the sit-down motion can be detected more precisely.

A seat experiencing system comprising: a seat including a seat body and a sensor configured to acquire a numeric value for use in detection of a physical state of a user on the seat body; a controller configured to acquire the numeric value from the sensor; and a terminal comprising a screen is proposed.

The controller is capable of displaying, on the screen, a plurality of pieces of user identification information corresponding to a plurality of users, the controller being configured to store, as a screening range, a numeric value range extended with predetermined margins allowed for the numeric value acquired from the sensor when a user is on the seat body, the screening range being associated with a piece of user identification information of the user, determine whether a criterion, which is satisfied if the numeric value acquired from the sensor when a user is on the seat body falls within the screening range, is satisfied for each of the pieces of user identification information; and display, on the screen, the pieces of user identification information in such a manner that a piece of user identification information for which the criterion is satisfied takes precedence over a piece of user identification information for which the criterion is not satisfied.

With this configuration, when a specific user is on the seat body, a numeric value acquired from the sensor is more likely to fall within the screening range for the specific user, and thus the piece of user identification information of the specific user is given precedence over the other pieces of user identification information when the pieces of user identification information are displayed on the screen. Accordingly, the user on the seat body can select his/her own user identification information with increased ease.

The sensor may comprise a plurality of sensors, and the controller may be configured to: store, as a plurality of screening ranges, numeric value ranges each extended with predetermined margins allowed for the numeric value acquired from each of the sensors when a user is on the seat body, the screening ranges being associated with a piece of user identification information of the user, determine whether the criterion is satisfied for each of the plurality of sensors when the user is on the seat body, associate a satisfied criterion number that is the number of satisfied criteria with a piece of user identification information of the user, and display, on the screen, the pieces of user identification information in descending order of satisfied criterion numbers.

With this configuration, a plurality of numeric values are compared with a plurality of screening ranges, so that the user on the seat body can be discriminated from the other users more precisely.

The sensor may be a pressure sensor configured to acquire, as the numeric value, a value of pressure from the user.

The controller may be capable of displaying a pull-down menu in which the plurality of pieces of user identification information are listed downward on the screen, and the controller may be configured to display a piece of user identification information that takes precedence over another piece of user identification information, at a location higher than the another piece of user identification information.

When the controller stores the screening range, the controller may acquire the numeric value from the sensor on a plurality of occasions, and set the screening range by the formula:

$$\mu \pm A \times \sigma$$

where $\mu$ is an average of numeric values acquired on the plurality of occasions, $\sigma$ is a standard deviation of the numeric values acquired on the plurality of occasions, and A is an arbitrary number.

When a piece of user identification information displayed on the screen is selected by a user, the controller may reset a screening range corresponding to the selected piece of user identification information, based on a numeric value acquired this time from the sensor.

With this configuration, each time the piece of user identification information is selected by the user, the user's own screening range is reset based on the numeric value acquired this time; therefore, the screening range can be set more precisely.

A seat experiencing system comprising: a seat including a seat body and a sensor configured to acquire information for detecting a posture or a motion of a user on the seat body; and a controller configured to acquire the information from the sensor is proposed. The controller is configured to: compute at least one of evaluation values which comprise a first evaluation value corresponding to leftward or rightward postural deviation of an upper body or a lower body of the user on the seat body, a second evaluation value corresponding to retention of a posture of the user for a first predetermined time period, and a third evaluation value corresponding to an amount of motion of the user for a second predetermined time period, based on the information acquired from the sensor; and determine a sitting posture age corresponding to the posture or the motion of the user based on the evaluation values.

With this configuration, the sitting posture age corresponding to the posture or the motion of the user seated on the seat can be determined based on information acquired from the sensor.

The controller may be configured to determine the sitting posture age based on at least two evaluation values selected from the first evaluation value, the second evaluation value, and the third evaluation value.

With this configuration, the sitting posture age can be determined more precisely.

The controller may be configured to determine the sitting posture age based on the first evaluation value, the second evaluation value and the third evaluation value.

With this configuration, the sitting posture age can be determined more precisely.

The sensor may be a pressure sensor configured to acquire a value of pressure from a user, and the controller may be configured to compute the first evaluation value, the second evaluation value, and the third evaluation value, based on the value of pressure.

With this configuration, each of the evaluation values can be computed precisely based on the value of pressure from the user.

The pressure sensor may comprises a left sensor located at a left part of the seat body, and a right sensor located at a right part of the seat body, and the controller may be configured such that the greater a magnitude of a difference between a pressure value from the left sensor and a pressure value from the right sensor, the greater the sitting posture age is made.

It is to be understood that the older a person is, the more the leftward or rightward postural deviation of his/her upper or lower body is observed when he/she is seated on the seat body due to pelvic torsion or the like. Therefore, the sitting posture age is made greater in accordance with the magnitude of the difference between the pressure value from the left sensor and the pressure value from the right sensor, so that the sitting posture age can be determined properly in such a way that a user having an upper or lower body deviated leftward or rightward more is older in age.

The controller may be configured such that the greater a range of variation of the value of pressure for the first predetermined time period, the greater the sitting posture age is made.

It is to be understood that the older a person is, the more difficult it is for that person to retain his/her posture, and the more his/her body sways, when he/she is seated on the seat body. Therefore, the sitting posture age is made greater in accordance with the extent of variation of the value of pressure, so that the sitting posture age can be determined properly in such a way that a person who is more difficult to retain his/her posture for the first predetermined time period is older in age.

The controller may be configured to compute the amount of the motion for the second predetermined time period based on the value of pressure, and configured such that the greater the amount of the motion, the less the sitting posture age is made.

It is to be understood that the younger a person is, the larger the amount of the motion is made by the person on the seat. Therefore, the sitting posture age is made smaller in accordance with the amount of the motion, so that the sitting posture age can be determined properly in such a way that a person who makes a motion of a greater amount is younger in age.

BRIEF DESCRIPTION OF DRAWINGS

FIG. 4 shows one example of tables stored in a database of the server, which include (a) a user table, (b) an application experience table, and (c) a usage history table

FIG. 10 is one example of a screen of records of yourself.

FIG. 23 is a diagram showing a plurality of screening ranges as computed based on values of pressure acquired from a plurality of pressure sensors.

FIG. 24 is a diagram showing a relationship between users seated on a seat and the number of pressure sensors of which measurement values fall within the screening range of each user.

FIG. 25 is a flowchart showing a registration process.

FIG. 27 includes (a) a diagram showing a start image for a 100-meter dash game, and (b) a diagram showing a nickname entry image.

FIG. 28 includes (a) a diagram showing an image for prompting a user to sit down, and (b) a diagram showing an image for prompting a user to rise up.

FIG. 34 includes (a) a diagram showing a first instruction screen, and (b) a diagram showing a screen for displaying a lateral balance age.

FIG. 35 includes (a) a diagram showing a second instruction screen, and (b) a diagram showing a screen for displaying a posture retention age.

FIG. 36 includes (a) a diagram showing a third instruction screen, and (b) a diagram showing a screen for displaying a muscle strength age.

DESCRIPTION OF EMBODIMENTS

Next, a description will be given of a seat application management device according to a first embodiment.

Figure 1:
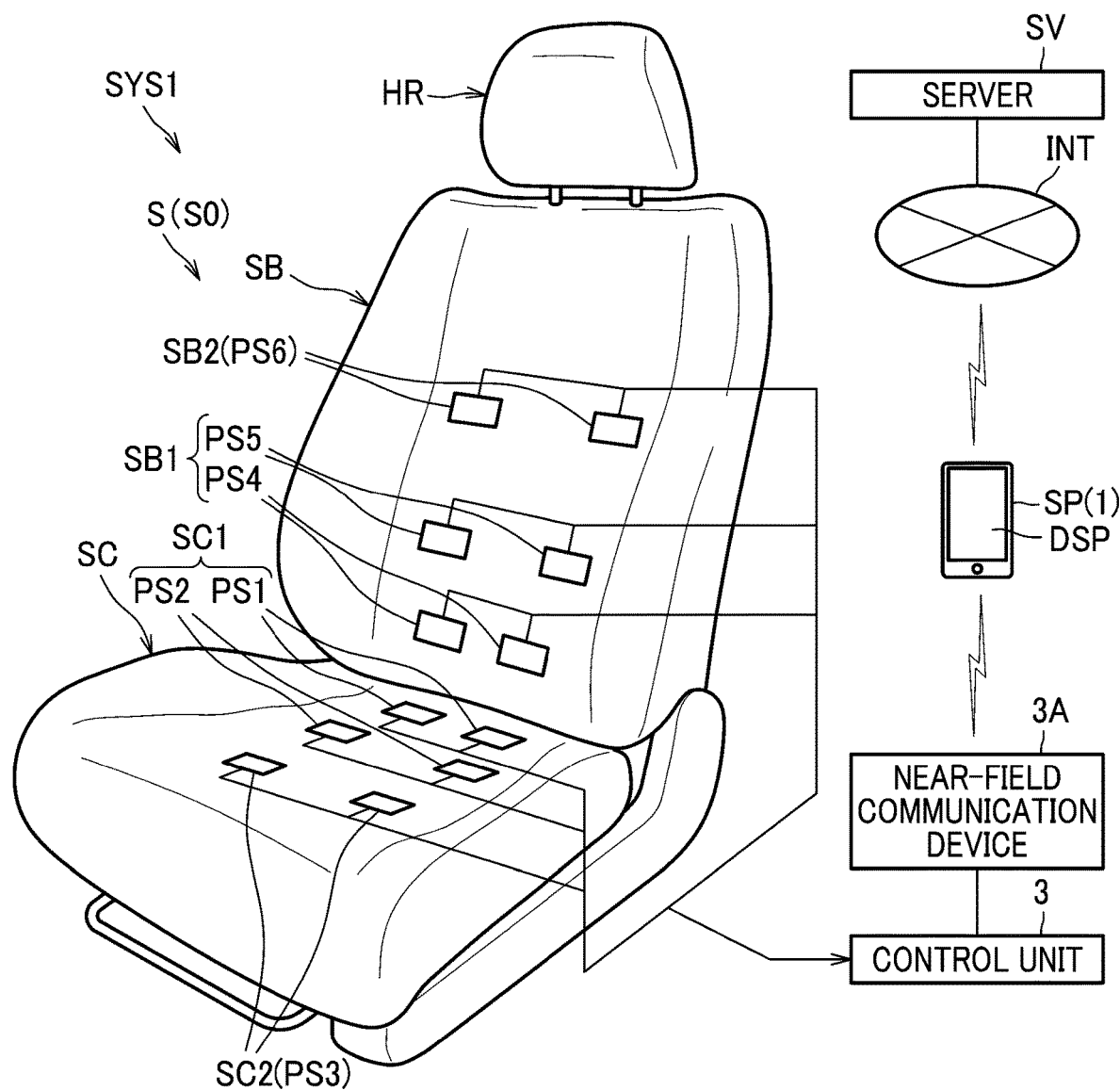
FIG. 1 is a diagram showing a general setup of a system using a vehicle seat according to a first embodiment.

As shown in FIG. 1, a seat experiencing system SYS1 is configured to comprise a seat S, a smartphone SP for implementing a seat application management device 1, and a server SV. The seat S includes a seat body S0 and a control unit 3.

The seat body S0 includes a seat cushion SC, a seat back SB, and a headrest HR. The seat cushion SC and the seat back SB have an outer covering under which a plurality of pressure sensors PS1 to PS6 are provided. The pressure sensors PS1 to PS6 are sensors that acquire measurement values for identifying a motion or the like of an occupant seated on the seat body S0. The pressure sensors PS1 to PS6 are so arranged as to be capable of detecting a state of a seat surface facing an occupant seated on the seat body S0, to acquire values of pressure from the occupant seated on the seat body S0. The control unit 3 is connected to the pressure sensors PS1 to PS6 and thereby capable of acquiring pressure values from the pressure sensors PS1 to PS6.

The pressure sensors PS1 to PS6 are provided in pairs, i.e., each located left and right, symmetric with respect to a laterally central position of the seat S.

Specifically, in the seat cushion SC, the pressure sensors PS1 to PS3 are provided. The pressure sensors PS1 and PS2 are located in positions, corresponding to the buttocks of the occupant, of the seat cushion SC. The pressure sensors PS1 and PS2 constitute a first cushion sensor SC1 that measures pressure from the buttocks of the occupant. The pressure sensors PS2 are located a little frontward of the pressure sensors PS1. It is to be understood that the first cushion sensor SC1 may comprise only one of the pressure sensors PS1 and the pressure sensors PS2.

The pressure sensors PS3 are located under the thighs of an occupant. The pressure sensors PS3 constitute a second cushion sensor SC2 that determines values of pressure from the thighs of the occupant. The pressure sensors PS3 are located frontward of and distanced far from the pressure sensors PS1 and the pressure sensors PS2.

In the seat back SB, the pressure sensors PS4 to PS6 are provided. The pressure sensors PS4 are provided in positions corresponding to the back of the waist of the occupant. The pressure sensors PS5 are located a little above the pressure sensors PS4. Both of the pressure sensors PS4 and the pressure sensors PS5 constitute a first back sensor SB1 that measures pressure from the waist of the occupant. It is to be understood that the first back sensor SB1 may comprise only one of the pressure sensors PS4 and the pressure sensors PS5.

The pressure sensors PS6 are located above and distanced far from the pressure sensors PS4 and the pressure sensors PS5. The pressure sensors PS6 are located in positions corresponding to the upper region of the back of an occupant. The pressure sensors PS6 constitute a second back sensor SB2 that determines values of pressure from the upper region of the back of the occupant.

The control unit 3 is provided with a near-field communication device 3A, and is capable of communicating with the smartphone SP. The control unit 3 is configured to transmit pressure values acquired from the plurality of pressure sensors PS1 to PS6 to the smartphone SP.

The smartphone SP is connected to the Internet INT via a wireless communication channel such as public mobile-phone lines. The smartphone SP comprises a display DSP capable of showing characters and images. The smartphone SP further comprises a speaker (not shown) and is thereby configured to be capable of transmitting information to a user by sound and/or voice.

The server SV is connected to the Internet INT. The smartphone SP is capable of communicating with the server SV via the Internet INT. The server SV may be a local server located in a common network, or may be a cloud server located in a different network.

The smartphone SP includes a CPU, a ROM, a RAM, a rewritable nonvolatile memory, etc. (not shown), and functions as a seat application management device 1 (hereinafter also referred to simply as "management device 1") by executing a seat application management program PG1 stored in advance. The management device 1 is a device for managing a usage pattern of a seat S provided with pressure sensors PS1 to PS6. The management device 1 executes an application execution process and a record presentation process in response to an operation of a user.

The application execution process is a process of providing, by displaying on the display DSP, an interface that allows a user to select at least one application from among a plurality of applications. Herein, the application(s) refers to an application(s) that utilizes data acquired from the pressure sensors PS1 to PS6 to offer an experience using the seat S to an occupant seated thereon. The application(s) selected through the interface is executed in this process.

To provide the interface, the management device 1 generates image data using data stored in the smartphone SP for application(s) that offers an experience using the seat S, and displays the same on the display DSP. It is to be understood that providing, of information such as records, and the interface, not only denotes displaying something on the screen but also encompasses notification by sound/voice, information in Braille, etc.

The record presentation process is a process of retrieving and presenting an execution result of an executed application. Specifically, in the record presentation process, the management device 1 retrieves execution results of applications executed by a user and another user from the server SV. In the record presentation process, the management device 1 presents a record of the user and a record of the other user(s), arranged in a ranking list, according to a user's choice. The execution result(s) mentioned herein may comprise a usage history of the plurality of applications. The record presentation process may comprise presenting the usage history of the plurality of applications associated with a specific user as a whole. It is to be understood that the usage history may not only include a simple time-series history but also include data obtained through processing, computing, etc. of the time-series history. For example, an application usage rate may be one example of the usage history.

The application may include a game using the seat S. In this case, the execution result may include a game score. The execution result may comprise at least one of pieces of data selected from: an amount of calories burned, an application execution date, an application execution time of the day, the number of times of execution of the application, an application execution place, and an application title.

Figure 2:
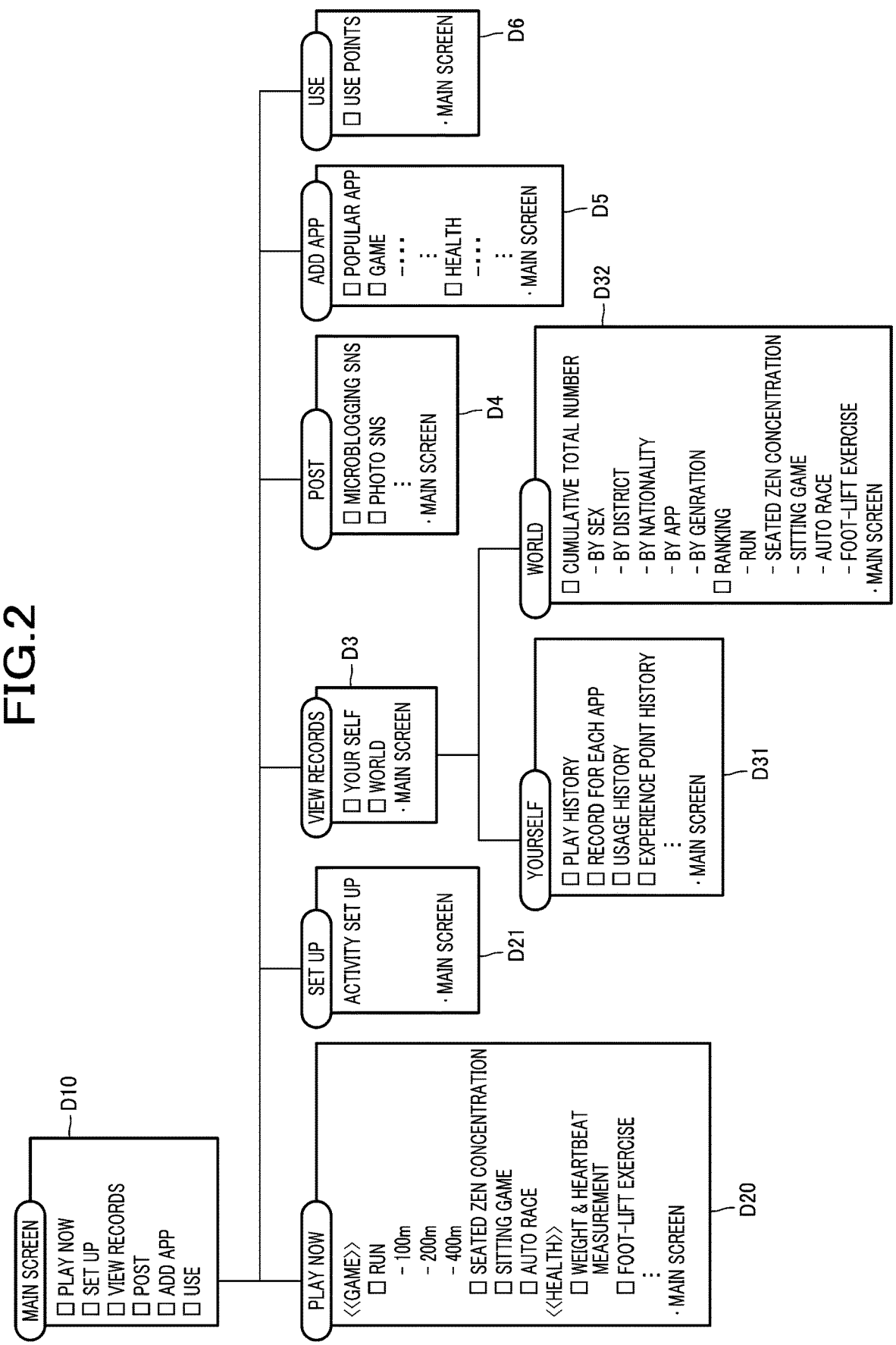
FIG. 2 is a diagram for explaining a transition in a screen of a seat application management device.

FIG. 2 is a diagram for explaining a transition of screens on the display DSP of the smartphone SP, as implemented by the management device 1 according to the present embodiment.

When a seat application management program PG1 is executed, a main screen D10 is displayed on the display DSP. The main screen D10 shows a menu of "PLAY NOW", "SET UP", "VIEW RECORDS", "POST", "ADD APP", "USE", etc.

When "PLAY NOW" is chosen, an app selection screen D20 showing apps available for execution is displayed. The app selection screen D20 is an interface that allows a user to select at least one application from among a plurality of applications each of which offers an experience using the seat S. The app selection screen D20 displays games such as "RUN", "SEATED ZEN CONCENTRATION", "SITTING GAME", "AUTO RACE", etc., as selectable buttons. Also displayed as selectable buttons are applications (also called "app" in abbreviated form throughout this description), such as "WEIGHT & HEARTBEAT MEASUREMENT", "FOOT-LIFT EXERCISE", and other apps, for promoting good health. The button for going back to "MAIN SCREEN" is displayed, too.

The RUN game is a game in which a user on the seat S moves his/her legs up and down alternately to thereby cause a character on the display DSP to run. The more quickly the legs are moved up and down, the faster the character can be caused to run. Then, the RUN game app outputs a game score, e.g., ranking, time taken in running the full distance, etc. as an execution result, to the display DSP and the server SV. The RUN game may preferably offer the option of categories based on distances, such as 100 meters, 200 meters, 400 meters, etc.

The SEATED ZEN CONCENTRATION game is a game in which a user tries to sit still on the seat S, with the center of gravity of his/her body being displayed on the display DSP, and tries to adjust his/her sitting posture to bring the center of gravity close to a reference point on the display DSP. The closer the center of gravity of his/her body to the reference position on the display DSP, the higher score can be achieved. The SEATED ZEN CONCENTRATION game app outputs a game score, e.g., the score achieved as mentioned above, etc., as an execution result, to the display DSP and the server SV.

The SITTING GAME is a game in which a user tries to assume a good sitting posture on the seat S. The closer to an ideal value the pressure value acquired by each of the pressure sensors PS1 to PS6, the higher score can be achieved. The SITTING GAME app outputs a game score, e.g., the score achieved as mentioned above, etc., as an execution result, to the display DSP and the server SV.

The AUTO RACE is a so-called racing game in which a user can make a right turn or a left turn by leaning his/her body rightward or leftward on the seat S, and adjust the speed of the car by leaning his/her body forward or backward. The AUTO RACE app outputs a game score, e.g., ranking and time of the race, the best lap time, etc., as an execution result, to the display DSP and the server SV.

The WEIGHT & HEARTBEAT MEASUREMENT determines the body weight and the heart rate from pressures measured by the pressure sensors PS1 to PS6, and outputs them as an execution result, to the display DSP and the server SV.

The FOOT-LIFT EXERCISE is an application played by a user who move his/her legs up and down in time to the moving images displayed on the display DSP of the smartphone SP and/or the music outputted from the speaker of the smartphone SP. It determines a score based on how exactly his/her motion has synchronized with the music, and outputs the thus-determined score as an execution result, to the display DSP and the server SV.

Herein, the game refers to an app for offering an experience on the seat S in response to the motion (including retention of the posture) of the user and to all apps that output scores of some kind as an execution result. In the example screen of "PLAY NOW" of this embodiment, the FOOT-LIFT EXERCISE is shown as an app falling under the "HEALTH" category for the sake of clarity; it is however to be understood that the FOOT-LIFT EXERCISE is also a game because it outputs the score as an execution result.

The "MAIN SCREEN" button is a button which is clicked or otherwise chosen by a user to go back to the main screen D10. The "MAIN SCREEN" button is displayed in all the screens except the main screen D10, and its function is common; therefore, a description thereof will be omitted for the other screens.

When "SET UP" is chosen in the main screen D10, an activity set-up screen D21 for setting up a target for each activity using the seat S is displayed.

When "VIEW RECORDS" is chosen in the main screen D10, a record selection screen D3 offering the option of types of records is displayed. The record selection screen D3 displays "YOURSELF" and "WORLD" buttons.

When "YOURSELF" is chosen in the record selection screen D3, a user record screen D31 showing the operating user's own record is displayed. The user record screen D31 shows records, not only of one application, but of a plurality of applications retrieved by a search, conducted by using a user ID as a search key, for applications associated with the user ID. Specific examples, which will be described later, include information regarding a play history, a record for each app, an activity history, an experience point history, etc. among which execution results associated with the user ID (i.e., the results of execution by the currently operating user) are displayed. The user ID has a unique value associated with the user. The user ID may be a string of alphanumeric characters.

When "WORLD" is chosen in the record selection screen D3, a world record screen D32 showing the records of the operating user and the records of the other user(s) is displayed. The world record screen D32 shows a cumulative total number of experiences, as classified by sex, district, nationality, app, or generation. The records of the user and the records of the other user(s) are arranged in a ranking list for each game. When the records of the user are not so good, the records of the user may not be shown in the results, or the records of a lower-rank group to which the user belongs may be shown while those of a middle-rank group of users may be omitted from the ranking list.

When "POST" is chosen in the main screen D10, a posting screen D4 is displayed. The "POST" herein refers to uploading information on a so-called SNS (Social Networking Service). For example, the posting screen D4 shows Internet links to sites of a microblogging SNS for posting short messages or tweets, a photo SNS for posting photos, etc., or buttons for calling up dedicated SNS applications, for posting in the SNS an article about an app being currently experienced.

When "ADD APP" is chosen in the main screen D10, an app addition screen D5 is displayed. The app addition screen D5 shows Internet links to sites for launching an application to add apps or buttons for calling up an application to add apps, for installing an application using the seat S.

When "USE" is chosen in the main screen D10, a use screen D6 is displayed, which shows a plurality of Internet links to Internet sites in which reward points amassed through execution of apps can be used.

Next, a setup for presenting such screens will now be described below.

Figure 3:
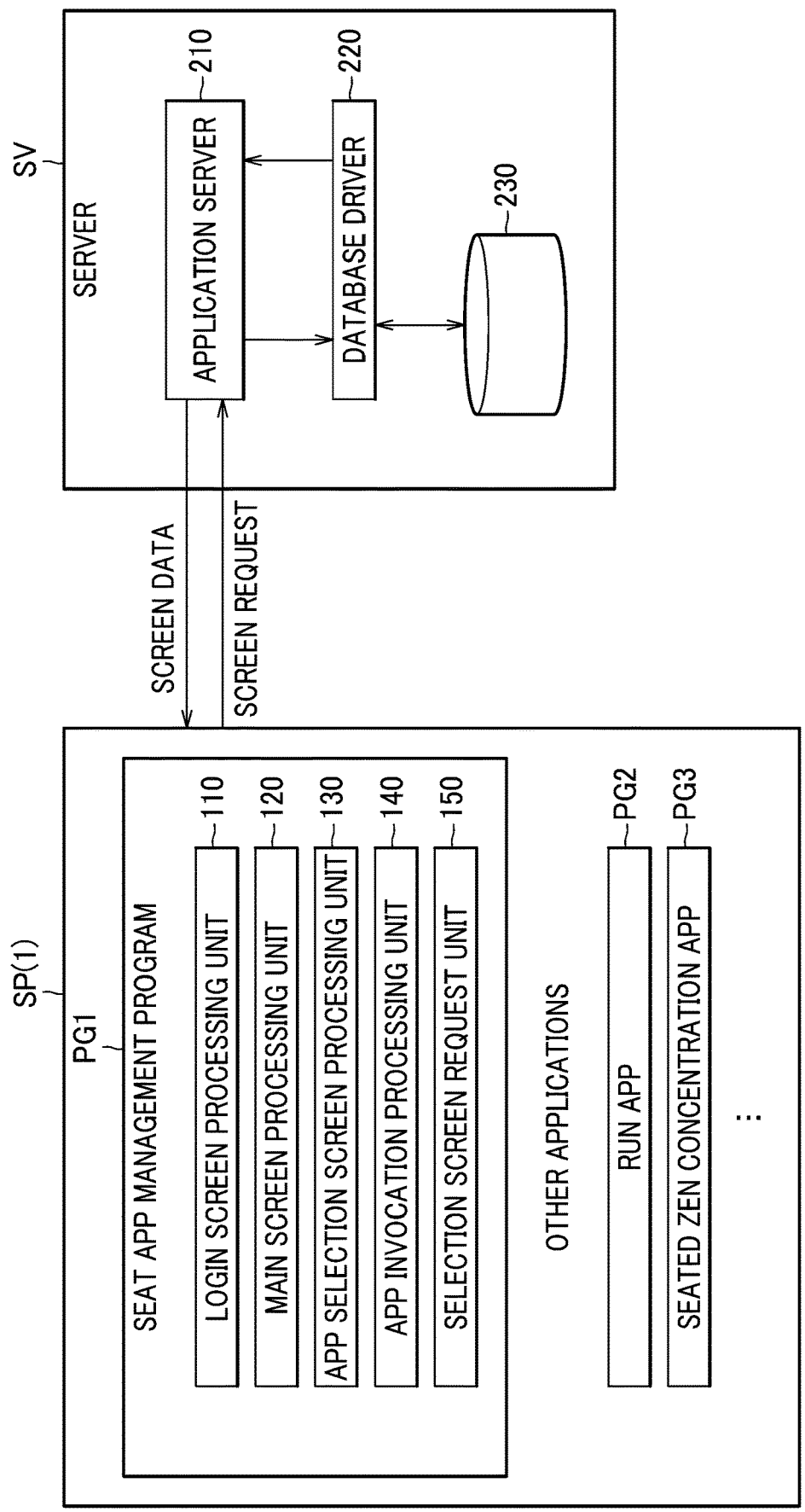
FIG. 3 is a block diagram showing configurations of the seat application management device and a server.

As shown in FIG. 3, the smartphone SP stores a seat application management program PG1 and a plurality of other application programs, such as a RUN app PG2, a SEATED ZEN CONCENTRATION app PG3, etc. As mentioned above, the management device 1 is implemented through execution of the seat application management program PG1.

The seat application management program PG1 includes a login screen processing unit 110, a main screen processing unit 120, an app selection screen processing unit 130, an app invocation processing unit 140, and a selection screen request unit 150.

The login screen processing unit 110 displays a login screen on the display DSP for entering a user ID and a password if no login operation has been performed after the seat application management program PG1 has been launched. Once the user ID and the password have been entered, the login screen processing unit 110 transmits the user ID and the password to the server SV with a login request.

The main screen processing unit 120 executes a process of displaying the main screen D10 on the display DSP. The main screen processing unit 120 calls up the next process corresponding to the button chosen in the main screen D10.

When the "PLAY NOW" button is chosen in the main screen D10, the app selection screen processing unit 130 displays an app selection screen D20. When the main screen D10 is chosen in the app selection screen D20 or any other screen, the main screen D10 is displayed by the main screen processing unit 120.

When an app is chosen in the app selection screen D20 or any other screen, the app invocation processing unit 140 calls up or invocates the other application program, e.g., RUN app PG2, etc., stored in the smartphone SP, for execution. When the execution of the invoked other program comes to an end, the main screen D10 is displayed by the main screen processing unit 120.

The app, thus invoked, transmits an execution result not explained herein in detail but including an execution date and time (of the day), a game score, etc., as associated with the user ID, to the server SV. The invoked app also determines a point score earned according to the type of the app, the number of times of execution of the app, the execution result of the app (e.g., game score, etc.), and transmits the earned point score as associated with the user ID, to the server SV. The server SV then stores the execution result and the point score associated with the user ID.

When an option other than "PLAY NOW" is chosen in the main screen D10, the selection screen request unit 150 requests the chosen screen from the server SV. The screen presented to the user as an option for the screen other than the app selection screen D20 may be an invariable screen in some cases, or a screen varying with the user, etc., e.g., showing the extracted or otherwise processed records in other cases. In cases where the presented screen is variable, the selection screen request unit 150 requests screen data with data extraction criteria and screen type specified, from the server SV. In other words, the button for requesting a variable screen, as provided in each screen, is a button to which a command requesting data of a screen including the type of the screen and the data extraction criteria is assigned, to receive the requested screen data from the server SV. The selection screen request unit 150 displays a screen based on the received screen data, on the display DSP. When a user makes a request for a screen for viewing records, the selection screen request unit 150 executes a record presentation process in response to the request.

The server SV comprises an application server 210, a database driver 220, and a storage unit 230.

The storage unit 230 stores invariable screens to be displayed by the management device 1, and records of users' in-seat experiences associated with the corresponding users as structured in a database.

For example, as shown in FIG. 4, the storage unit 230 stores (a) a user table, (b) an app experience table, and (c) a usage history table.

The user table stores pieces of data each of which is associated with a user ID of a corresponding user as individual information on the corresponding user. The individual information on a user includes a user name, a password, a country and a city of user's residence, sex, birth date, a targeted goal for each app, etc.

The app experience table stores information regarding apps each of which is associated with a user ID of a corresponding user as an app experienced by the corresponding user. The information regarding apps, stored therein, includes a date and time (of the day) of execution of each app, a name of the app, at least one evaluation (EVALUATION 1, EVALUATION 2, etc., in FIG. 4(*b*)), an amount of calories burned, a point score earned, etc. Moreover, data regarding a place of execution of each app may be stored therein.

The usage history table stores a type of action such as print, view, etc., a date and time (of the day) of execution of each action, an executing person, etc.

The application server 210 receives a request for a screen from the management device 1, and transmits data of the screen which meets the request, to the management device 1.

When an invariable screen is requested, the application server 210 retrieves the invariable screen from the storage unit 230, and transmits the same to the management device 1.

When a screen of a specified screen type with specified data extraction criteria is requested from the management device 1, the application server 210 gives the database driver 220 an instruction to extract data with the specified extraction criteria from the database in the storage unit 230.

The database driver 220, responding to this instruction, extracts the data from the storage unit 230 and sends the same to the application server 210. The application server 210 forms image data of a screen of the requested type from the received data, and transmits the image data to the management device 1.

Next, one example of the process executed by the management device 1 will be described below.

Figure 5:
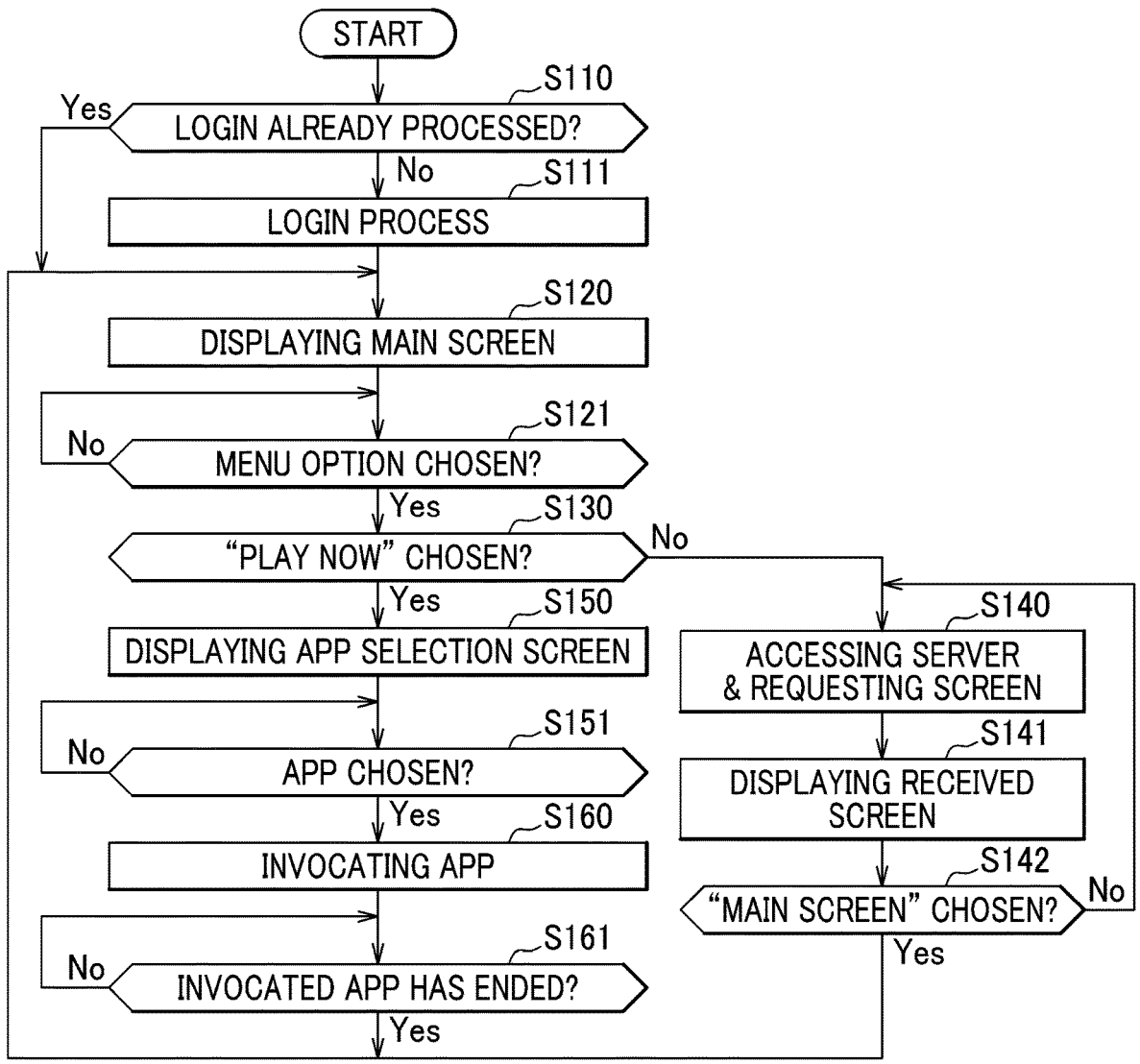
FIG. 5 is a flowchart showing one example of a process of the seat application management device.
Figure 6:
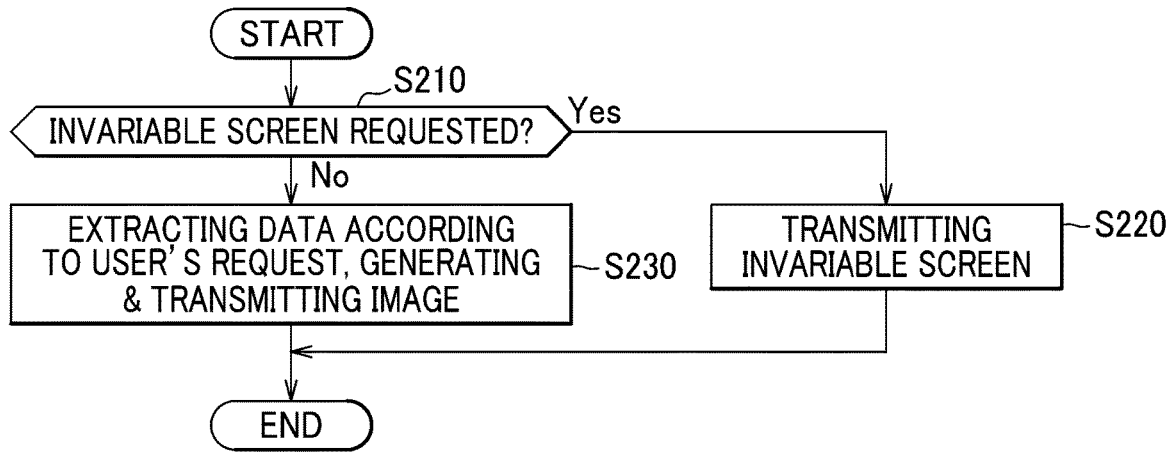
FIG. 6 is a flowchart showing one example of a process of the server.

As shown in FIG. 5, when the management device 1 is started, the management device 1 determines whether or not the login has already been processed (S110), and if already processed (Yes, S110), then proceeds to step S120 to display the main screen D10. On the other hand, if the login has not been processed yet (No, S110), then the management device 1 executes the login process (S111), and thereafter proceeds to step S120 to display the main screen D10.

While displaying the main screen D10 (S120), the management device 1 determines whether or not any menu option has been chosen (S121), and waits until one of the menu options is chosen (No, S121). If one of the menu options has been chosen (Yes, S121), the management device 1 determines whether or not the chosen menu option is "PLAY NOW" (S130).

If "PLAY NOW" has been chosen (Yes, S130), then the management device 1 displays an app selection screen D20 (S150). Then, the management device 1 waits until an app is chosen in the app selection screen D20 (No, S151). If the app has been chosen in the app selection screen D20 (Yes, S151), then the management device 1 invocates and executes the chosen app (S160). Then, the management device 1 waits until the invocated app ends (No, S161), and if the app has ended (Yes, S161), then goes back to step S120 to display the main screen D10.

In step S130, if "PLAY NOW" is not the one that has been chosen (No, S130), the management device 1 accesses the server SV, and requests a screen chosen by the user therefrom (S140). When the management device 1 receives data of the screen from the server SV, the management device 1 displays the screen of the received data on the display DSP (S141).

Then, the management device 1 determines whether or not a button chosen from the options shown in the displayed screen is the main screen D10 (S142), and if it is the main screen D10 (Yes, S142), then goes back to step S120 to display the main screen D10. On the other hand, if the button chosen from the options shown in the displayed screen is not the main screen D10 (No, S142), then the management device 1 goes back to step S140 to access the server SV and request a screen chosen by the user therefrom.

The management device 1 repeats the process steps as described above until the seat application management program PG1 has been exited by the user.

Next, one example of the process of the server SV will be described below.

Upon receipt of a request from the management device 1, the server SV determines whether or not the received request is a request for an invariable screen (S210). If the request from the management device 1 is a request for an invariable screen (Yes, S210), then the server SV retrieves data of the invariable screen from the storage unit 230 and transmits the same to the management device 1 (S220). On the other hand, if the request from the management device 1 is not a request for an invariable screen (No, S210), then the server SV extracts data which meets the user's request, from the database in the storage unit 230, and generates and transmits screen data to the management device 1 (S230).

Figure 7:
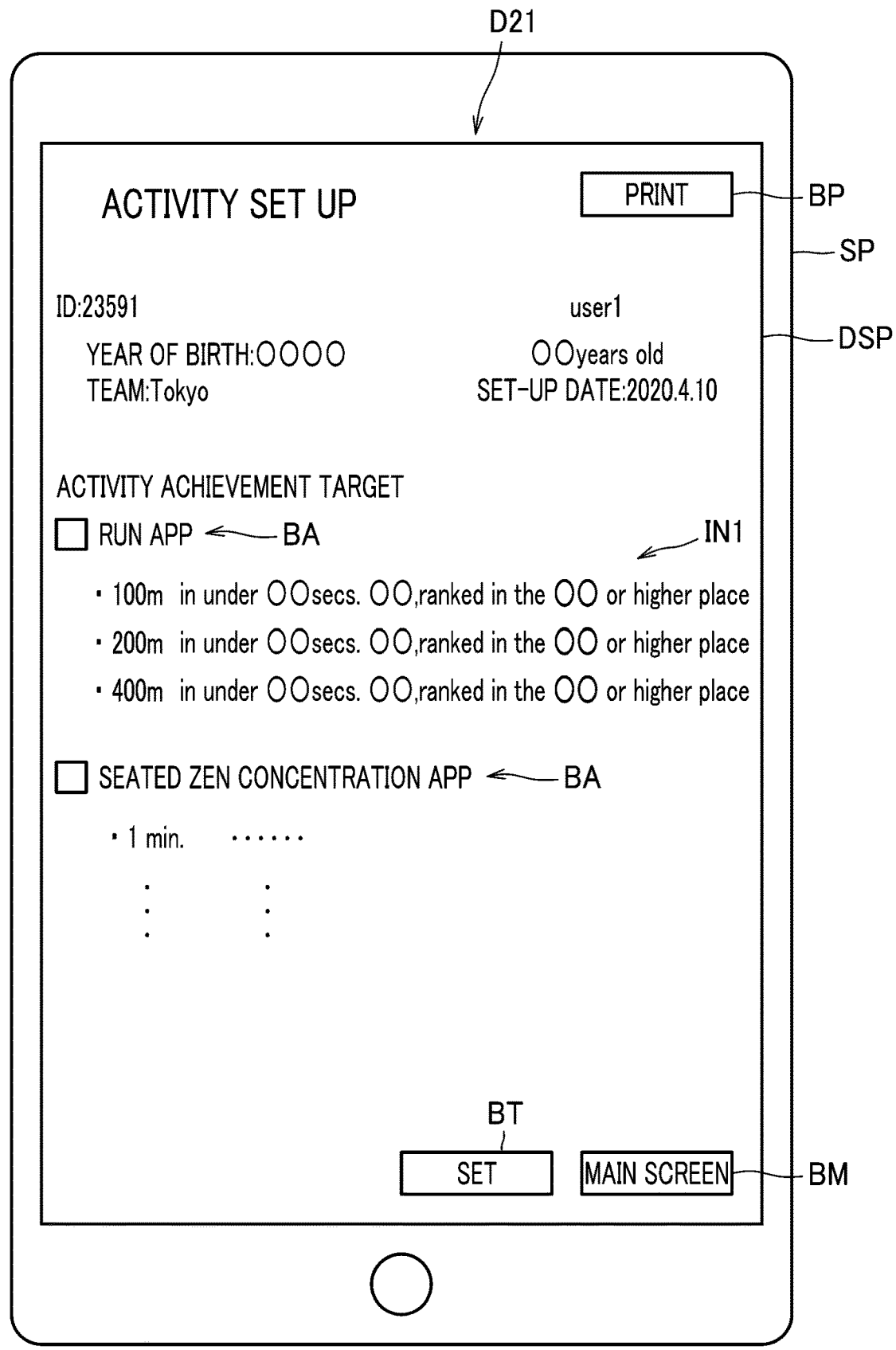
FIG. 7 is one example of a screen of an activity set up.

In the seat application management device 1 configured as described above, for example, when a user chooses "SET UP" in the main screen D10, the management device 1 transmits a corresponding user ID and a requested screen type "SET UP" to the server SV. Accordingly, the server SV extracts data by using the user ID as a search key from the user table, and generates and transmits screen data for an activity set up to the management device 1. One example of a screen formed by this screen data is shown in FIG. 7. As shown in FIG. 7 by way of example, the activity set-up screen D21 shows user information such as an ID, a date of birth, a city of residence, a name, an age, etc. of the user, and a set-up date. The city of residence may preferably be dubbed and shown by a team name for an area of the residence to enhance a sense of togetherness. The activity set-up screen D21 further shows an entry field IN1 for setting a goal for each of a variety of apps, as an activity achievement target. In the entry field IN1 for setting a goal, prior to any change in the setting, values currently set in the user table are shown. The activity set-up screen D21 shows buttons which include a SET button BT for confirming the value(s) entered in the entry field IN1 and transmitting the value(s) to the server SV, and a MAIN SCREEN button BM for going back to the main screen D10. In an upper part of the screen, a PRINT button BP for transmitting print data to a printer to print currently displayed setting information is shown.

Character strings of app names such as "RUN app", "SEATED ZEN CONCENTRATION app", etc., for representing app titles are each associated with a command for launching a corresponding app in response to the choice of a character string, so that each character string functions as an APP START button BA for launching the corresponding app. When any of the APP START buttons BA is chosen, the management device 1 invocates and executes one of the other application programs, e.g., RUN app PG2, etc., stored in the smartphone SP.

For example, when a user chooses "VIEW RECORDS" in the main screen D10, chooses "YOURSELF" in the record selection screen D3, and chooses "PLAY HISTORY" in the user record screen D31, the management device 1 transmits a corresponding user ID and a requested screen type "PLAY HISTORY" to the server SV. Accordingly, the server SV extracts data by using the user ID as a search key from the accumulated app experience table, and generates and transmits a screen data for the user's own play history to the management device 1. One example of a screen formed by this screen data is shown in FIG. 8 by way of example.

Figure 8:
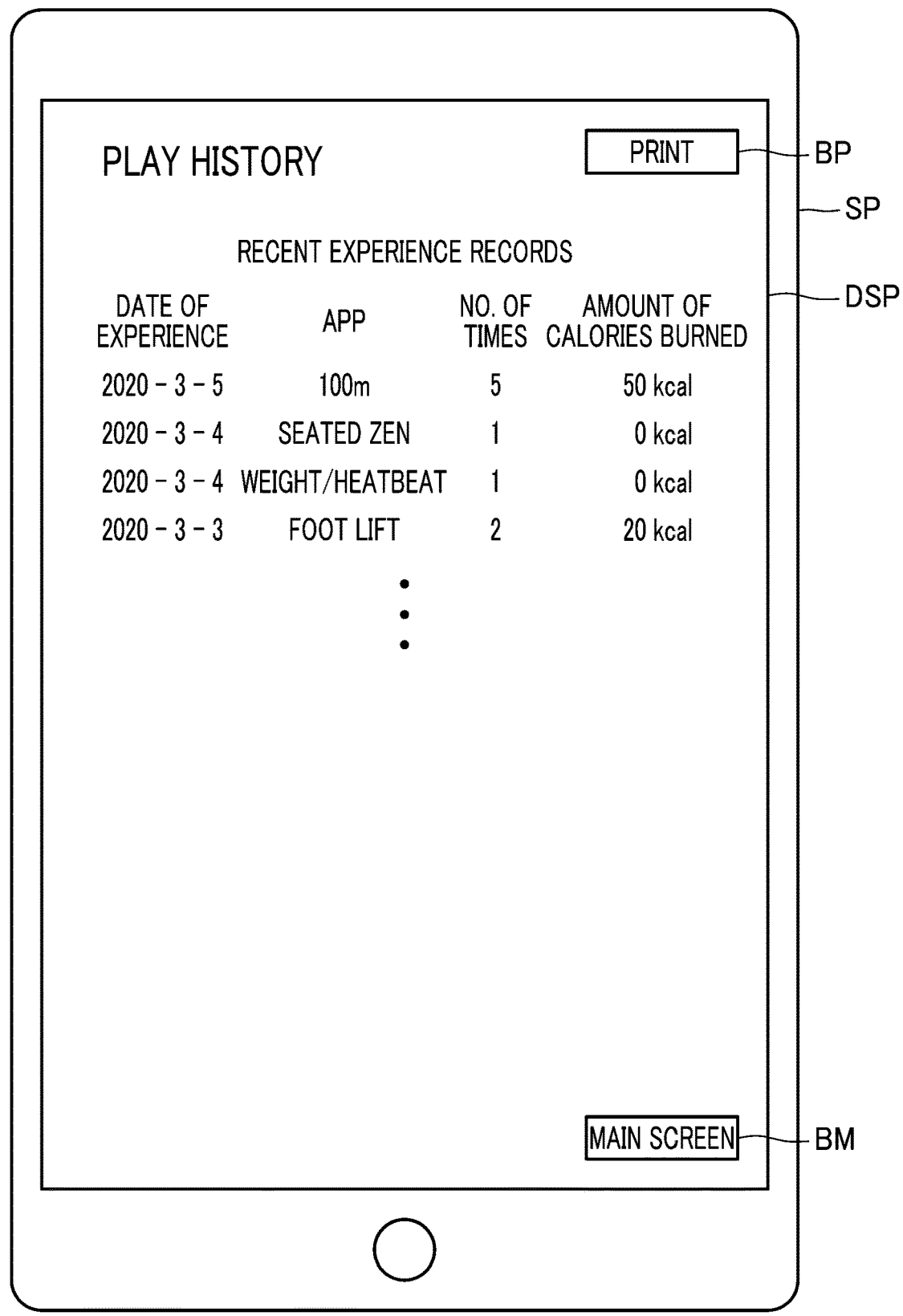
FIG. 8 is one example of a screen of a play history.

The screen example illustrated in FIG. 8 shows a list of recent time-series in-seat experiences of the user arranged down in rows, as a play history. This list shows the execution result including a date of the experience, an app title, the number of times of execution of each app, and an amount of calories burned, which are arranged in a single row. This screen also shows a MAIN SCREEN button BM for going back to the main screen D10, and a PRINT button BP for printing the contents displayed in the screen.

Thus, in the management device 1, the execution results of a plurality of applications can be arranged and displayed together for a specific user. Further, the execution results arranged together for a specific user can be printed out.

Figure 9:
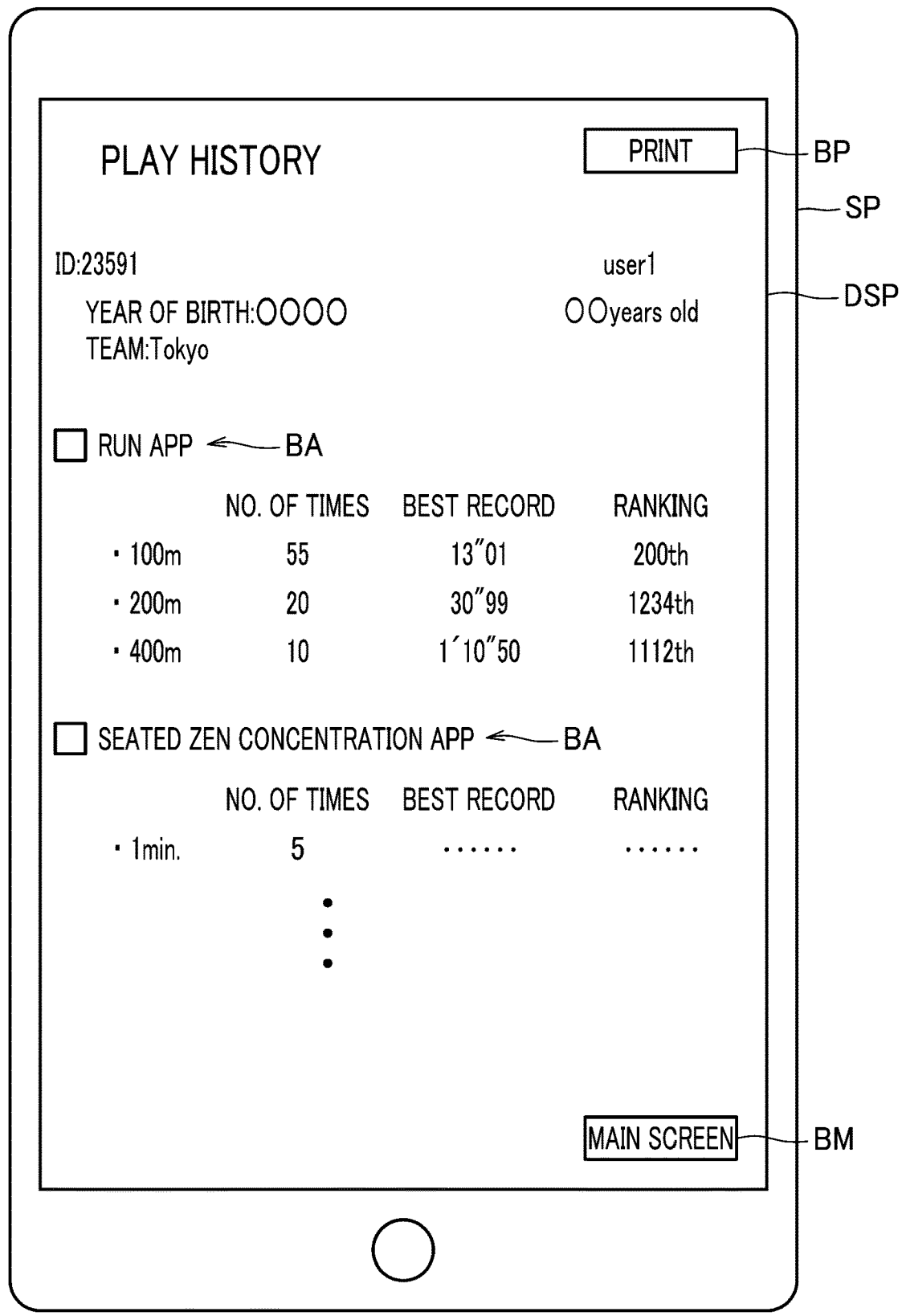
FIG. 9 is another example of a screen of the play history.

The PLAY HISTORY screen may be a screen, for example, as shown in FIG. 9. In this screen, information about a user is shown in an upper part thereof, under which the execution results of apps arranged together for each app are shown. For example, for each app, an accumulated number of times of execution of the app, a maximum score, and ranking are shown as the execution results. In this PLAY HISTORY screen as well, character strings of app names are each associated with a command for launching a corresponding app in response to the choice of a character string, so that each character string functions as an APP START button BA for launching the corresponding app. When any of the APP START buttons BA is chosen, the management device 1 invocates and executes one of the other application programs stored in the smartphone SP.

When a user chooses "RECORD FOR EACH APP" in the user record screen D31, the management device 1 transmits a corresponding user ID and a requested screen type "RECORD FOR EACH APP" to the server SV. Accordingly, the server SV extracts data by using the user ID as a search key from the accumulated app experience table, and transmits a screen data for the user's own record for each app to the management device 1. One example of a screen formed by this screen data is shown in FIG. 10 by way of example.

The screen example illustrated in FIG. 10 shows, as the user's own records, a list of the execution result (scores) of experiences arranged down in rows, each including a date of experience, a category, and a time, for a single experience in the RUN app.

Another list of the execution result (scores) of experiences in the AUTO RACE app that is an app other than the RUN app is shown, in which the experiences are arranged down in rows, each including a date of experience, a rank, a time, and a best lap time. Also in this screen, a MAIN SCREEN button BM for going back to the main screen D10, and a PRINT button BP for printing the contents displayed in the screen are shown. In this RECORD screen as well, character strings of app names are each associated with a command for launching a corresponding app in response to the choice of a character string, so that each character string functions as an APP START button BA for launching the corresponding app. When any of the APP START buttons BA is chosen, the management device 1 invocates and executes one of the other application programs stored in the smartphone SP.

With the management device 1 configured as described above, the results of execution of a plurality of applications can be displayed in groups of specific users and in groups of apps.

When a user chooses "WORLD" in the record selection screen D3, and chooses "RUN" in "RANKING" in the world record screen D32, the management device 1 transmits a requested screen type "WORLD RANKINGS OF RUN" to the server SV. Accordingly, the server SV extracts data by using the RUN app as a search key from the accumulated app experience table, and generates and transmits a screen data of ranking formed by sorting records for each category, to the management device 1. One example of a screen formed by this screen data is shown in FIG. 11 by way of example.

Figure 11:
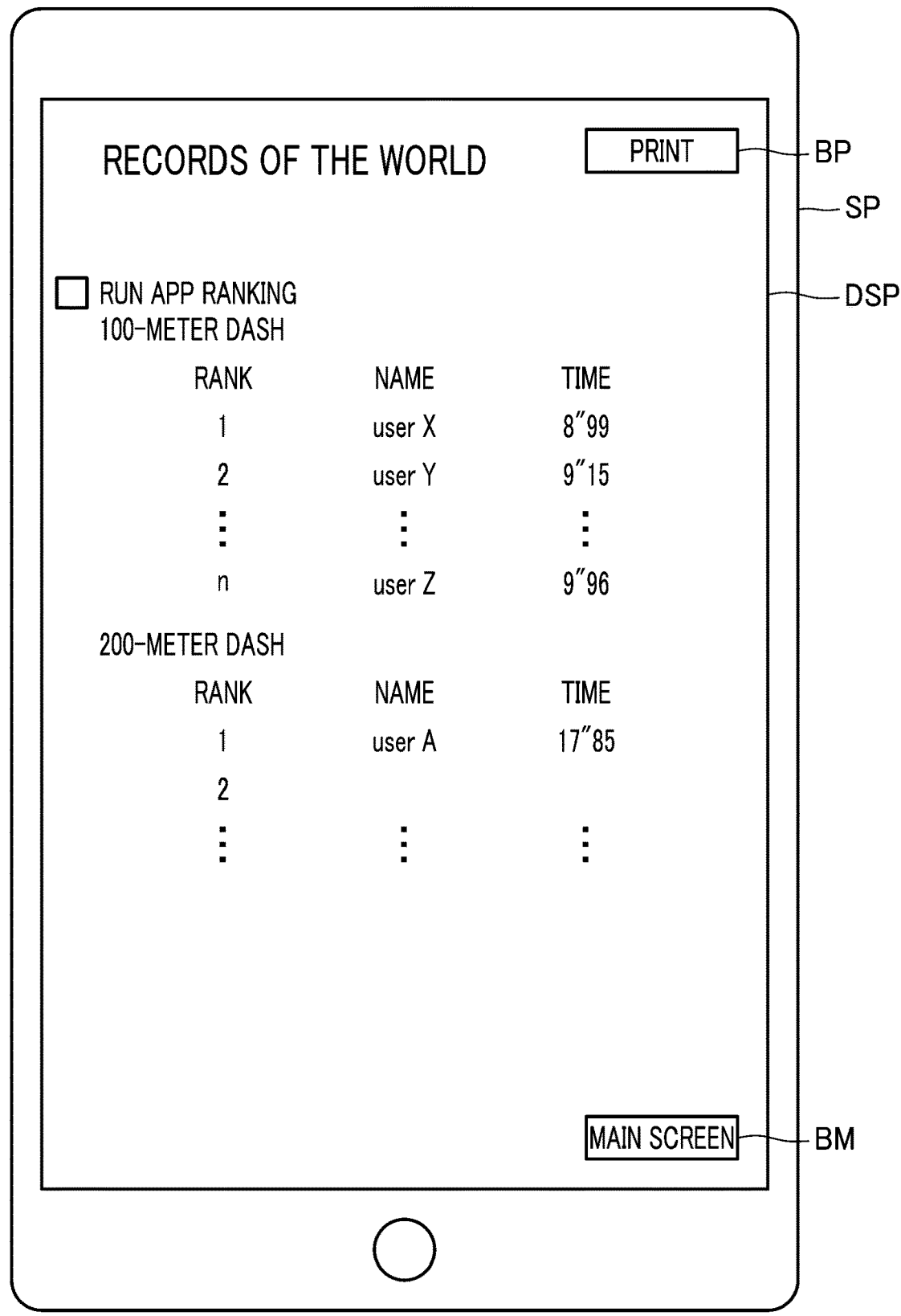
FIG. 11 is one example of a screen of records of the world.

The screen example illustrated in FIG. 11 shows, as the world ranking for the RUN app, a list of ranking from the first rank down to a predetermined lower rank for each category such as 100-meter dash, 200-meter dash, etc. A single row of the list shown for each rank includes information, for example, about the ordinal rank, a name, and a time. Also, in this screen, a MAIN SCREEN button BM for going back to the main screen D10, and a PRINT button BP for printing the contents displayed in the screen are shown.

With the management device 1 configured as described above, the user's own and the other users' execution results (scores) can be shown in a list of ranking.

When a user chooses "YOURSELF" in the record selection screen D3, and chooses "USAGE HISTORY" in the user record screen D31, the management device 1 transmits a requested screen type "USAGE HISTORY" to the server SV. Accordingly, the server SV extracts data by using the user ID as a search key from the accumulated user table, app experience table and usage history table, and generates and transmits a screen data of lists of user's experience records, view records, and print records, to the management device 1. One example of a screen formed by this screen data is shown in FIG. 12 by way of example.

Figure 12:
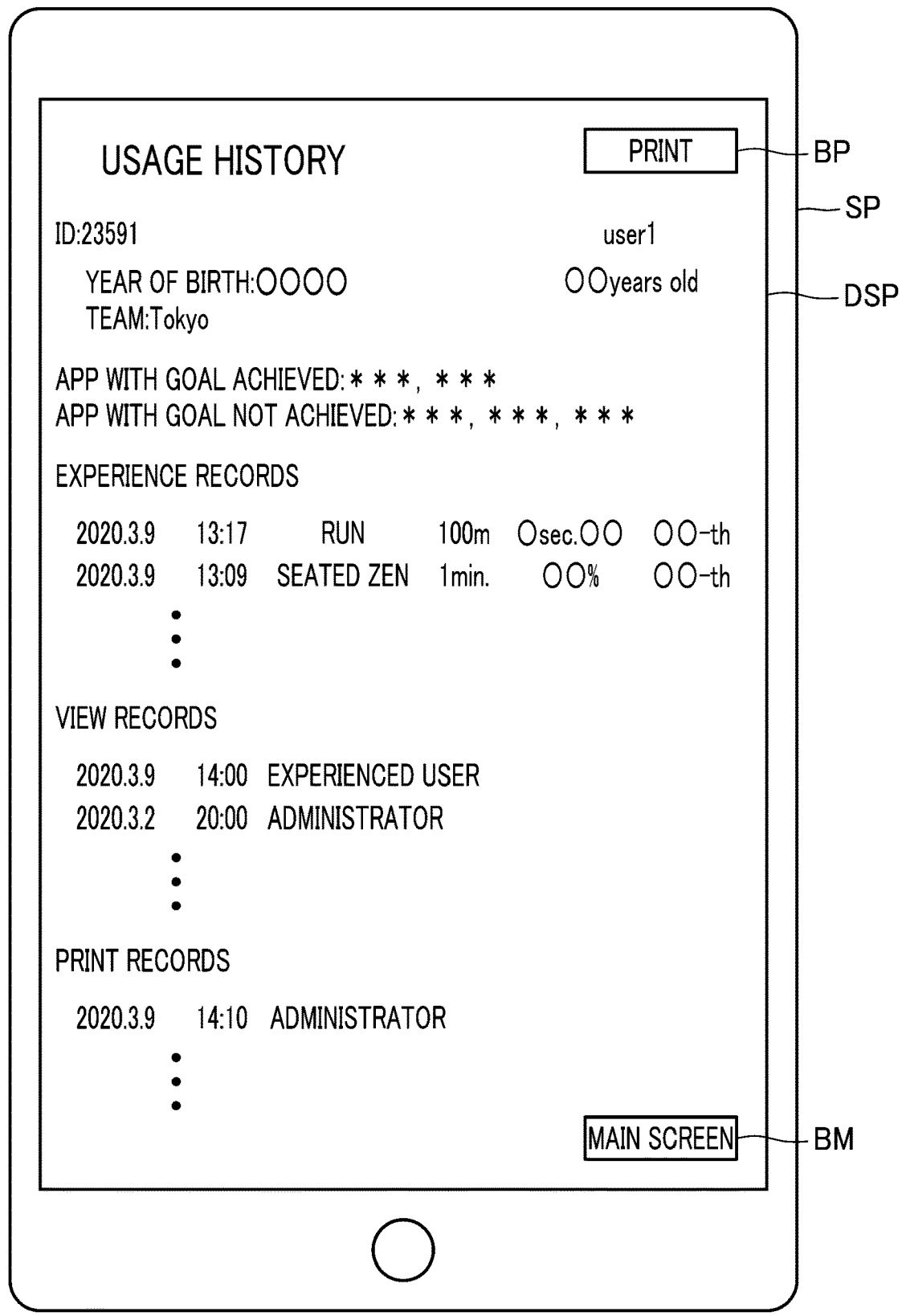
FIG. 12 is one example of a screen of a usage history.

In the screen of FIG. 12, information about a user is shown in an upper part thereof, under which a list of apps with their goals achieved, a list of apps with their goals not achieved, experience records, view records, and print records are shown.

Each experience record includes a date and time (of the day) of execution of an app, an app name, a category, a record (time), and a rank, arranged in a row. The experience records are listed sequentially from the newest placed at the top down toward the oldest.

Each view record includes a date and time (of the day) of viewing, and a person who viewed, arranged in a row. The view records are listed sequentially from the newest placed at the top down toward the oldest.

Each print record includes a date and time (of the day) of printing, and a person who printed, arranged in a row. The print records are listed sequentially from the newest placed at the top down toward the oldest.

Also, in this screen, a MAIN SCREEN button BM for going back to the main screen D10, and a PRINT button BP for printing the contents displayed in the screen are shown.

Character strings of app names, of the apps with their goals achieved and with their goals not achieved, may each be associated with a command for launching a corresponding app in response to the choice of a character string, so that each character string functions as an APP START button BA for launching the corresponding app.

When a user chooses "YOURSELF" in the record selection screen D3, and chooses "EXPERIENCE POINT HISTORY" in the user record screen D31, the management device 1 transmits a requested screen type "EXPERIENCE POINT HISTORY" to the server SV. Accordingly, the server SV extracts data by using the user ID as a search key from the accumulated app experience table, and generates and transmits a screen data of user's experience records with amassed points aggregated, to the management device 1. One example of a screen formed by this screen data is shown in FIG. 13 by way of example.

Figure 13:
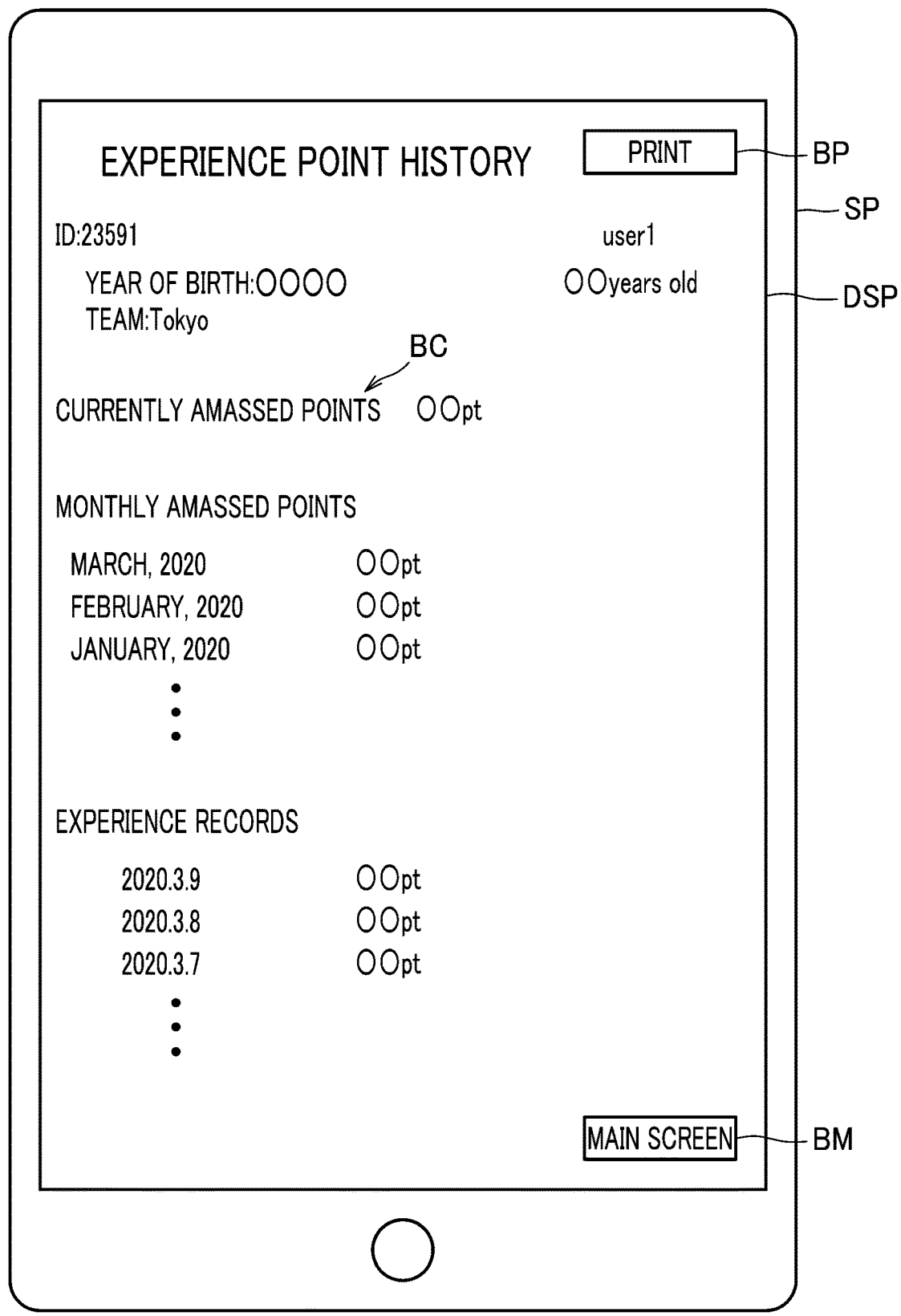
FIG. 13 is one example of a screen of an experience point history.

In the screen of FIG. 13, information about a user is shown in an upper part thereof, under which currently amassed points, monthly amassed points, and experience records are shown.

The currently amassed point record shows a cumulative point score earned through execution of the apps.

Each monthly amassed point record includes a month and a point score earned within the month, arranged in a row. The monthly amassed point records are listed sequentially from the newest placed at the top down toward the oldest.

Each experience record includes a date of experience and an earned point score arranged in a row. The day-to-day earned point scores are listed sequentially from the newest placed at the top down toward the oldest.

Also in this screen, a MAIN SCREEN button BM for going back to the main screen D10, and a PRINT button BP for printing the contents displayed in the screen are shown.

Character strings of "CURRENTLY AMASSED POINTS" provide a link to the use screen D6. Accordingly, by tapping to choose "CURRENTLY AMASSED POINTS", the use screen D6 is displayed so that the points can be used.

As described above, with the seat application management device 1 implemented by executing the seat application management program PG1, the following advantageous effects can be achieved.

With this management device 1, options of selectable applications can be offered for execution, and thus the experiences using the seat S can be enjoyed with ease. Furthermore, the execution result of the executed application can be presented, and thus user's own in-seat S experiences can be pieced together, so that the state of the experiences can be easily grasped as a whole.

Since the management device 1 is configured to execute the record presentation process in which execution results of applications executed by the user and by other users are retrieved from the server and presented, the user can look into the other users' execution results as well as his/her own execution result; thus, through comparison, or otherwise, the user can be motivated into the experience provided in the seat S.

Since the management device 1 can present, in the record presentation process, the record of the user and the records of the other users arranged in a ranking list, the record of the user and the records of the other users can be viewed as arranged in the ranking list. Therefore, the user can be more motivated into the experience provided in the seat S.

Since the usage history of the plurality of applications associated with a specific user can be viewed in to-to, the specific user's experience in the seat S can be pieced together and grasped as a whole.

Although the first embodiment has been described above, specific configurations thereof may be modified where deemed appropriate.

For example, the embodiment above is illustrated by a specific configuration in which the smartphone SP is used to implement the management device 1, but a tablet PC, a desktop computer, a laptop computer, a navigation system, etc. may be used instead for its implementation. Further, any of the necessary processes may be executed by any device. For example, the embodiment above is illustrated by a specific configuration in which all the processes of providing interfaces through which a user is allowed to choose an application are executed by the smartphone SP; however, an alternative configuration may be feasible in which part of the processes is executed by the other computer such as the server SV or the like. In other words, the seat application management device may be configured to operate by the other computer and the smartphone SP operating in coordination with each other. Moreover, the storage unit for storing data necessary for the processes may be located anywhere as long as data communication with the device(s) mainly constituting the management device 1 is available.

In describing the embodiment above, only some examples of applications using the seat S are illustrated, but the applications are not limited to those illustrated above.

In describing the embodiment above, a string of alphanumeric characters is illustrated as the user ID, but biometric identification data with which an individual person can be authenticated, for fingerprint or face authentication can be used.

In describing the embodiment above, posting in SNS is illustrated as implemented by calling up existing SNS applications, or otherwise, but the SNS functionality may be implemented in the seat application management device (seat application management program) itself. In this configuration, the SNS functionality as implemented may include a function of allowing a user to make the results of his/her own in-seat experience open to the others, and/or a function of allowing other user(s) to make a comment on a content laid open. With this feature, a user is highly motivated to execute the application using the seat S. In addition, through such applications, chances to make one another's acquaintance or to build a community can be provided.

In the process of posting information in SNS or on-line community, information laid open may preferably be provided with a level configurable arbitrarily for each of other users (partners in the community).

An optional configuration may be provided in which the action of posting of information in SNS or on-line community are accompanied by granting of reward points.

When information about the height, weight, sex, etc. of a user is entered in the seat application management device, a user may be invited to take a photo by a camera so that the information about the height, weight, sex, etc. of the user is presumed from the captured image by deep learning and set automatically. In this way, entry of information can be made easily; for example, the change of the height and/or weight can be entered easily so that updating or renewal of the information can be made easier.

Moreover, photos of user's daily meals may be taken by a camera, and the menu items of the meal and the amount of calories may be computed automatically from the captured image of the meal by deep learning, to be recorded as historical records of user information.

The seat application management device may be configured to be capable of sharing data with smartwatches, sport watches for runners, and/or body composition analyzers, so that information about physical exercises and/or health may be taken in and recorded. In this way, the health condition can be managed collectively as a whole.

In describing the embodiment above, one example in which information is shown on a display screen and presented to a user is illustrated, but such information may be presented by sound/voice, and/or in Braille.

In describing the embodiment above, the pressure sensors are taken as an example of a sensor, but the sensor may be other types of sensors, for example, a capacitance sensor may be used instead. For the purpose of measuring pressure, a pressure distribution sensor may be adopted.

In describing the embodiment above, the wireless communication is used to connect the control unit and the smartphone, but a cable communication may be used to connect them.

In describing the embodiment above, the seat installed in a vehicle of an automobile or a car is illustrated as a vehicle seat, but the vehicle seat may be a seat for a car other than an automobile, such as a railcar, or a seat for a vehicle other than a car, such as a ship, aircraft, etc. The seat may also be a seat installed in a training room, a game center, a nursing-care facility, or at home, etc.

Any of the elements explained in relation to the first embodiment and modified examples may be implemented in combination as desired.

Next, a second embodiment will be described in detail with reference to the drawings where appropriate. The front/rear, right/left, and upper (upward)/lower (downward) will be mentioned herein with reference to the front/rear, right/left, and upper (upward)/lower (downward) as viewed from the viewpoint of a person seated on the seat.

Figure 14:
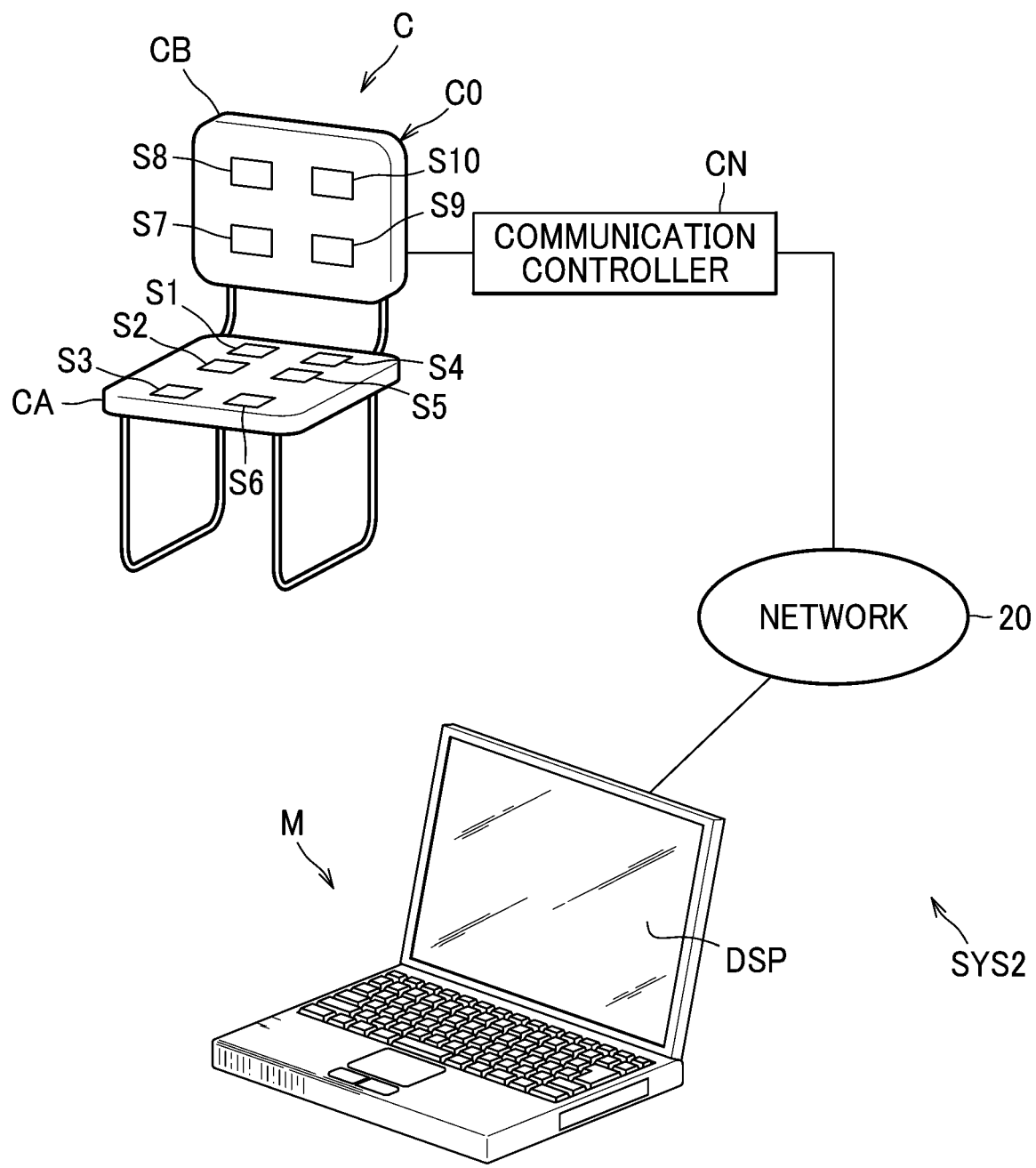
FIG. 14 is a diagram showing a general setup of a seat experiencing system according to a second embodiment.

As shown in FIG. 14, a seat experiencing system SYS2 comprises a seat C, and a terminal M.

The seat C comprises a seat body C0 on which a person is to be seated, a plurality of detection sensors S1 to S10, and a communication controller CN.

The seat body C0 includes a seat bottom CA on which a person is to be seated, and a backrest CB.

The detection sensors S1 to S10 are sensors that detect a person seated on the seat body C0. In this embodiment, the detection sensors S1 to S10 are pressure sensors configured to acquire measurement values of pressure from a person seated on the seat body C0. In the following description, the measurement value of pressure acquired by the pressure sensor S1 is designated by P1, the measurement value of pressure acquired by the pressure sensor S2 is designated by P2, the measurement value of pressure acquired by the pressure sensor S3 is designated by P3; similarly, the measurement value of pressure acquired by the pressure sensor Sn is designated by Pn.

The detection sensors S1 to S10 are provided at the seat body C0. The detection sensors S1 to S10 are arranged in such positions as to face a person seated on the seat body C0.

To be more specific, the detection sensors S1 to S6 are provided at the seat bottom CA of the seat body C0. The detection sensors S1 to S3 and the detection sensors S4 to S6 are located symmetrically with respect to a laterally central position of the seat body C0.

The detection sensors S1, S2, S4, and S5 are located at a rear portion of the seat bottom CA, specifically, in positions corresponding to the buttocks of a person seated on the seat bottom CA. To be more specific, the detection sensors S1, S4 are located in positions, under the lowermost portions of the ischial bones of a person seated on the seat bottom CA, on which the load of the person seated on the seat bottom CA is borne largest. The detection sensors S2, S5 are located in positions a little frontward of the pressure sensors S1, S4. The detection sensors S1, S2, S, 4 and S5 acquire measurement values P1, P2, P4 and P5 of pressure from the buttocks of the person seated on the seat bottom CA. In the following description, the person seated on the seat bottom CA (seat body C0) will be referred to as "occupant".

The detection sensors S3, S6 are located in positions different from those in which the detection sensors S1, S2, S4 and S5 are located, specifically, in positions frontwardly apart from the detection sensors S1, S2, S4 and S5. More specifically, the detection sensors S3, S6 are located in positions corresponding to the thighs of the person seated on the seat bottom CA. To be specific, the detection sensors S3, S6 are located in positions under the thighs of the occupant. To be more specific, the detection sensor S3 is located in a position under the right thigh of the occupant, and the detection sensor S6 is located in a position under the left thigh of the occupant. The detection sensors S3, S6 acquire the measurement values P3, P6 of pressure from the thighs of the occupant.

The detection sensors S7 to S10 are provided at the backrest CB of the seat body C0. The detection sensors S7, S8 and the detection sensors S9, S10 are located symmetrically with respect to the laterally central position of the seat body C0.

The detection sensors S7, S9 are located in positions corresponding to the waist of the occupant. To be more specific, the detection sensors S7, S9 are located in positions at the rear of the waist of the occupant. The detection sensors S7, S9 acquire the measurement values P7, P9 of pressure from the waist of the occupant.

The detection sensors S8, S10 are located in positions upwardly apart from the detection sensors S7, S9, specifically, in positions corresponding to an upper region of the back of the occupant. To be more specific, the detection sensors S8, S10 are located in positions at the rear of the upper region of the back of the occupant. The detection sensors S8, S10 acquire the measurement values P8, P10 of pressure from the upper region of the back of the occupant.

In the present embodiment, the detection sensors S1, S2, S4 and S5 correspond to "first sensor", and the detection sensors S3, S6 correspond to "second sensor". In other words, the detection sensors S1 to S10 include the detection sensors S1, S2, S4 and S5 as a first sensor, and detection sensors S3, S6 as a second sensor. The detection sensors S1, S2, S4 and S5 include two right detection sensors S1, S2, and two left detection sensors S4, S5. The detection sensors S3, S6 include one right detection sensor S3 and one left detection sensor S6.

The communication controller CN is connected to the detection sensors S1 to S10. The communication controller CN is capable of communicating with the terminal M via a network 20, and configured to transmit the measurement values P1 to P10 of pressure acquired by the detection sensors S1 to S10, to the terminal M. The communication controller CN is located, for example, on an undersurface of the seat bottom CA, in the backrest CB, or in other positions. The network 20 includes, for example, the Internet, LAN (Local Area Network), etc. Communications established between the communication controller CN and the terminal M via the network 20 may be a wireless communication, and/or a cable communication.

Figure 15:
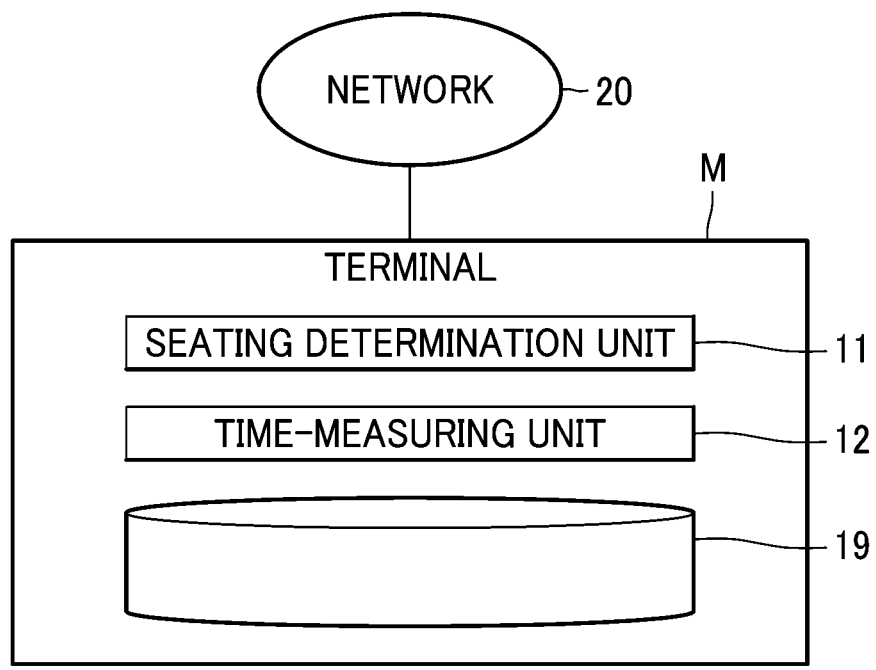
FIG. 15 is a block diagram of the seat experiencing system according to the second embodiment.

The terminal M is a computer comprising a CPU, a ROM, a RAM, etc. Specifically, the terminal M is, for example, a personal computer, a tablet computer, a smartphone, etc. The terminal M includes a display DSP. As shown in FIG. 15, the terminal M includes a seating determination unit 11, a time-measuring unit 12, and a storage unit 19. The storage unit 19 stores data necessary for computation and processing. The terminal M implements the functions of the seating determination unit 11 or the like by installing and executing predetermined programs.

The seating determination unit 11 makes a determination, based on detection results of the detection sensors S1 to S10, as to whether or not a person has got seated on the seat body C0. Specifically, in the present embodiment, based on the detection results of the detection sensors S1 to S6, the seating determination unit 11 determines that a person has got seated on the seat body C0 (hereinafter referred to also as "sitting"), and determines that a person has risen from the seat body C0 (hereinafter referred to also as "rising").

The seating determination unit 11 determines that a person has got seated on the seat body C0, on condition that the person seated on the seat body C0 has been detected by the detection sensors S1, S2, S4 and S5, and the person seated on the seat body C0 has been detected by the detection sensors S3, S6. To be specific, the seating determination unit 11 determines that a person has got seated on the seat body C0, on condition that each of the measurement values P1, P2, P4 and P5 from the detection sensors S1, S2, S4 and S5 has become equal to or greater than a corresponding first sitting threshold Pth1 and each of the measurement values P3, P6 from the detection sensors S3, S6 has become equal to or greater than a corresponding second sitting threshold Pth2.

To be more specific, in the present embodiment, the seating determination unit 11 determines that a person has got seated on the seat body C0 when a second time period T2 has elapsed from a time at which the person seated on the seat body C0 has been detected by the detection sensors S1, S2, S4 and S5 and the person seated on the seat body C0 has been detected by the detection sensors S3, S6. Specifically, the seating determination unit 11 determines that a person has got seated on the seat body C0 when the second time period T2 has elapsed from a time at which the respective measurement values P1, P2, P4 and P5 have become equal to or greater than the corresponding first sitting thresholds Pth1 and the respective measurement values P3, P6 have become equal to or greater than the corresponding second sitting thresholds Pth2.

The second time period T2 is a preset time period which is stored in the storage unit 19. The second time period T2 is set, for example, at a period of time that will have elapsed from a time at which each of the measurement values P1 to P6 has become equal to or greater than the corresponding sitting threshold Pth1, Pth2 to a time at which the person has assumed a complete sitting posture.

The first sitting threshold Pth1 and the second sitting threshold Pth2 are preset threshold values which are stored in the storage unit 19. The first sitting threshold Pth1 and the second sitting threshold Pth2 may be the same value, or may be different values. The first sitting threshold Pth1 may be the same value for all the detection sensors S1, S2, S4 and S5, or may be a different value for each of the detection sensors S1, S2, S4 and S5. The same can be said for the second sitting threshold Pth2. To give an example, the first sitting thresholds Pth1 and the second sitting thresholds Pth2 are all set at 10.

On the other hand, the seating determination unit 11 determines that a person has risen from the seat body C0, on condition that the person seated on the seat body C0 has become undetected by the detection sensors S1, S2, S4 and S5 and the person seated on the seat body C0 has become undetected by the detection sensors S3, S6. Specifically, the seating determination unit 11 determines that a person has risen from the seat body C0, on condition that each of the measurement values P1, P2, P4 and P5 from the detection sensors S1, S2, S4 and S5 has become equal to or smaller than a corresponding first rising threshold Pth3 and each of the measurement values P3, P6 from the detection sensors S3, S6 has become equal to or smaller than a corresponding second rising threshold Pth4.

The first rising threshold Pth3 and the second rising threshold Pth4 are preset threshold values which are stored in the storage unit 19. The first rising threshold Pth3 is a value smaller than the first sitting threshold Pth1, and the second rising threshold Pth4 is a value smaller than the second sitting threshold Pth2. The first rising threshold Pth3 and the second rising threshold Pth4 may be the same value, or may be different values. The first rising threshold Pth3 may be the same value for all the detection sensors S1, S2, S4 and S5, or may be a different value for each of the detection sensors S1, S2, S4 and S5. The same can be said for the second rising threshold Pth4. To give an example, the first rising thresholds Pth3 and the second rising thresholds Pth4 are all set at 5.

In this embodiment, the seating determination unit 11 determines that a person has risen from the seat body C0 when a first time period T1 has elapsed from a time at which the person seated on the seat body C0 has become undetected by the detection sensors S1, S2, S4 and S5 and the person seated on the seat body C0 has become undetected by the detection sensors S3, S6. Specifically, the seating determination unit 11 determines that a person has risen from the seat body C0 when the first time period T1 has elapsed from a time at which the respective measurement values P1, P2, P4 and P5 have become equal to or smaller than the corresponding first rising thresholds Pth3 and the respective measurement values P3, P6 have become equal to or smaller than the corresponding second rising thresholds Pth4.

The first time period T1 is a preset time period which is stored in the storage unit 19. The first time period T1 is set, for example, at a period of time that will have elapsed from a time at which each of the measurement values P1 to P6 has become equal to or smaller than the corresponding rising threshold Pth3, Pth4 to a time at which the person has assumed a complete standing posture. The first time period T1 and the second time period T2 may be the same or different.

The time-measuring unit 12 measures time based on a result of a determination made by the seating determination unit 11. Specifically, the time-measuring unit 12 starts measurement of time at a time when the seating determination unit 11 has determined that a person has risen from the seat body C0, and ends the measurement of time at a time when a person has got seated again on the seat body C0 and the seating determination unit 11 has determined that the person has got seated. Then, the time-measuring unit 12 determines by calculation an elapsed time T, i.e., a time which has elapsed from the time of starting the measurement of time to the time of ending the time measurement of time. Specifically, the time-measuring unit 12 determines the elapsed time T by calculation based on the time of starting the measurement of time and the time of ending the measurement of time. The time-measuring unit 12 presents the result of determination, i.e., the determined elapsed time T, on the display DSP of the terminal M.

The seat experiencing system SYS2 of this embodiment may be utilized, for example, for measurements for TUG test (Timed Up and Go Test). The TUG test is a test for evaluating a physical function of an aged person, or the like, by measuring time of motion of rising from a chair, walking 3 meters to and turning around a mark (pylon), and walking back to and getting seated on the chair again. When the seat experiencing system SYS2 of the present embodiment is used for the TUG test, the time it takes to go through with the motion starting from rising from a chair until getting seated on the chair again, can be measured without using a stopwatch.

Next, one example of a process executed by the terminal M in the second embodiment will be described below.

Figure 16:
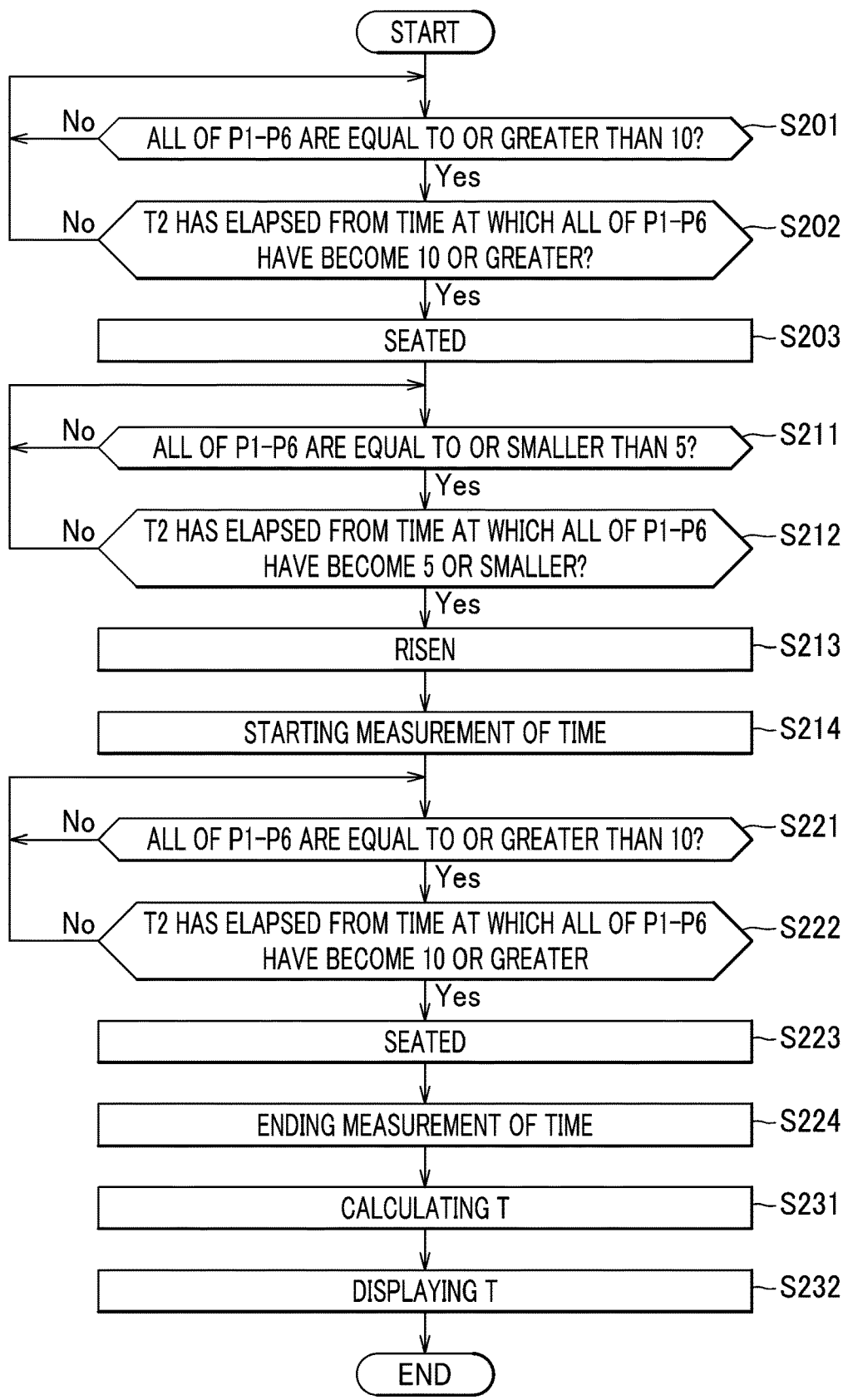
FIG. 16 is a flowchart showing one example of a process of a terminal according to the second embodiment.

In this embodiment, the terminal M makes a determination as to whether or not any person is seated on the seat body C0. Specifically, as shown in FIG. 16, a determination is made as to whether or not all of the measurement values P1 to P6 from the detection sensors S1 to S6 are equal to or greater than 10 (sitting threshold: Pth1, Pth2) (S201). If all the measurement values P1 to P6 are equal to or greater than the sitting threshold (=10) (Yes, S201), then the terminal M makes a determination as to whether or not the second time period T2 has elapsed from a time at which all the measurement values P1 to P6 have become equal to or greater than the sitting threshold (=10) (S202). When the second time period T2 has elapsed from a time at which all the measurement values P1 to P6 have become equal to or greater than the sitting threshold (=10) (Yes, S202), then the terminal M determines that a person is (has got) seated on the seat body C0 (S203).

Next, the terminal M makes a determination as to whether or not all of the measurement values P1 to P6 are equal to or smaller than 5 (rising threshold: Pth3, Pth4) (S211). If all the measurement values P1 to P6 are equal to or smaller than the rising threshold (=5) (Yes, S211), then the terminal M makes a determination as to whether or not the first time period T1 has elapsed from a time at which all the measurement values P1 to P6 have become equal to or smaller than the rising threshold (=5) (S212). When the first time period T1 has elapsed from a time at which all the measurement values P1 to P6 have become equal to or smaller than the rising threshold (=5) (Yes, S212), then the terminal M determines that the person has risen (S213), and starts measurement of time (S214).

Next, the terminal M makes a determination as to whether or not all of the measurement values P1 to P6 are equal to or greater than the sitting threshold (=10) (S221). If all the measurement values P1 to P6 are equal to or greater than the sitting threshold (=10) (Yes, S221), then the terminal M makes a determination as to whether or not the second time period T2 has elapsed from a time at which all the measurement values P1 to P6 have become equal to or greater than the sitting threshold (=10) (S222). When the second time period T2 has elapsed from a time at which all the measurement values P1 to P6 have become equal to or greater than the sitting threshold (=10) (Yes, S222), then the terminal M determines that a person has got seated on the seat body C0 (S223), and ends the measurement of time (S224).

Thereafter, the terminal M determines an elapsed time T by calculation (S231), presents the determined elapsed time T on the display DSP (S232), and brings the process to an end.

With the second embodiment described above, in which a plurality of the detection sensors S1 to S6 are used to detect sit-down and rise-up motions, the sit-down and rise-up motions can be detected precisely.

Since the detection sensors S1, S2, S4 and S5 are located in positions corresponding to the buttocks of an occupant, and the detection sensors S3, S6 are located in positions corresponding to the thighs of the occupant, the detection sensors S1 to S6 are located in positions on which high pressure is exerted when a person is seated on the seat body C0. Accordingly, the sit-down and rise-up motions can be detected more precisely by using the detection sensors S1 to S6.

Since the detection sensors S1, S2, S4 and S5 corresponding to the buttocks of an occupant are located two at the right and the other two at the left, and the detection sensors S3, S6 corresponding to the thighs of the occupant are located one at the right and the other at the left, arrangement of the increased number of sensors makes it possible to detect the sit-down and rise-up motions more precisely.

Since the sit-down and rise-up motions can be detected precisely, a period of time that has elapsed from a time at which a person has risen from the seat body C0 to a time at which a person has got seated on the seat body C0 can be measured precisely in the time-measuring unit 12.

Since the seating determination unit 11 determines that a person has risen up, when the first time period T1 has elapsed from a time at which all the measurement values P1 to P6 from the detection sensors S1 to S6 have become equal to or smaller than 5 (rising threshold: Pth3, Pth4), a determination that a person has risen from the seat body C0 is not made until the person has assumed a complete standing posture. Therefore, the rise-up motion can be detected more precisely.

Since the seating determination unit 11 determines that a person has got seated, when the second time period T2 has elapsed from a time at which all the measurement values P1 to P6 from the detection sensors S1 to S6 have become equal to or greater than 10 (sitting threshold: Pth1, Pth2), a determination that a person has got seated on the seat body C0 can be made after the person has assumed a complete sitting posture. Therefore, the sit-down motion can be detected more precisely.

The seat experiencing system SYS2 configured according to the second embodiment may be utilized, for example, for a game of competition for the time it takes to go through with a series of motions starting from rising from the seat body C0, walking several meters to and around a mark, and walking back to the seat body C0 and getting seated on the seat body C0 again. Such a game may be configured to start a countdown when the game is started by launching an application program for that game at the terminal M while the seat body C0 has a person seated thereon, and to start measurement of time in response to the motion of the person rising from the seat body C0 as prompted at a time when the count reaches zero.

An alternative configuration may be such that the game is started by launching an application program for that game at the terminal M, then a person gets seated on the seat body C0, and a countdown is started, for example, at the expiry of five-sec. period of time that has elapsed after a time at which the measurement values P1 to P6 from the detection sensors S1 to S6 have become equal to or greater than 10 (sitting threshold: Pth1, Pth2).

Another alternative configuration may be such that the measurement of time is started at a time when the count reaches zero, whereas the measurement of time is ended when a person having risen from the seat body C0 and walked around the mark and back thereto gets seated on the seat body C0 again (i.e., at a time of detection of the sitting motion).

In addition, if the measurement values P1 to P6 have become equal to or smaller than 10 (sitting threshold) before the count reaches zero, a message which reads "FALSE START" may be shown on the display DSP of the terminal M.

Next, a third embodiment will be described below. In describing the third embodiment, and a fourth embodiment which will follow later, for example, elements having substantially the same configurations as those of the second embodiment will be designated by the same reference characters, and a description thereof will be omitted.

Figure 17:
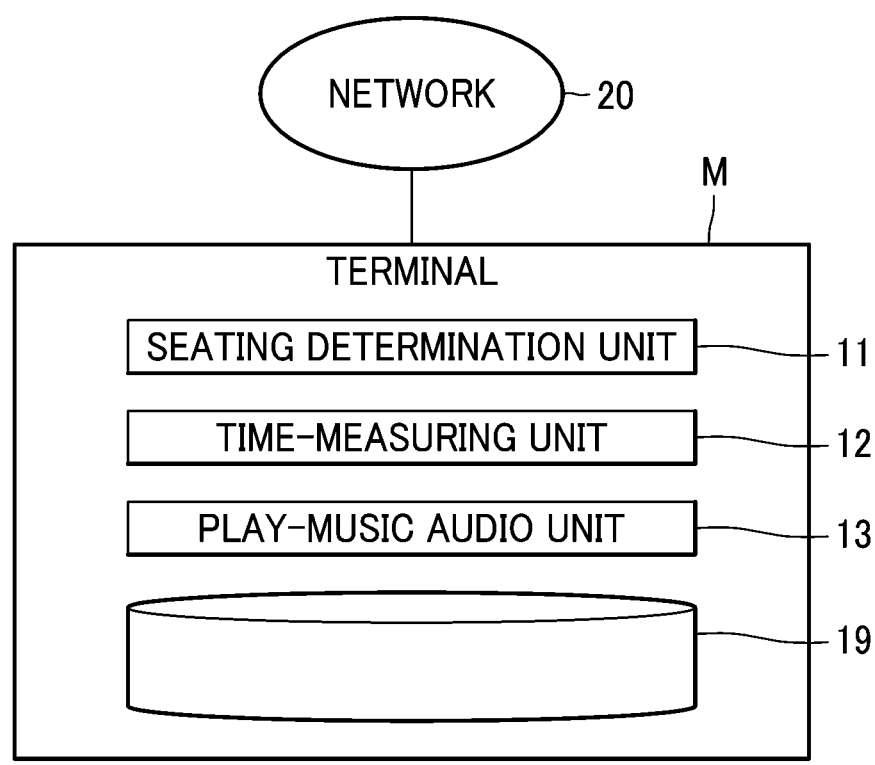
FIG. 17 is a block diagram of a seat experiencing system according to a third embodiment.

As shown in FIG. 17, the terminal M comprises a seating determination unit 11, a time-measuring unit 12, a play-music audio unit 13, and a storage unit 19.

The seating determination unit 11 determines that a person has got seated, when each of the measurement values P1, P2, P4 and P5 from the detection sensors S1, S2, S4 and S5 has become equal to or greater than a corresponding first sitting threshold Pth1, and each of the measurement values P3, P6 from the detection sensors S3, S6 has become equal to or greater than a corresponding second sitting threshold Pth2. On the other hand, the seating determination unit 11 determines that the person has risen up, when the first time period T1 has elapsed from a time at which the respective measurement values P1, P2, P4 and P5 have become equal to or smaller than the corresponding first rising thresholds Pth3 and the respective measurement values P3, P6 have become equal to or smaller than the corresponding second rising thresholds Pth4.

The time-measuring unit 12 starts measurement of time (sitting time period Ts) at a time when the seating determination unit 11 has determined that a person has got seated on the seat body. Thereafter, the time-measuring unit 12 executes a predetermined operation for prompting the person seated on the seat body C0 to rise up after a lapse of a predetermined time period Tsth from the time of starting the measurement of the sitting time period Ts. The predetermined operation is an operation of producing a predetermined sound, which includes music. In the present embodiment, the predetermined operation is an operation of playing music. That is, the time-measuring unit 12 causes the play-music audio unit 13 to play music at a time when the sitting time period Ts has become the predetermined time period Tsth or longer.

The predetermined time period Tsth is, for example, 30 minutes, or one hour. It is to be understood that the predetermined time period Tsth may be arbitrarily set by a user using the seat experiencing system SYS2.

After executing the predetermined operation, the time measuring unit 12 stops the predetermined operation at a time when the seating determination unit 11 has determined that the person has risen up. To be specific, if the seating determination unit 11 has determined that the person has risen up after the time-measuring unit 12 causes the play-music audio unit 13 to play music, then the time-measuring unit 12 causes the play-music audio unit 13 to stop playing music.

On the other hand, after the seating determination unit 11 has determined that a person has got seated and before the sitting time period Ts has become the predetermined time period Tsth or longer, the time-measuring unit 12 does not execute the predetermined operation (of playing music) when the seating determination unit 11 has determined that the person has risen up. In this occasion, the time-measuring unit 12 resets the sitting time period Ts to 0.

The seat experiencing system SYS2 of this embodiment may be used as a system for preventing a person from remaining seated on the seat body C0 for a long time, and/or for informing a person seated on the seat body C0 that a specific time has come.

Next, one example of a process executed by the terminal M in the third embodiment will be described below.

Figure 18:
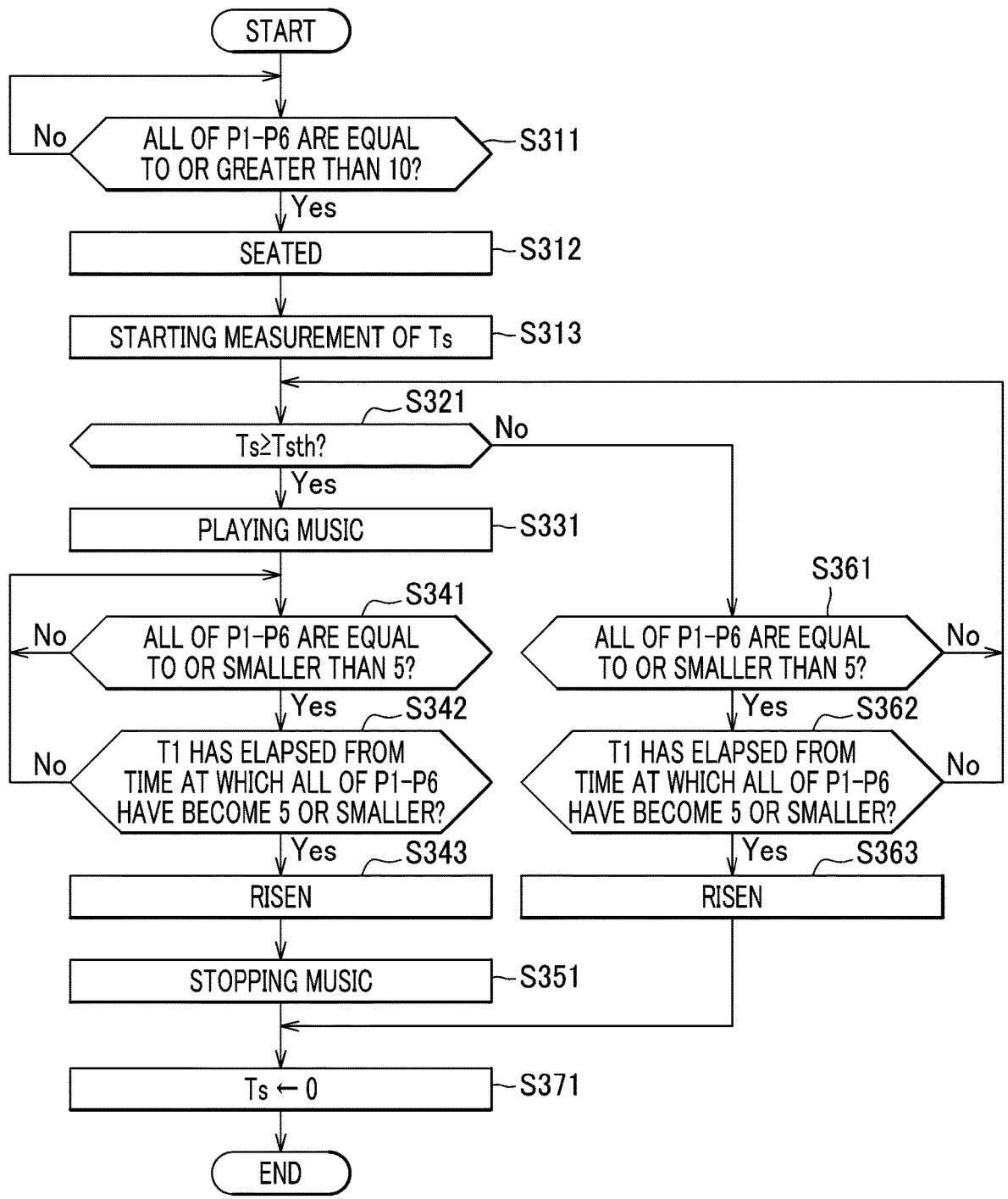
FIG. 18 is a flowchart showing one example of a process of a terminal according to the third embodiment.

As shown in FIG. 18, the terminal M makes a determination as to whether or not all of the measurement values P1 to P6 from the detection sensors S1 to S6 are equal to or greater than 10 (sitting threshold: Pth1, Pth2) (S311). If all the measurement values P1 to P6 are equal to or greater than the sitting threshold (=10) (Yes, S311), then the terminal M determines that a person has got seated (S312), and starts measurement of a sitting time period Ts (S313).

Next, the terminal M makes a determination as to whether or not the sitting time period Ts is equal to or longer than the predetermined time period Tsth (S321). If the sitting time period Ts has become equal to or longer than the predetermined time period Tsth (Yes, S321), then the terminal M plays music (S331).

Next, the terminal M makes a determination as to whether or not all of the measurement values P1 to P6 are equal to or smaller than 5 (rising threshold: Pth3, Pth4) (S341). If all the measurement values P1 to P6 are equal to or smaller than the rising threshold (=5) (Yes, S341), then the terminal M makes a determination as to whether or not the first time period T1 has elapsed from a time at which all the measurement values P1 to P6 have become equal to or smaller than the rising threshold (=5) (S342). When the first time period T1 has elapsed from a time at which all the measurement values P1 to P6 have become equal to or smaller than the rising threshold (=5) (Yes, S342), then the terminal M determines that the person has risen (S342), and stops playing music (S351).

Thereafter, the terminal M resets the sitting time period Ts (S371), and brings the process to an end.

On the other hand, before the sitting time period Ts has become the predetermined time period Tsth or longer (No, S321), if all the measurement values P1 to P6 are equal to or smaller than the rising threshold (=5) (Yes, S361), then the terminal M makes a determination as to whether or not the first time period T1 has elapsed from a time at which all the measurement values P1 to P6 have become equal to or smaller than the rising threshold (=5) (S362). When the first time period T1 has elapsed from a time at which all the measurement values P1 to P6 have become equal to or smaller than the rising threshold (=5) (Yes, S362), then the terminal M determines that the person has risen (S363), and thus does not play music, but rather resets the sitting time period Ts (S371) and brings the process to an end.

With the third embodiment described above, as with the case of the second embodiment, since a plurality of the detection sensors S1 to S6 are used to detect sit-down and rise-up motions, the sit-down and rise-up motions can be detected precisely.

Since the sit-down and rise-up motions can be detected precisely, a period of time (sitting time period Ts) that has elapsed from a time at which a person has got seated on the seat body C0 can be measured precisely. Accordingly, the predetermined operation (of playing music) can be executed with precise timing. The person seated on the seat body is thus prompted by the executed predetermined operation to rise up, and can be prevented from remaining seated over an extended period of time.

In describing the third embodiment, an operation of playing music is taken as an example of the predetermined operation, but the predetermined operation is not limited thereto. For example, the predetermined operation may be an operation of producing a sound other than music, for example, a voice for prompting a person to rise up, an alarm, a sound of the ocean wave, a sound of the murmur of a brook, a song of a bird, etc. The predetermined operation is not limited to an operation of producing a sound; other examples may include an operation of vibrating the seat body by operating a vibration generating device provided in the seat body. Furthermore, the predetermined operation to be executed may not be limited to a single operation; a plurality of operations may be executed. For example, the operation of producing a predetermined sound and the operation of vibrating the seat body may be executed at the same time.

The seat experiencing system SYS2 configured according to the third embodiment may be utilized, for example, for a game of competition for the number of times music has been played within a unit time e.g., three minutes. In this example, the predetermined time period Tsth may be set at 10 seconds. When the game is started by launching an application program for the game at the terminal M, a user gets seated on the seat body C0. By doing so, music is played after 10 seconds, and the user in response thereto rises from the seat body C0 to thereby stop the music. The quicker the user's sit-down and rise-up motions, the more times music can be played within the unit time.

Next, a fourth embodiment will be described below.

As shown in FIG. 15, the terminal M comprises a seating determination unit 11, a time-measuring unit 12, and a storage unit 19.

The seating determination unit 11 determines that a person has got seated, when each of the measurement values P1, P2, P4 and P5 from the detection sensors S1, S2, S4 and S5 has become equal to or greater than a corresponding first sitting threshold Pth1, and each of the measurement values P3, P6 from the detection sensors S3, S6 has become equal to or greater than a corresponding second sitting threshold Pth2. On the other hand, the seating determination unit 11 determines that the person has risen up, when each of the measurement values P1, P2, P4 and P5 has become equal to or smaller than a corresponding first rising threshold Pth3 and each of the measurement value P3, P6 has become equal to or smaller than a corresponding second rising thresholds Pth4.

The time-measuring unit 12 starts measurement of time at a time when the seating determination unit 11 has determined that a person has got seated, and ends the measurement of time at a time when the seating determination unit 11 has determined that a person has risen up. The time-measuring unit 12 then determines, by calculation, an elapsed time T that has elapsed from the time of starting the measurement of time to the time of ending the measurement of time.

The seat experiencing system SYS2 configured according to the present embodiment may be utilized for measurement of a sitting time period for a person seated on the seat body C0. The seat experiencing system SYS2 configured according to the present embodiment may be utilized like a stopwatch.

Next, one example of a process executed by the terminal M in the fourth embodiment will be described below.

Figure 19:
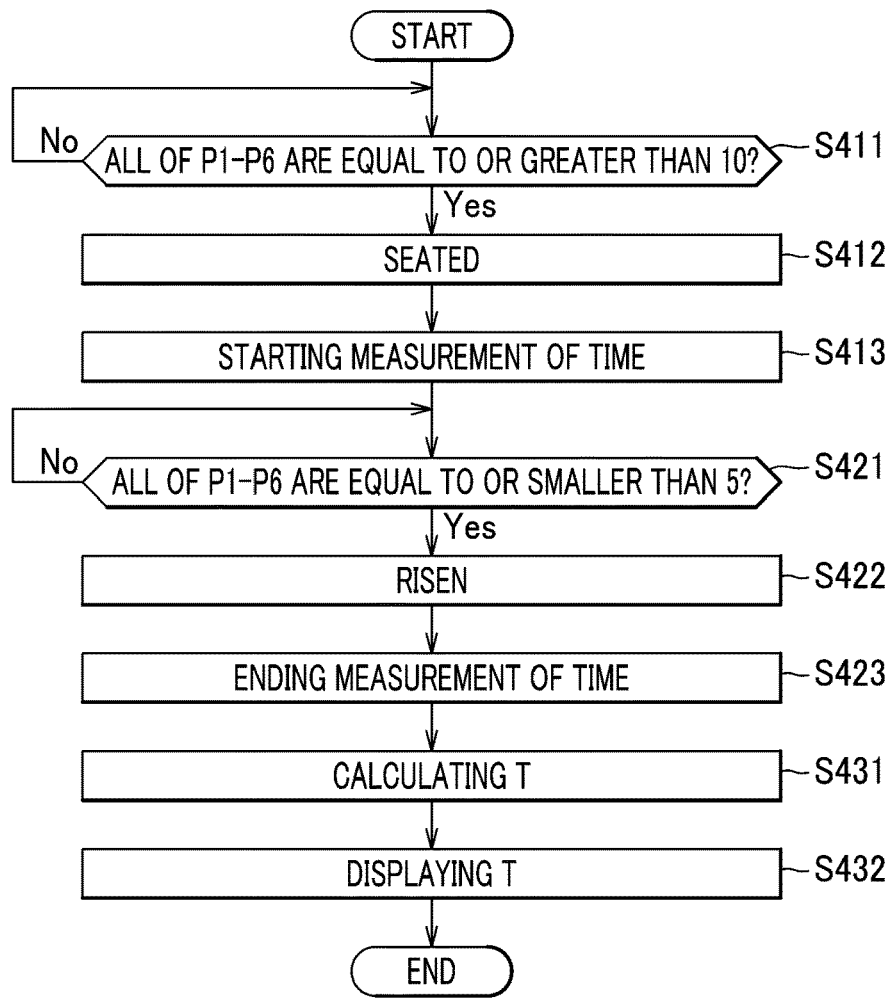
FIG. 19 is a flowchart showing one example of a process of a terminal according to a fourth embodiment.

As shown in FIG. 19, the terminal M makes a determination as to whether or not all of the measurement values P1 to P6 from the detection sensors S1 to S6 are equal to or greater than 10 (sitting threshold: Pth1, Pth2) (S411). If all the measurement values P1 to P6 are equal to or greater than the sitting threshold (=10) (Yes, S411), then the terminal M determines that a person has got seated (S412), and starts measurement of time (S413).

Next, the terminal M makes a determination as to whether or not all of the measurement values P1 to P6 are equal to or smaller than 5 (rising threshold: Pth3, Pth4) (S421). If all the measurement values P1 to P6 are equal to or smaller than the rising threshold (=5) (Yes, S421), then the terminal M determines that the person has risen up (S422), and ends the measurement of time (S423).

Thereafter, the terminal M determines an elapsed time T by calculation (S431), presents the determined elapsed time T on the display DSP (S432), and brings the process to an end.

With the fourth embodiment described above, as with the cases of the second embodiment and the third embodiment, a plurality of the detection sensors S1 to S6 are used to detect sit-down and rise-up motions; therefore, the sit-down and rise-up motions can be detected precisely.

Since the sit-down and rise-up motions can be detected precisely, a period of time that has elapsed from a time at which a person has got seated on the seat body C0 to a time at which the person has risen from the seat body C0 can be measured precisely.

Although the second embodiment, the third embodiment, and the fourth embodiment have been described above, specific configurations thereof may be modified where deemed appropriate, and implemented as will be described below by way of example.

Figure 20:
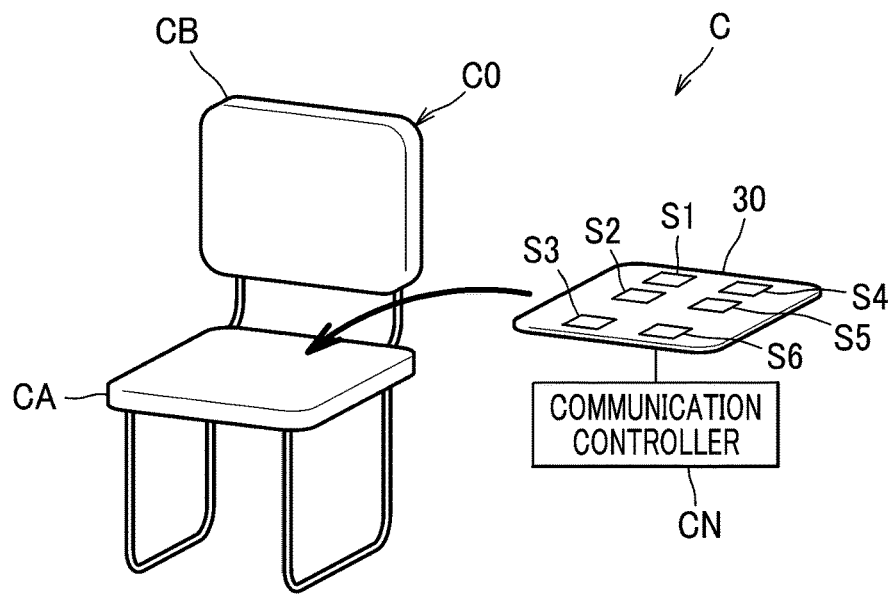
FIG. 20 is a diagram showing a modified example of a seat.

For example, the embodiments above are illustrated by a specific configuration in which the detection sensors S1 to S6 are provided at the seat bottom CA of the seat body C0, but are not limited to this configuration, and may be implemented in an alternative configuration in which such a detection sensor is not provided at the seat body itself. To be more specific, as shown in FIG. 20, the seat experiencing system (seat C) may comprise a seat body C0 and a cushion 30 to be placed on the seat bottom CA of the seat body C0, and may be configured to include detection sensors S1 to S6 provided at the cushion 30.

With this configuration, even if the seat body C0 itself has no detection sensor provided thereat, the seat experiencing system can be implemented by placing the cushion 30 with the detection sensors S1 to S6, on the seat bottom CA. Accordingly, the seat experiencing system can be introduced easily, for example, by placing the cushion with a detection sensor on the seat bottom of an existing chair.

Although the seat experiencing system SYS2 of the above-described embodiments includes a single seat C and a terminal M, this is not a prerequisite. For example, the seat experiencing system may comprise a plurality of seats and a terminal. That is, the terminal of the seat experiencing system may be configured to be connected to and capable of communicating with the plurality of seats, to acquire detection results of the sensors from respective seats for detection of the sit-down and rise-up motions, and measurement of time, etc.

In the above-described embodiments, the seating determination unit 11 is provided separately from the seat body C0, but this is not a prerequisite. For example, a seating determination unit may be provided, like the sensor, at the seat body C0. In other words, the seat experiencing system may be configured to comprise a seat which includes a seat body, a sensor, and a seating determination unit. The same can be said for the time-measuring unit, and other elements.

In the above-described embodiments, the detection sensors S1, S2, S4 and S5 as a first sensor include two right detection sensors S1, S2 and two left detection sensors S4, S5, but this is not a prerequisite. For example, the number of sensors as the first sensor provided at the right may be one, three, or more. The same can be said for the number of sensors as the first sensor provided at the left. Moreover, the number of the right first sensors and the number of the left first sensors may be different from each other.

In the above-described embodiments, the detection sensors S3, S6 as a second sensor include one right detection sensor S3 and one left detection sensor S6, but this is not a prerequisite. For example, the number of sensors as the second sensor provided at the right may be two, or more. The same can be said for the number of sensors as the second sensor provided at the left. Moreover, the number of the right second sensors and the number of the left second sensors may be different from each other.

In the above-described embodiments, only the detection sensors S1 to S6 provided at the seat bottom CA are used to detect the sit-down and rise-up motions, but this is not a prerequisite. For example, the both of the detection sensors S1 to S6 provided at the seat bottom CA and the detection sensors S7 to S10 provided at the backrest CB may be used to detect the sit-down and rise-up motions.

In the above-described embodiments, the both of the first detection sensor and the second detection sensor are located at the seat bottom of the seat body, but this is not a prerequisite. For example, the first sensor and the second sensor may be located respectively at the seat bottom and at the backrest. By way of example, the first sensor may be located in a position corresponding to the buttocks of an occupant, and the second sensor may be located in a position corresponding to the waist of the occupant.

In the above-described embodiments, the detection sensors S1 to S10 are each configured as a pressure sensor, but not limited thereto, and may be configured as a capacitance sensor, an optical sensor, or the like. Moreover, in the above-described embodiments, the pressure sensor (a single kind of sensor) only is used to detect the sit-down and rise-up motions, but this is not a prerequisite; two or more kinds of sensors (e.g., pressure sensor and optical sensor) may be used to detect the sit-down and rise-up motions. It is also to be understood that any sensor other than a sensor for detecting a person seated on the seat body may be provided at the seat body.

In the above-described embodiments, the seat body C0 comprises a seat bottom CA and a backrest CB, but this is not a prerequisite. For example, the seat body may further comprise a headrest and/or an armrest in addition to the seat bottom and the backrest. Moreover, the seat body may, for example, comprise a seat bottom only, and may not comprise a backrest.

Any of the elements explained in relation to the second embodiment, third embodiment, fourth embodiment and their modified examples may be implemented in combination as desired.

Figure 21:
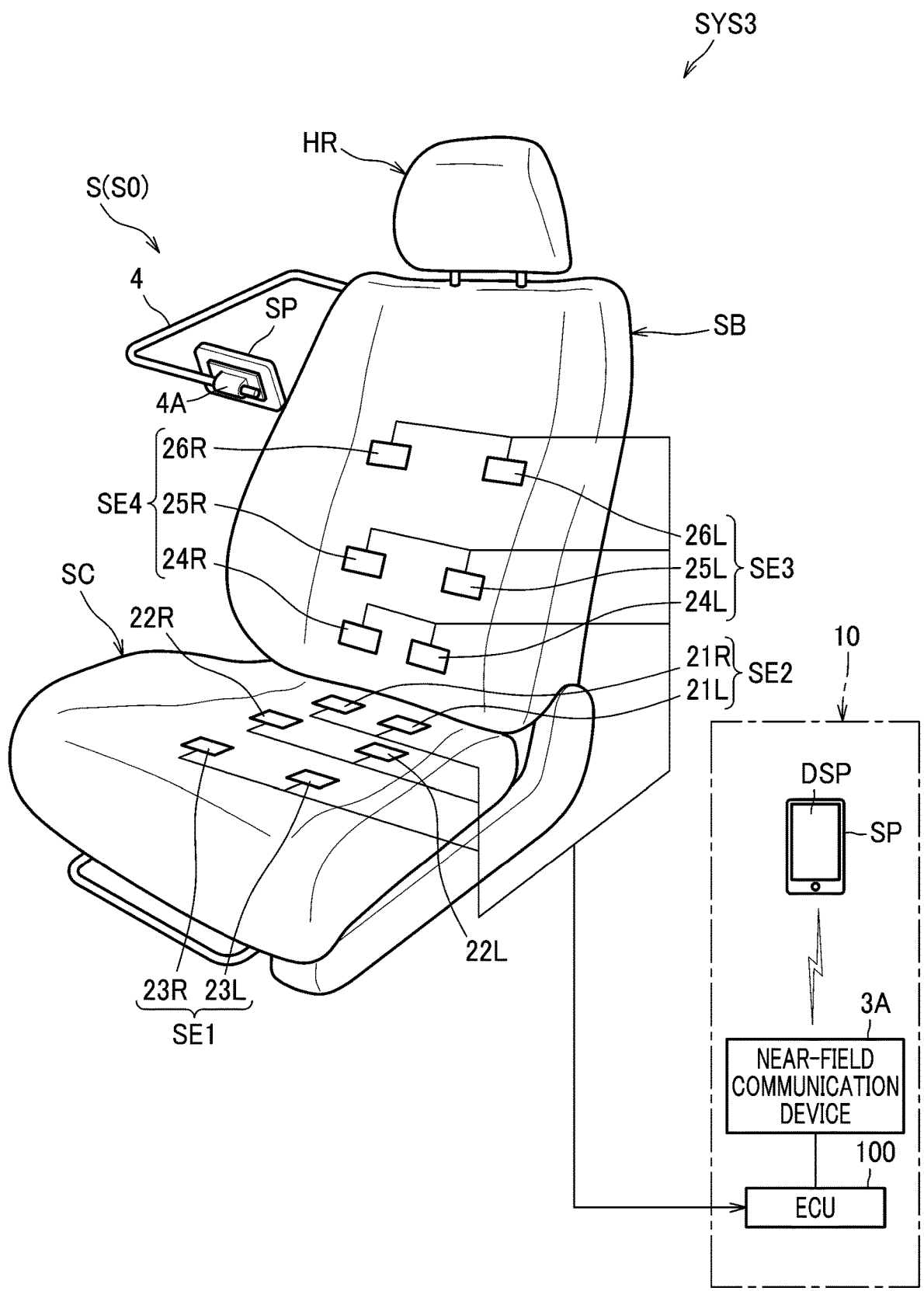
FIG. 21 is a diagram showing a seat experiencing system according to a fifth embodiment.

Next, a fifth embodiment will be described in detail with reference made to the drawings where appropriate. As shown in FIG. 21, a seat experiencing system SYS3 of this embodiment is configured to comprise a seat S and an in-seat experience device 10.

The seat S is a seat installed, for example, in a lounge of nursing-care facilities or the like, in a manner shareable among a plurality of users. The seat S includes a seat body S0 and pressure sensors 21 to 26 as a sensor. The seat body S0 includes a seat cushion SC, a seat back SB, and a headrest HR. The seat cushion SC and the seat back SB have an outer covering under which a plurality of pressure sensors 21 to 26 are provided. The pressure sensors 21 to 26 are sensors that acquire numeric values for use in detection of a physical state of a user on the seat body S0.

The pressure sensors 21 to 26 are so arranged as to be capable of detecting a state of a seat surface facing a user seated on the seat body S0, to acquire values of pressure from the user seated on the seat body S0. In other words, the pressure sensors 21 to 26 acquire pressure values corresponding to a physical state (specifically, a posture) of a user on the seat body S0. An ECU (Electronic Control Unit) 100 is a device that controls an operation (e.g., of a motor for an electrically powered reclining mechanism, a heater, etc.) of the seat body S0, and is connected to the pressure sensors 21 to 26 and thereby allowed to acquire measurement values from the respective pressure sensors 21 to 26.

The pressure sensors 21 to 26 are provided in pairs, i.e., each located left and right, symmetric with respect to a laterally central position of the seat S. In the following description and drawings which will be referred to below, pressure sensors 21 to 26 located on the left side may be designated by reference characters with "L" appended thereto, and pressure sensors 21 to 26 located on the right side may be designated by reference characters with "R" appended thereto, so that distinctions are drawn therebetween.

In the seat cushion SC, the pressure sensors 21 to 23 are provided.

The pressure sensors 21 are provided in positions corresponding to the lowermost portions of ischial bones of the user. On these positions, the load of the user is borne largest.

The pressure sensors 22 are located a little frontward of the pressure sensors 21.

The pressure sensors 21 and the pressure sensors 22 are provided so that each pair of the pressure sensors 21, 22 measures the pressure from the buttocks of the user, and only one pair may be provided.

The pressure sensors 23 are located frontward of and distanced far from the pressure sensors 21 and the pressure sensors 22. The pressure sensors 23 are located under the thighs of the user, and capable of determining values of pressure from the thighs of the user.

In the seat back SB, the pressure sensors 24 to 26 are provided. The pressure sensors 24 are provided in positions corresponding to the back of the waist of the user.

The pressure sensors 25 are located in positions a little higher than the positions of the pressure sensors 24.

The pressure sensors 24 and the pressure sensors 25 are provided so that each pair of the pressure sensors 24, 25 measures the pressure from the waist of the user, and only one pair may be provided.

The pressure sensors 26 are located above and distanced far from the pressure sensors 24 and the pressure sensors 25. The pressure sensors 26 are located in positions corresponding to the upper region of the back of the user, and capable of determining values of pressure from the upper region of the back of the user.

In the present embodiment, the seat experiencing system SYS3 is configured to provide a 100-meter dash game using the pressure sensors 21 to 26. In this embodiment, the pressure sensors 21 to 26 also acquire measurement values for use in identifying motion of a user seated on the seat body S0. The 100-meter dash game is a game in which a user seated on the seat body S0 moves his/her legs up and down alternately to thereby cause a character shown on the display DSP as a screen of a smartphone SP to run.

The seat body S0 is provided with a holder 4 for holding a smartphone SP. The holder 4 is formed by bending a wire, with one end fixed to the seat back SB and the other end having a retaining portion 4A for the smartphone SP to be retained thereto. With the smartphone SP being retained to the retaining portion 4A, the user can see the display DSP of the smartphone SP without holding the smartphone SP by hand.

The in-seat experience device 10 is configured to comprise an ECU 100 and a smartphone SP as a terminal.

A near-field communication device 3A which enables near-field wireless communication, such as Bluetooth (registered trademark), Wi-Fi (registered trademark), etc. is connected to the ECU 100. The ECU 100 is connected to the pressure sensors 21 to 26. In the present embodiment, the ECU 100 and the near-field communication device 3A are provided at the seat body S0. The ECU transmits pressure values acquired from the pressure sensors 21 to 26 to the smartphone SP.

The ECU 100 and the smartphone SP each include a CPU, a ROM, a RAM, a rewritable nonvolatile memory, etc. (not shown), and are configured to execute pre-stored programs. The smartphone SP further includes the display DSP. The smartphone SP is configured to operate according to the program, and thus functions as a controller for executing the 100-meter dash game. The smartphone SP acquires the pressure values from the pressure sensors 21 to 26 via the ECU 100, and executes the 100-meter dash game based on the pressure values.

To be more specific, to execute the 100-meter dash game, the smartphone SP acquires the pressure values $P23_L$, $P23_R$ from the left and right pressure sensors 23L, 23R. Subsequently, the smartphone SP determines a normal pressure $P23_n$ that is an average pressure of the user currently seated thereon and a threshold value P23th for detection of peaks of pressure values, and computes a normal step cycle $TS_n$ that is an average of time intervals in each of which a sequence of motions of the legs of the user is completed.

Figure 22:
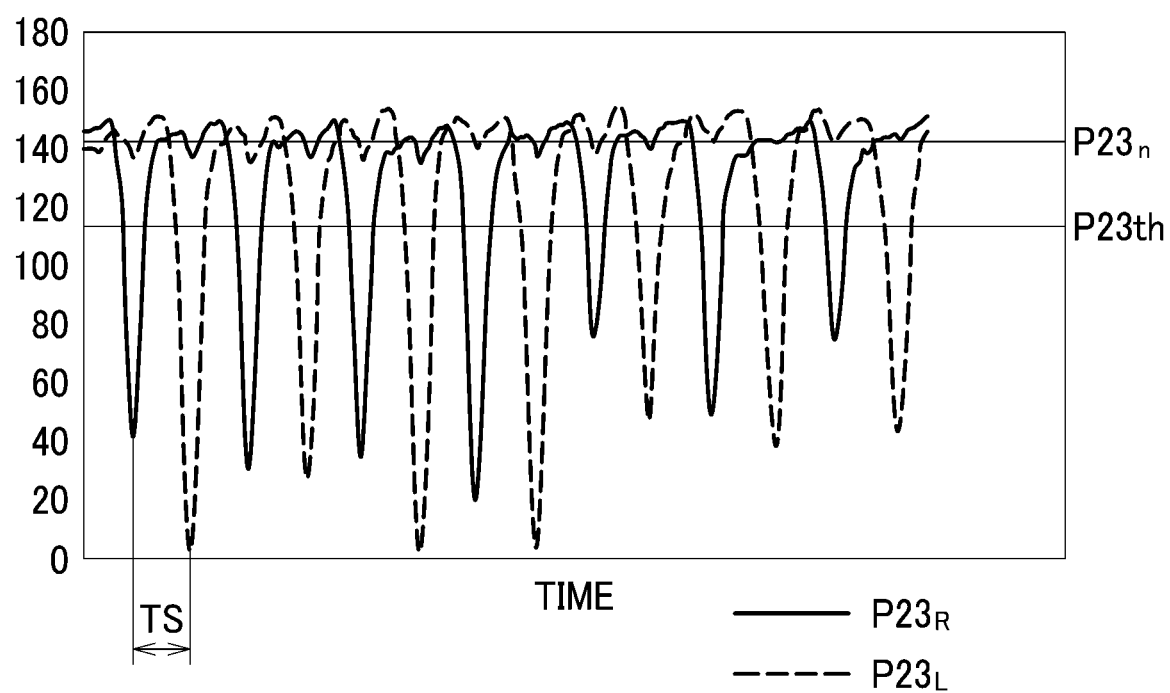
FIG. 22 is a graph showing change of pressure acquired for a 100-meter dash game.

Specifically, when a user lifts his/her legs alternately, the pressure values $P23_R$, $P23_L$ change as shown in FIG. 22, for example. In FIG. 22, a term in which the pressure goes down sharply indicates that the user has lifted his/her leg up and the pressure at an area detected by the pressure sensor 23 has become small accordingly. In fact, the pressure values that have not gone down but kept at about 140 will be reckoned as a normal pressure $P23n$ that is an average of pressure values detected when the legs are not lifted up. To compute the normal pressure $P23n$, for example, you may identify such absolute values as found not greater than a predetermined value (i.e., the values of which variations are small enough) among the absolute values of the differences between the last value and the present value of the pressure values $P23_R$, $P23_L$ (remainders each determined by subtraction of the last value $P23(n-1)$ from the present value $P23(n)$), and sum up and average the present values used to obtain the identified absolute values.

The threshold value $P23th$ is a threshold value for determining that the legs are currently being lifted up; for example, as is the case of FIG. 22, values ranging generally from 100 to 120 may be used. For this purpose, the threshold value $P23th$ may be a value obtained by multiplying the normal pressure $P23n$ by a predetermined value. For example, the value obtained by multiplying the normal pressure $P23n$ by a predetermined value ranging generally from 0.6 to 0.9 may be feasible for the threshold value $P23th$.

The normal step cycle $TS_n$ is an average value of the step cycle TS that is a time interval between peaks of the pressure values $P23_R$, $P23_L$.

Peak detection of the pressure values $P23_R$, $P23_L$ may be determined to occur when the difference between the last value and the present value changes from the negative to the positive under the condition that each pressure value $P23_R$, $P23_L$ is smaller than the threshold value $P23th$ (i.e., pressure value has crossed the threshold value from above to below), and the last value $P23(n-1)$ detected at this last time is assumed to be a peak value Pm.

Upon detection of each of peaks of the pressure values $P23_R$, $P23_L$ varying according to the motions of a user, the smartphone SP computes a peak value Pm, and then computes a step intensity F ($F_R$, $F_L$) that is a leg-lift motion scale based on the peak value Pm and the normal pressure $P23_n$. The step intensity F may be indicated by the magnitude of the peak, i.e., a value obtained by subtraction of the peak value Pm from the normal pressure $P23_n$. In this embodiment, the obtained value is normalized by the normal pressure $P23_n$ so as to eliminate variations caused by largeness of the build of a user. For example, the step intensity F may be given as follows:

$$F=(P23_n-Pm)/P23_n$$

The smartphone SP, which has computed the step intensity F during the 100-meter dash game, causes a character on the display DSP to move toward the finish line. The amount of locomotion in this operation is determined in accordance with the magnitude of the step intensity F. The smartphone SP may, for example, cause the character to move for a distance F [m] toward the finish line.

At the end of the 100-meter dash game, the smartphone SP obtains a clocking (a time taken when a finish line was crossed) as an execution result of the game. Herein, the clocking may be determined by starting measurement of time at the start of the 100-meter dash game, and ending the measurement of time when a value obtained by multiplying the step intensity F by the number of times of computation of the step intensity F has become equal to or greater than 100.

The smartphone SP is configured to be capable of storing records of the 100-meter dash game for each user, each record being associated with user identification information for each user. In the present embodiment, the user identification information includes a nickname of a user and a user ID. The nickname is a piece of information freely determined by a user when the user executes the 100-meter dash game for the first time. The user ID is associated with the nickname and recorded in the order of registration of the nickname. For example, supposing the users "A", "B", . . . "E" are registered with their nicknames "A", "B", . . . "E", in alphabetical order, the nickname "A" associated with a user ID "0001" is registered, and similarly, following user IDs are registered as, 0002: B, 0003: C, . . . , and 0005: E, respectively, in this order.

The smartphone SP is configured to be capable of displaying, on the screen, a plurality of pieces of user identification information corresponding to a plurality of users (see FIG. 29) before starting the 100-meter dash game. To be more specific, the smartphone SP is configured to be capable of displaying a pull-down menu in which the plurality of pieces of user identification information are listed downward on the screen.

Specifically, when the application (hereinafter referred to also as "app") for the 100-meter dash game is launched, the smartphone SP displays a start image shown in FIG. 27(a), on the screen. The start image includes a USER REGISTRATION button B11, a START button B12, and an EXIT button B13.

If a user presses the USER REGISTRATION button B11, then the smartphone SP displays a nickname entry image shown in FIG. 27(b), on the screen. If the user presses the START button B12, then the smartphone SP displays a pull-down menu shown in FIG. 29. If the user presses the EXIT button B13, then the smartphone SP exits the app for the 100-meter dash game.

The smartphone SP has a function of executing a registration process for registration of user identification information which comprises instructing a user to get seated and assume a predetermined posture on the seat S, and storing pressure values acquired from the plurality of pressure sensors 21 to 23, 25 and 26 while the user is assuming the predetermined posture on the seat body S0, as user pressure values specific to that user, for respective pressure sensors 21 to 23, 25 and 26. In the present embodiment, the pressure values from the pressure sensors 24 are not stored; it is however to be understood that the pressure values from the pressure sensors 24 may be stored. In the following description, the pressure sensors 21 to 23, 25 and 26 other than the pressure sensors 24 are also referred to as "subject pressure sensors".

The smartphone SP executes an acquisition process of acquiring user pressure values corresponding to the respective subject pressure sensors on a plurality of occasions, e.g., three times. Furthermore, the smartphone SP has a function of storing a numeric value range extended with predetermined margins allowed for the acquired user pressure value, as a screening range associated with the user identification information.

To be more specific, as shown in FIG. 23, the smartphone SP stores the user pressure values acquired in the first, second and third rounds of the acquisition process for each of the subject pressure sensors. In the drawing, for example, the user pressure values acquired in the first, second and third rounds of the acquisition process take on values of 1, 2 and 1 for the pressure sensor 25R, and take on values of 389, 271 and 280 for the pressure sensor 26R.

The smartphone SP has a function of storing a plurality of numeric value ranges each extended with predetermined margins allowed for the user pressure values corresponding to the respective subject pressure sensors, as a plurality of screening ranges associated with the user identification information. Hereafter, the plurality of screening ranges associated with the user identification information will be referred to also as "screening data". Specifically, the smartphone SP stores the screening data, of which the plurality of screening ranges are set by the following formula (0):

$$\mu \pm A \times \sigma \quad (0)$$

where μ is an arithmetic mean of the pressure values acquired on the three occasions of the acquisition process, σ is a standard deviation of the pressure values acquired on the three occasions of the acquisition process, and A is an arbitrary number (e.g., 2, in the present embodiment).

In the drawing, the average μ for the pressure sensor 25R is 1, μ+2σ is 3, and μ−2σ is 0. Accordingly, the screening range corresponding to the pressure sensor 25L is in the range of 0 to 3. Similarly, the screening range for each of the subject pressure sensors is set. For example, the screening range corresponding to the pressure sensor 26R is set at a range of 206 to 421.

The smartphone SP has a function of determining whether a criterion, which is satisfied if the user pressure value acquired from each of the plurality of subject pressure sensors when a user is on the seat body S0 falls within the screening range, is satisfied for each of the pieces of user identification information. The smartphone SP is configured to store a satisfied criterion number, that is the number of satisfied criteria, associated with the corresponding piece of user identification information.

To be more specific, as shown in FIG. 24, for example, when a user "C" has got seated on the seat body S0, the smartphone SP compares the pressure values measured this time by the pressure sensor 21R with the screening range corresponding to the pressure sensor 21R for the user A, and if the pressure value falls within the screening range, counts up the satisfied criterion number. The smartphone SP executes this process for each of the subject pressure sensors, and determines the satisfied criterion number for the user A (i.e., the number of subject pressure sensors of which pressure values fall within the screening range for the user A). If the satisfied criterion number is 6, then the smartphone SP stores the satisfied criterion number "6" associated with the user identification information of the user A.

The smartphone SP executes the process as described above for the screening range of each of the users "B" to "E" in a similar manner. As a result, the satisfied criterion number "5" is associated with the user identification information of the user B, the satisfied criterion number "10" is associated with the user identification information of the user C, the satisfied criterion number "2" is associated with the user identification information of the user D, and the satisfied criterion number "3" is associated with the user identification information of the user E, respectively.

Figure 29:
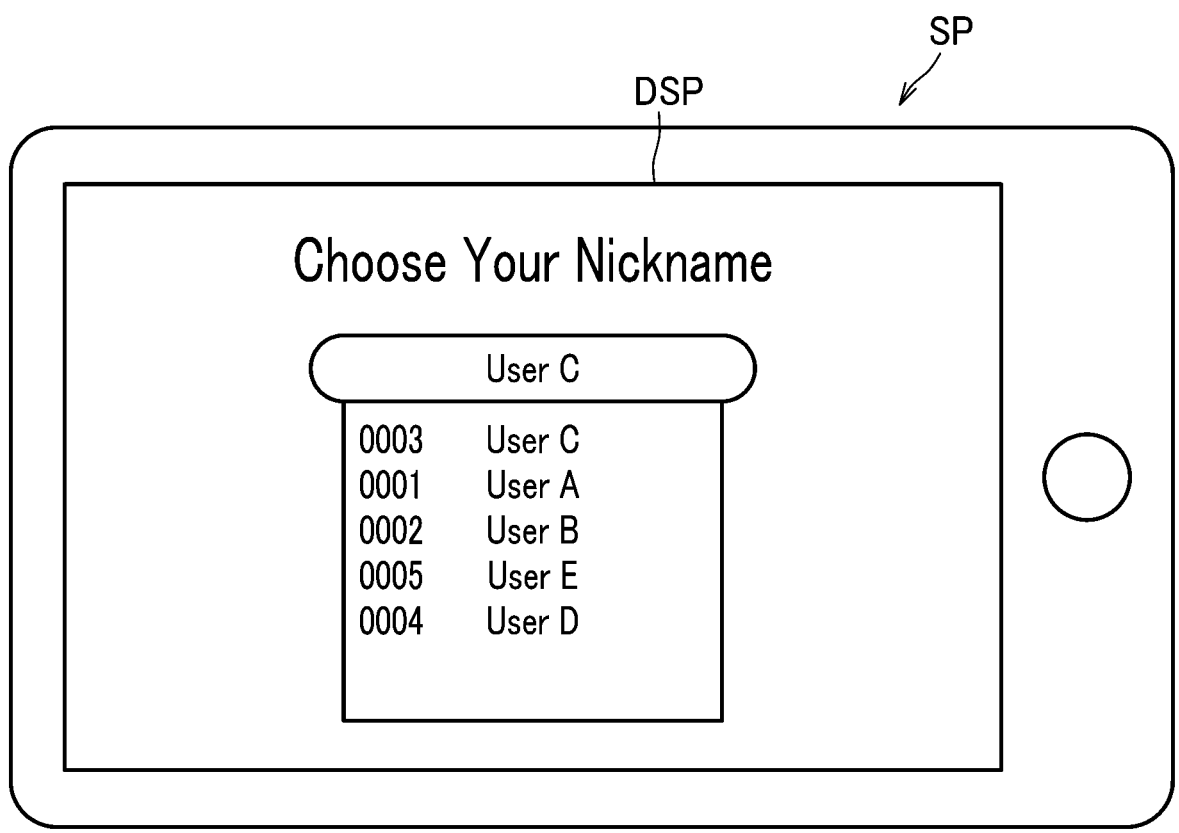
FIG. 29 is a diagram showing an image for displaying a plurality of pieces of user identification information in a pull-down menu.

The smartphone SP has a function of displaying, on the screen, the pieces of user identification information arranged in descending order of satisfied criterion numbers, based on the stored data of the user identification information and the satisfied criterion number associated therewith. To be specific, as shown in FIG. 29, the smartphone SP displays, in the pull-down menu, the pieces of user identification information in such a manner that a piece of user identification information with the greater satisfied criterion number is placed above other pieces of user identification information with the smaller satisfied criterion numbers. In other words, the smartphone SP arranges the pieces of user identification information in descending order of the satisfied criterion number downward in the pull-down menu.

Furthermore, the smartphone SP has a function of resetting a screening range corresponding to a piece of user identification information selected by a user among pieces of user identification information displayed on the screen, based on the pressure values acquired this time from the subject pressure sensors. Here, the method of resetting the screening range may be any method. For example, the pressure values newly acquired this time may be stored as the fourth-round pressure values in addition to the first-to-third-round pressure values, and an average of the first-to-fourth-round pressure values may be taken to set a screening range by the aforementioned formula (0). Alternatively, for example, the oldest pressure values (e.g., the first-round pressure values) may be replaced with the pressure values newly acquired this time, and an average of the existing pressure values may be taken to set a screening range by the aforementioned formula (0).

Next, an operation of the smartphone will be described in detail.

Figure 26:
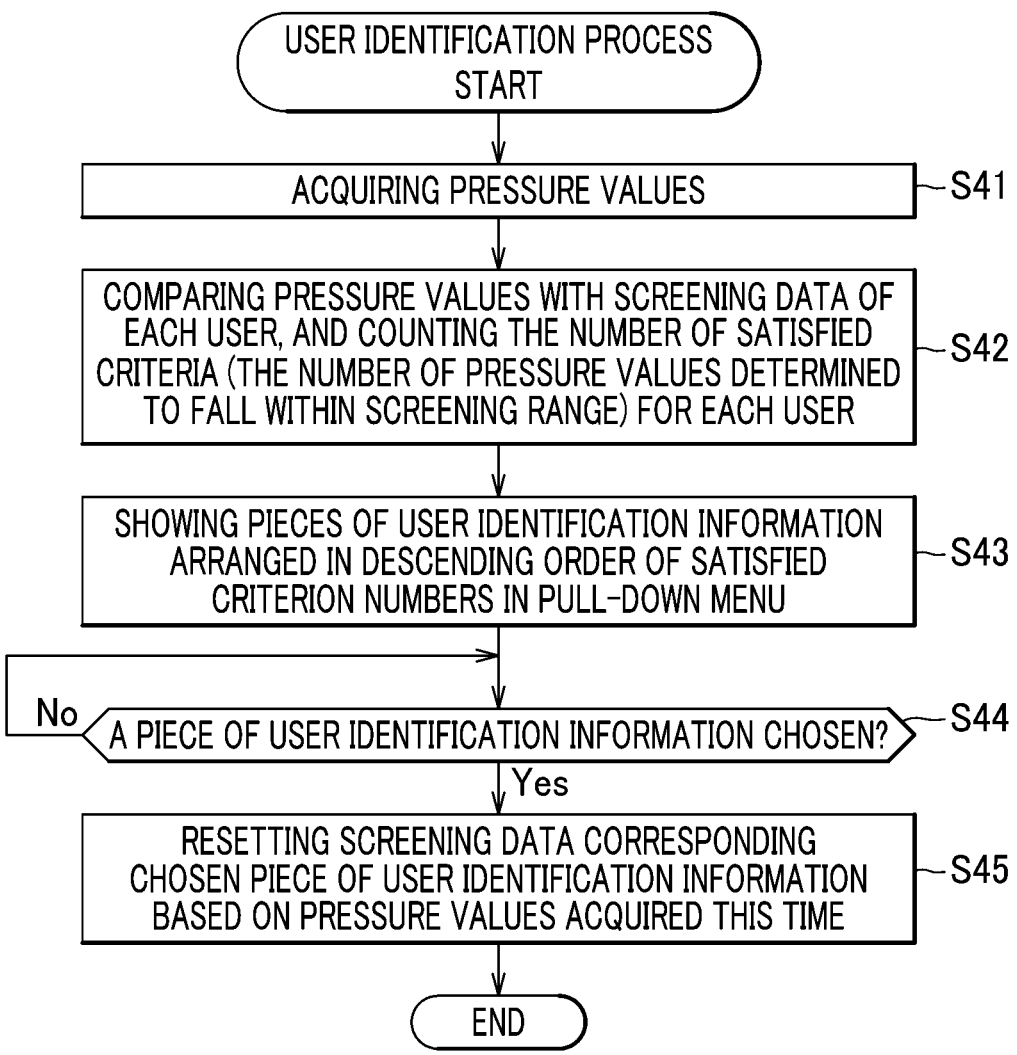
FIG. 26 is a flowchart showing a user identification process.

The smartphone SP is configured to be capable of executing a registration process shown in FIG. 25 and a user identification process shown in FIG. 26.

When a user presses a USER REGISTRATION button B11 in the start image shown in FIG. 27(*a*), the smartphone SP starts the registration process shown in FIG. 25. In the registration process, the smartphone SP first displays a nickname entry image as shown in FIG. 27(*b*), on the screen (S21).

After step S21, the smartphone SP makes a determination as to whether or not a user has entered a nickname (S22). Specifically, the smartphone SP determines that a user has entered a nickname, when the operation of entry of a nickname in an entry field of FIG. 27(*b*) is followed by the operation of pressing an ENTER button B14.

If it is determined in step S22 that a nickname has been entered (Yes), then the smartphone SP shows, on the screen, an instruction to prompt a user to get seated while assuming a predetermined posture, as shown in FIG. 28(*a*) (S23). After step S23, the smartphone SP stores pressure values acquired from the plurality of subject pressure sensors, as the first-round user pressure values, for the respective subject pressure sensors (S24).

After step S24, the smartphone SP increments the number N of sitting actions by one (S25), and then makes a determination as to whether or not the number N of sitting actions is equal to or greater than a threshold Nth (=3, in this embodiment) (S26). If it is determined in step S26 that N≥Nth is not satisfied (No), then the smartphone SP shows, on the screen, an instruction to prompt a user to rise up (S27). After step S27, the smartphone SP goes back to the process of step S23.

If it is determined in step S26 that N≥Nth is satisfied (Yes), then the smartphone SP sets, as a screening range for each subject pressure sensor, a value μ±2σ where μ is an average of a plurality of pressure values acquired from a single subject pressure sensor (S28). After step S28, the smartphone SP registers a plurality of screening ranges associated with corresponding pieces of user identification information as screening data (S29), and brings this process to an end.

When a user presses a START button B12 in the start image shown in FIG. 27(*a*), the smartphone SP starts a user identification process shown in FIG. 26. In the user identification process, the smartphone SP first acquires pressure values from a plurality of subject pressure sensors (S41). After step S41, the smartphone SP compares the pressure values acquired this time with the screening data of each of the users "A" to "E", and counts the number of satisfied criteria, which is the number of pressure values determined to fall within the screening range, for each of the users "A" to "E" (S42).

After step S42, the smartphone SP shows the pieces of user identification information arranged from the top in descending order of the satisfied criterion numbers downward in the pull-down menu as shown in FIG. 29 (S43). After step S43, a determination is made as to whether or not a user has chosen a piece of user identification information among those listed in the screen shown in FIG. 29 (S44).

If it is determined in step S44 that a piece of user identification information is chosen (Yes), then the smartphone SP resets the screening data corresponding to the chosen piece of user identification information, based on the pressure values acquired this time (S45), and brings this process to an end.

Next, one example of a specific operation of the seat experiencing system SYS3 will be described in detail. The registration process for the user "E" will be described first, and then the user identification process for the user "C" will be described. The following description is given on the premise that the registration processes for the users "A" to "D" have already been completed, and the user IDs 0001 to 0004 are assigned to the users "A" to "D", respectively.

When the user "E" launches the app for the 100-meter dash game in the smartphone SP, the start image as shown in FIG. 27(a) is displayed on the screen. When the user "E" presses the USER REGISTRATION button B11, the smartphone SP displays the nickname entry image as shown in FIG. 27(b) on the screen (S21).

When the user "E" enters "E" as his/her nickname, and presses the ENTER button B14, the smartphone SP displays an image as shown in FIG. 28(a) for prompting a user to get seated (Yes in step S22; S23). To be specific, this image includes a message image for prompting the user "E" to get seated while assuming a predetermined posture such as "Keep your mind on the S-shaped curve of your spine, and sit back in the seat", and a picture image illustrating a person who is seated on the seat.

When the user "E" follows the sitting instruction and gets seated, the smartphone SP acquires the pressure values from the plurality of subject pressure sensors, and stores the plurality of acquired pressure values as the first-round user pressure values (S24). Thereafter, the smartphone SP displays, on the screen, an image as shown in FIG. 28(b) for prompting a user to rise up (S27). To be specific, this image includes a message image for prompting the user "E" to rise up such as "Stand up, please", and a picture image illustrating a person who has risen from the seat. In this way, the user "E" is made to rise from the seat after the first-round user pressure values are acquired; thus, it is possible to make the user "E" get seated on the seat S over again, when the second-round user pressure values are acquired, so that the smartphone SP can acquire adequate pressure values.

Thereafter, the smartphone SP displays the image of FIG. 28(a) again, and prompts the user "E" to get seated, to acquire the second-round user pressure values (S23, S24). Next, the smartphone SP changes the images to that shown in FIG. 28(b), and then to that shown in FIG. 28(a), to acquire the third-round user pressure values (S27, S23, S24).

After acquiring the third-round user pressure values, the smartphone SP sets a plurality of screening ranges based on the three-round user pressure values, and associates the plurality of screening ranges with the piece of user identification information of the user "E" currently seated on the seat S, and resisters the same as the screening data corresponding to the user "E" (S29). To be more specific, the nickname "E" of the user "E" and the user ID "0005", as the piece of user identification information are associated with the screening data and registered. In this way, the registration process for the user "E" is completed.

When the user "C" presses the START button B12 in the screen displaying the start image as shown in FIG. 27(a), the smartphone SP acquires pressure values from a plurality of subject pressure sensors, and compares the pressure values with the screening data of each of the users "A" to "E", to thereby count the number of satisfied criteria for the screening data of each of the users "A" to "E" (S41, S42). When the user "C" has got seated on the seat S, the numbers of satisfied criteria for the screening data of the users "A" to "E" are: A=6, B=5, C=10, D=2, and E=3, respectively, as shown in FIG. 24.

After counting the number of satisfied criteria for the screening data of each of the users "A" to "E", the smartphone SP displays the pieces of user identification information arranged from top in descending order of the numbers of satisfied criteria in the pull-down menu, as shown in FIG. 29. To be more specific, if the user "C" has got seated on the seat S, then the smartphone SP arranges the pieces of user identification information from top downward in the order of C, A, B, E, and D.

When the user "C" chooses his/her own piece of user identification information, the smartphone SP resets the screening data of the user "C" based on the pressure values acquired this time (Yes in Step S44; S45). In this way, the user identification process for the user "C" is completed. After completion of the user identification process, the smartphone SP executes the 100-meter dash game based on the data regarding the user "C".

In the seat S configured according to the present embodiment as described above, the following advantageous effects can be achieved.

When a specific user is on the seat body S0, the pressure values acquired from the subject pressure sensors are more likely to fall within the screening range for the specific user, and thus the piece of user identification information of the specific user is given precedence over the other pieces of user identification information when the pieces of user identification information are displayed on the screen. Accordingly, the user on the seat body S0 can select his/her own user identification information with increased ease.

Since a plurality of pressure values acquired from the plurality of subject pressure sensors are compared with a plurality of screening ranges, the user on the seat body S0 can be discriminated from the other users more precisely.

Since each time the piece of user identification information is selected by the user, the user's own screening range is reset based on the pressure values acquired this time, the screening range can be set more precisely.

Although the fifth embodiment has been described above, specific configurations may be modified where appropriate and implemented as will be described below as other embodiments.

In describing the embodiment above, the method of displaying a piece of user identification information that takes precedence over another piece of user identification information is implemented by placing it in a location higher than the other piece of user identification information in the pull-down menu; however, the method is not limited thereto. For example, only the pieces of user identification information that take precedence over other pieces of user identification information may be displayed on the screen, while the other pieces of user identification information may be excluded from the list displayed on the screen. Alternatively, pieces of user identification information that take precedence over other pieces of user identification information may be shown larger, or in predominant color, i.e., more dominant, than the other pieces of user identification information.

In describing the embodiment above, the nickname and the user ID are taken as an example of a piece of user identification information, but the user identification information is not limited thereto; for example, the user identification information may comprise either one of the nickname or the user ID, or may comprise a full name of the user.

In describing the embodiment above, the controller and the terminal are illustrated as being implemented in the smartphone SP, but this is not a prerequisite; for example, the controller may be implemented in the ECU 100, and the terminal may be implemented in the smartphone SP. In other words, the ECU 100 may be configured to discriminate a piece of user identification information that takes precedence over another piece of user identification information, and transmit an image showing the piece of user identification information that takes precedence over the other piece of user identification information more prominently than the other piece of user identification information, to the smartphone SP for display on the screen of the smartphone SP.

The results of the 100-meter dash game may be uploaded onto a cloud server. With this configuration, the world ranking and the like can be viewed via the cloud. The user's own records can be accumulated on the cloud for future reference. Furthermore, the other persons' records can be viewed as well. In addition, the user's own records and the other persons' records can be compared.

The seat experiencing system described above may be applied in autonomous driving vehicles. In this application, the seat experiencing system may be configured to be made available on condition that the vehicle is being operated under the autonomous driving mode. Further, when the vehicle switches back from the autonomous driving mode during the use of the seat experiencing system, the use of the seat experiencing system may be restricted before the switching takes place. In that event, a notification may be made through a voice navigation or a display message by activating an advance notice means, so as not to place restrictions unexpectedly, to the effect that restrictions will be placed after a lapse of a predetermined period of time.

The seat experiencing system may alternatively be configured to be made available only when the vehicle is stopped. A determination as to whether or not the vehicle is stopped may be made, based on a determination as to whether or not the vehicle speed is zero, or whether or not the shift lever is in the parking position, or otherwise.

The controller of the seat experiencing system may be configured to acquire information about abnormal events which would occur in the external environment or in the seat experiencing system itself. In this configuration, the seat experiencing system may be configured to place limitations on its service to be offered, upon receipt of information about abnormal event(s). Examples of the abnormal events in the seat experiencing system itself may include an anomaly in a sensor, an anomaly (break) in a harness, an anomaly of the ECU, an anomaly in communication (including an anomaly in the terminal), an anomaly in temperature regulators, such as a heater, a fan, or the like, provided in the seat, an anomaly in an actuator for actuating a part or the whole body of the seat, an anomaly in other sensors, such as a seat weight sensor, a temperature sensor, or the like, an anomaly related to the remaining amount of consumables or the usage state, e.g., an aromatic substance for use in the seat is nearing depletion, and an anomaly in the seat controller itself. Examples of the abnormal events in the external environment may include a situation under which execution of apps is undesirable, such as an approach of another vehicle, bad wheeling road condition, a vehicle running at high speeds, a strike of an earthquake, destination approaching, the destination having been reached already, it turned out that the game will not come to an end before reaching a destination, the fuel about to run out, the battery about to run down, the temperature or humidity too high in the vehicle or outside, etc.

The limitations may be placed in response to a single occurrence of an abnormal event, or after a plurality of occurrences of the abnormal event. The method of placing limitations may be configured to vary with the level of the abnormality. For example, at the first level, a notification of a recommended option to stop using may be made by a text message, a voice message or the like; at the second level, a notification of a serious proposal to avoid using may be made by a text message, a voice message or the like; and at a third level, the system may be forcefully terminated.

The seat experiencing system may also be configured such that if some of the sensors provided at a specific area are found faulty, games using the other sensors found not faulty are recommended. For example, if sensors at the seat surface of the seat cushion are found faulty, games using sensors at the side portions provided at the both sides of the seat surface of the seat cushion and bulging up from the seat surface are recommended.

In describing the embodiment above, the pressure sensors 21 to 26 are taken as examples of a sensor, but this is not a prerequisite; for example, the sensor may be an optical sensor, a capacitance sensor, a temperature sensor, an acoustic sensor for detecting sound. For example, by using optical sensors or capacitance sensors, the physical state (body form, etc.) of a user can be determined on the basis of the ON/OFF states of the sensors. With the temperature sensor, a screening of users can be broadly (not strictly) performed, for example, by making use of varying basic temperatures of the users. With the acoustic sensor, a screening of users can be broadly performed, for example, by making use of varying pitches of the voices of the users. With the pressure sensors of the above-described embodiment, a screening of users can be broadly performed by making use of varying blood pressures and/or weights of the users.

In the above-described embodiment, the pressure values of a plurality of sensors are compared with a plurality of screening ranges, but this configuration is not a prerequisite; a single pressure sensor may be compared with a single screening range, instead.

The sensors may be provided at left and right side portions (portions bulging from the seat surface) of the seat cushion or the seat back, or at the headrest, the armrests, or parts around the seat (e.g., the instrument panel, the door, the floor, etc.).

The seat may be a car seat for use in an automobile, or any other type of seat, such as seats for use in a ship, an aircraft, etc. The seat may not be a vehicle seat; the seat may, for example, include a legless chair, a chair as furniture or for outdoor use, a chair in a waiting room of a hospital, a bench in a park, a bed, a mattress, etc.

In describing the embodiment above, the smartphone SP is taken as an example of a terminal, but this is not a prerequisite; the terminal may be, for example, a tablet, or a PC, etc. The terminal may be equipped in the seat, provided integrally with the seat. The terminal may be a terminal which constitutes a car navigation system. The terminal may be a terminal having a large screen by which a plurality of users can watch and listen to the contents presented therefrom.

Any of the elements explained in relation to the fifth embodiment and modified examples may be implemented in combination as desired.

Figure 30:
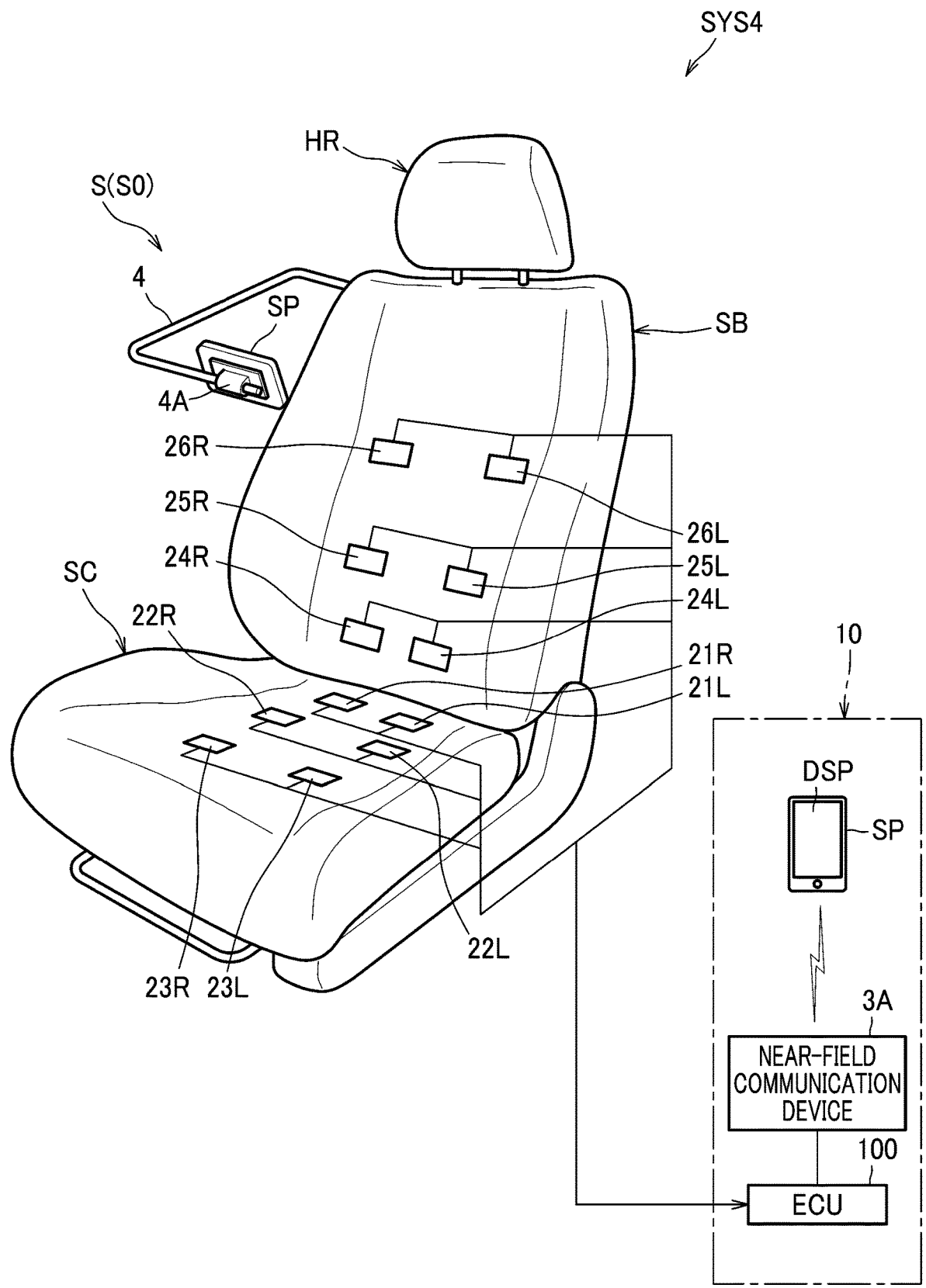
FIG. 30 is a diagram showing a seat experiencing system according to a sixth embodiment.

Next, a sixth embodiment will be described in detail with reference made to the drawings where appropriate. As shown in FIG. 30, a seat experiencing system SYS4 of this embodiment is configured to comprise a seat S and an in-seat experience device 10.

The seat S includes a seat body S0 and pressure sensors 21 to 26. The seat body S0 is, for example, a vehicle seat installed in a vehicle such as a car, and includes a seat cushion SC, a seat back SB, and a headrest HR. The seat cushion SC and the seat back SB have an outer covering under which a plurality of pressure sensors 21 to 26 are provided. The pressure sensors 21 to 26 are sensors that acquire information for use in detection of a posture and a motion of a user on the seat body S0.

The pressure sensors 21 to 26 are so arranged as to be capable of detecting a state of a seat surface facing a user seated on the seat body S0, to acquire values of pressure from the user seated on the seat body S0. An ECU (Electronic Control Unit) 100 is a device that controls an operation (e.g., of a motor for an electrically powered reclining mechanism, a heater, etc., not shown) of the seat body S0, and is connected to the pressure sensors 21 to 26 and thereby allowed to acquire measurement values from the respective pressure sensors 21 to 26.

The pressure sensors 21 to 26 are provided in pairs, i.e., each located left and right, symmetric with respect to a laterally central position of the seat S. In the following description and drawings which will be referred to below, pressure sensors 21 to 26 located on the left side may be designated by reference characters with "L" appended thereto and referred to as "left sensor", and pressure sensors 21 to 26 located on the right side may be designated by reference characters with "R" appended thereto and referred to as "right sensor", so that distinctions are drawn therebetween.

In the seat cushion SC, the pressure sensors 21 to 23 are provided.

The pressure sensors 21 are provided in positions corresponding to the lowermost portions of ischial bones of the user. On these positions, the load of the user is borne largest.

The pressure sensors 22 are located a little frontward of the pressure sensors 21.

The pressure sensors 21 and the pressure sensors 22 are both provided to measure the pressure from the buttocks of the user, and only either one may suffice therefor.

The pressure sensors 23 are located frontward of and distanced far from the pressure sensors 21 and the pressure sensors 22. The pressure sensors 23 are located under the thighs of the user, and capable of determining values of pressure from the thighs of the user.

In the seat back SB, the pressure sensors 24 to 26 are provided. The pressure sensors 24 are provided in positions corresponding to the waist of the user.

The pressure sensors 25 are located in positions corresponding to the back of the user, specifically, in positions a little higher than the positions of the pressure sensors 24.

The pressure sensors 26 are located above and distanced far from the pressure sensors 24 and the pressure sensors 25. The pressure sensors 26 are located in positions corresponding to the shoulders of the user, and capable of determining values of pressure from the shoulders of the user.

In the present embodiment, the seat experiencing system SYS4 is configured to provide a sitting posture age diagnosis by using the pressure sensors 21 to 26. Herein, the sitting posture age diagnosis refers to a process of determining a sitting posture age corresponding to the posture or motion of a user seated on the seat S, and notifying the user of the sitting posture age as determined. To be more specific, the seat experiencing system SYS4 causes the smartphone SP to show an instruction to a user, on the display DSP as the screen thereof, to prompt the user to assume a predetermined posture, or to make a predetermined motion, or the like, to thereby determine a sitting posture age.

The seat body S0 is provided with a holder 4 for holding a smartphone SP. The holder 4 is formed by bending a wire, with one end fixed to the seat back SB and the other end having a retaining portion 4A for the smartphone SP to be retained thereto. With the smartphone SP being retained to the retaining portion 4A, the user can see the display DSP of the smartphone SP without holding the smartphone SP by hand.

The in-seat experience device 10 is configured to comprise an ECU 100 and a smartphone SP as a controller.

A near-field communication device 3A which enables near-field wireless communication, such as Bluetooth (registered trademark), Wi-Fi (registered trademark), etc. is connected to the ECU 100. The ECU 100 is connected to the pressure sensors 21 to 26. In the present embodiment, the ECU 100 and the near-field communication device 3A are provided at the seat body S0. The smartphone SP acquires measurement values from the pressure sensors 21 to 26 via the ECU 100.

The ECU 100 and the smartphone SP each include a CPU, a ROM, a RAM, a rewritable nonvolatile memory, etc. (not shown), and are configured to execute pre-stored programs. The smartphone SP further includes the display DSP. The smartphone SP is configured to operate according to the program, and thus functions as means for carrying out a sitting posture age diagnosis.

The smartphone SP has a function of computing first evaluation values B2, C2, a second evaluation value D2, and a third evaluation value E2 for use in the sitting posture age diagnosis, based on the measurement values acquired from predetermined pressure sensors selected among the pressure sensors 21 to 26. The first evaluation value B2 is an evaluation value corresponding to leftward or rightward postural deviation of an upper body of a user, and the first evaluation value C2 is an evaluation value corresponding to leftward or rightward postural deviation of a lower body of the user.

It is to be understood that the older a person is, the more the leftward or rightward postural deviation of his/her upper or lower body is observed when he/she is seated on the seat S, due to pelvic torsion or the like. Therefore, the degree of the leftward or rightward postural deviation of the upper or lower body as determined based on the first evaluation values B2, C2 can be used to assume the age, such that the more the leftward or rightward postural deviation of the upper or lower body, the greater the age is.

The second evaluation value D2 is an evaluation value corresponding to retention of the posture of the user for a first predetermined time period. To be specific, the second evaluation value D2 corresponds to a range of variation of the pressure value for the first predetermined time period.

It is to be understood that the older a person is, the more difficult it is for that person to retain his/her sitting posture on the seat S, and the more his/her body sways. Therefore, the range of variation of the pressure value for the first predetermined time period can be used to assume the age, such that the greater the range of variation, the greater the age is.

The third evaluation value E2 is an evaluation value corresponding to an amount of motion of the user for a second predetermined time period. It is to be understood the greater the amount of motion of the user on the seat, the younger the user is. Therefore, it can be assumed, based on the third evaluation value E2, that the greater the amount of motion of a person on the seat, the less the age is. In the present embodiment, the motion on the seat S is a motion of a user moving his/her two legs up and down alternately on the seat S.

The smartphone SP computes the first evaluation value B2 indicative of leftward or rightward postural deviation of the upper body of a user, based on the pressure values acquired from the pressure sensors 24, 25 corresponding to the waist and the back of the user. To be more specific, the smartphone SP computes the first evaluation value B2 by the following formula (1):

$$B2=(L4+L5)-(R4+R5) \qquad (1)$$

where L4 is an average of pressure values acquired from the left sensor 24L for a prescribed time period, L5 is an average of pressure values acquired from the left sensor 25L for the prescribed time period, R4 is an average of pressure values acquired from the right sensor 24R for the prescribed time period, and R5 is an average of pressure values acquired from the right sensor 25R for the prescribed time period.

The smartphone SP computes an upper-body deviation degree B3 indicative of a degree of leftward or rightward postural deviation of an upper body based on the first evaluation value B2 as computed, by the following formula (2):

$$B3=|B2+Ya1\times100| \qquad (2)$$

where Ya1 is a coefficient.

The smartphone SP makes a determination, based on the first evaluation value B2, as to which side the upper body deviates, leftward or rightward, and makes a determination, based on the upper-body deviation degree B3, as to how much the upper body deviates leftward or rightward. To be more specific, the smartphone SP compares the first evaluation value B2 with a positive threshold (Yb1) and a negative threshold (−Yb1) to determine to which side the upper body deviates, leftward or rightward.

It is to be understood that the coefficient Ya1 and the threshold Yb1 may be determined as appropriate through experiment or simulation, etc. The coefficient Ya1 and/or the threshold Yb1 may be changed where appropriate, for example, based on information on the values of pressure received from a plurality of users. The same goes for coefficients and thresholds which will be described later.

If B2>Yb1, then the smartphone SP determines that the upper body deviates leftward. If B2<−Yb1, then the smartphone SP determines that the upper body deviates rightward. If −Yb1≤B2≤Yb1, then the smartphone SP determines that the upper body does not deviate leftward or rightward, and the lateral load distribution of the upper body is finely balanced.

The smartphone SP compares the upper-body deviation degree B3 with the thresholds Yb2 and Yb3 to determine how much the upper body deviates leftward or rightward. Herein, the values of the thresholds Yb2 and Yb3 are set to satisfy: Yb2<Yb3.

If B3<Yb2, then the smartphone SP determines that the upper body does not deviate leftward or rightward, and the lateral load distribution of the upper body is finely balanced. If Yb2≤B3<Yb3, then the smartphone SP determines that the upper body deviates leftward or rightward to some degree, and the lateral load distribution of the upper body is not finely balanced. If B3≥Yb3, then the smartphone SP determines that the upper body deviates leftward or rightward to a large degree, and the lateral load distribution of the upper body is unbalanced.

The smartphone SP computes an upper-body balance age B1 as a sitting posture age corresponding to the leftward or rightward postural deviation of the upper body based on the first evaluation value B2, by the following formula (3):

$$B1=Ya2\times|B2|+Ya3 \qquad (3)$$

where Ya2 and Ya3 are coefficients.

Herein, the coefficient Ya2 is a coefficient for converting the first evaluation value B2 into a numeric value corresponding to the age. The coefficient Ya3 may, for example, be a lower limit in the range of ages of a plurality of users who use the seat experiencing system SYS4. Specifically, for example, in cases where the ages of a plurality of users range from 20 to 90, Ya3=20 may be adopted.

The smartphone SP computes the upper-body balance age B1 by the formulae (1) and (3) and thus sets the upper-body balance age B1 such that the greater the magnitude of a difference between a pressure value from the left sensor 24L and a pressure value from the right sensor 24R (the sensors 24L, 24R being provided in positions corresponding to the waist), the greater the upper-body balance age B1 is made. The smartphone SP is also configured such that the greater the magnitude of a difference between a pressure value from the left sensor 25L and a pressure value from the right sensor 25R (the sensors 25L, 25R being provided in positions corresponding to the back), the greater the upper-body balance age B1 is made.

When the upper-body balance age B1 as computed is greater than the pre-specified upper limit in the range of the ages of a plurality of users, the smartphone SP may set the upper-body balance age B1 at the upper limit in the range of the ages. When the upper-body balance age B1 as computed is smaller than the pre-specified lower limit in the range of the ages of a plurality of users, the smartphone SP may set the upper-body balance age B1 at the lower limit in the range of the ages. It is to be understood that this way of computation may be applied to computation of ages in other occasions which will be described later.

The smartphone SP computes the first evaluation value C2 indicative of leftward or rightward postural deviation of the lower body of a user, based on the pressure values acquired from the pressure sensors 21 to 23 corresponding to the lower body of the user. To be more specific, the smartphone SP computes the first evaluation value C2 by the following formula (4):

$$C2=(L1+L2+L3)-(R1+R2+R3) \qquad (4)$$

where L1 is an average of pressure values acquired from the left sensor 21L for a prescribed time period, L2 is an average of pressure values acquired from the left sensor 22L for the prescribed time period, L3 is an average of pressure values acquired from the left sensor 23L for the prescribed time period, R1 is an average of pressure values acquired from the right sensor 21R for the prescribed time period, R2 is an average of pressure values acquired from the right sensor 22R for the prescribed time period, and R3 is an average of pressure values acquired from the right sensor 23R for the prescribed time period.

The smartphone SP computes a lower-body deviation degree C3 indicative of a degree of leftward or rightward postural deviation of a lower body based on the first evaluation value C2 as computed, by the following formula (5):

$$C3=|C2 \div Yc1 \times 100| \tag{5}$$

where Yc1 is a coefficient.

The smartphone SP makes a determination, based on the first evaluation value C2, as to which side the lower body deviates, leftward or rightward, and makes a determination, based on the lower-body deviation degree C3, as to how much the lower body deviates leftward or rightward. To be more specific, the smartphone SP compares the first evaluation value C2 with a positive threshold (Yd1) and a negative threshold (−Yd1) to determine to which side the lower body deviates, leftward or rightward.

If C2>Yd1, then the smartphone SP determines that the lower body deviates leftward. If C2<−Yd1, then the smartphone SP determines that the lower body deviates rightward. If −Yd1≤C2≤Yd1, then the smartphone SP determines that the lower body does not deviate leftward or rightward, and the lateral load distribution of the lower body is finely balanced.

The smartphone SP compares the lower-body deviation degree C3 with the thresholds Yd2 and Yd3 to determine how much the lower body deviates leftward or rightward. Herein, the values of the thresholds Yd2 and Yd3 are set to satisfy: Yd2<Yd3.

If C3<Yd2, then the smartphone SP determines that the lower body does not deviate leftward or rightward, and the lateral load distribution of the lower body is finely balanced. If Yd2≤C3<Yd3, then the smartphone SP determines that the lower body deviates leftward or rightward to some degree, and the lateral load distribution of the lower body is not finely balanced. If C3≥Yd3, then the smartphone SP determines that the lower body deviates leftward or rightward to a large degree, and the lateral load distribution of the lower body is unbalanced.

The smartphone SP computes a lower-body balance age C1 as a sitting posture age corresponding to the leftward or rightward postural deviation of the lower body, based on the first evaluation value C2, by the following formula (3):

$$C1=Yc2 \times |C2|+Yc3 \tag{6}$$

where Yc2 and Yc3 are coefficients.

It is to be understood that the coefficients Yc2 and Yc3 may be set in a manner similar to that in which the coefficients Ya2 and Ya3 are set as described above.

The smartphone SP computes the lower-body balance age C1 by the formulae (4) and (6) and thus sets the lower-body balance age C1 such that the greater the magnitude of a difference between a pressure value from the left sensor 21L and a pressure value from the right sensor 21R (the sensors 21L, 21R being provided in positions corresponding to those of ischial bones), the greater the lower-body balance age C1 is made. The smartphone SP is also configured such that the greater the magnitude of a difference between a pressure value from the left sensor 22L and a pressure value from the right sensor 22R (the sensors 22L, 22R being provided in positions corresponding to a region a little frontward of the ischial bones), the greater the lower-body balance age C1 is made. The smartphone SP is further configured such that the greater the magnitude of a difference between a pressure value from the left sensor 23L and a pressure value from the right sensor 23R (the sensors 23L, 23R being provided in positions corresponding to the thighs), the greater the lower-body balance age C1 is made.

The smartphone SP computes a lateral balance age A1 as a sitting posture age corresponding to a lateral balance of the whole body of a user, based on the upper-body balance age B1 and the lower-body balance age C1, by the following formula (7):

$$A1=Za1 \times B1+Za2 \times C1 \tag{7}$$

where Za1 and Za2 are coefficients.

It is to be understood that the coefficients Za1 and Za2 may be set, respectively, at values which are less than 1 and of which the sum is 1. For example, the coefficients Za1 and Za2 may be set at 0.5, respectively, or may be set such that one is greater than the other for the purpose of weighting.

The smartphone SP computes a second evaluation value D2 corresponding to retention of a posture of the user for the first predetermined time period, based on the pressure values acquired from the left sensor 24L and the right sensor 24R provided in positions corresponding to the waist of the user. To be more specific, the smartphone SP computes the second evaluation value D2 by the following formula (8):

$$D2=(L4\max+R4\max)-(L4 \min + R4 \min) \tag{8}$$

where L4*max* is a maximum of pressure values acquired from the left sensor 24L for a first predetermined time period, R4*max* is a maximum of pressure values acquired from the right sensor 24R for the first predetermined time period, L4 min is a minimum of pressure values acquired from the left sensor 24L for the first predetermined time period, R4 min is a minimum of pressure values acquired from the right sensor 24R for the first predetermined time period.

The smartphone SP computes a posture retention degree D3 indicative of a degree of retention of a posture of a user, based on the second evaluation value D2 as computed, by the following formula (9):

$$D3=|D2 \pm Wa1 \times 100| \tag{9}$$

where Wa1 is a coefficient.

The smartphone SP makes a determination, based on the posture retention degree D3, as to how good the user has been retaining his/her posture. To be more specific, the smartphone SP compares the posture retention degree D3 with the thresholds Wb1 and Wb2 to determine how good the user has been retaining his/her posture. Herein, the values of thresholds Wb1 and Wb2 are set to satisfy: Wb1<Wb2.

If D3<Wb1, then the smartphone SP determines that the user has been successful in retaining his/her posture. If Wb1≤D3<Wb2, then the smartphone SP determines that the user's body swayed to some degree during the first predetermined time period, and thus the user's attempt made to retain his/her posture proved not so good. If D3≥Wb2, then the smartphone SP determines that the user's body swayed to a large degree during the first predetermined time period, and thus the user's attempt made to retain his/her posture proved not good, that is, unsuccessful.

The smartphone SP computes a posture retention age D1 as a sitting posture age corresponding to retention of the posture of the user, based on the second evaluation value D2, by the following formula (10):

$$D1=Wa2 \times |D2|+Wa3 \tag{10}$$

where Wa2 and Wa3 are coefficients.

It is to be understood that the coefficients Wa2 and Wa3 may be set in a manner similar to that in which the coefficients Ya2 and Ya3 are set as described above.

The smartphone SP computes the posture retention age D1 by the formulae (8) and (10) and thus sets the posture retention age D1 such that the greater a range of variation of the pressure value from the left sensor 24L for the first predetermined time period, the greater the posture retention age D1 is made. The smartphone SP is also configured such that the greater a range of variation of the pressure value from the right sensor 24R for the first predetermined time period, the greater the posture retention age D1 is made.

The smartphone SP computes a third evaluation value E2 corresponding to an amount of motion of a user for a second predetermined time period, based on the pressure values acquired from the left sensor 23L and the right sensor 23R provided in positions corresponding to the thighs of a user. To be more specific, the smartphone SP computes the third evaluation value E2 by the following formula (11):

$$E2 = \Sigma E(t) \qquad (11)$$

where $E(t)=|L3(t)-R3(t)|$, $L3(t)$ is a pressure value acquired from the left sensor 23L at a predetermined point in time during the second predetermined time period, $R3(t)$ is a pressure value acquired from the right sensor 23R at a predetermined point in time during the second predetermined time period.

In other words, the smartphone SP obtains an absolute value of a remainder found by subtracting the pressure value acquired from the right sensor 24R from the pressure value acquired from the left sensor 24L each time when the smartphone SP acquires the pressure values from the left sensor 23L and the right sensor 23R during the second predetermined period, and adds up the absolute value to the total successively. Accordingly, the greater the amount of motion of legs moved up and down on the seat S, the greater the third evaluation value E2 is made.

In the present embodiment, the third evaluation value E2 as the amount of motion is computed by the formula (11); however, the third evaluation value E2 may be computed in any other way. For example, the number of times the user has moved up and down his/her legs may be obtained from the pressure values, and the obtained number of times may be used as the third evaluation value E2.

The smartphone SP computes a muscle strength level E3 indicative of a level of user's muscle strength which varies according to the amount of motion of the user, based on the computed third evaluation value E2, by the following formula (12):

$$E3 = E2 \div Va1 \times 100$$

where Va1 is a coefficient.

The smartphone SP compares the muscle strength level E3 with the thresholds Vb1 and Vb2, to determine how high the user's muscle strength level is. Herein, the values of thresholds Vb1 and Vb2 are set to satisfy: Vb1>Vb2.

If E3>Vb, then the smartphone SP determines that the user's muscle strength level is high enough, and thus the user has an adequate muscle strength level. If Vb1≥E3>Vb2, then the smartphone SP determines that the user's muscle strength level is not so good. If E3≤Vb2, then the smartphone SP determines that the user's muscle strength level is not good, that is, low.

The smartphone SP computes a muscle strength age E1 as a sitting posture age corresponding to the amount of motion of the user, based on the third evaluation value E2, by the following formula (13):

$$E1 = |-Va2 \times E2 + Va3| \qquad (13)$$

where $-Va2$ and Va3 are coefficients.

Herein, the coefficient $-Va2$ is a negative coefficient for converting the third evaluation value E2 into a numeric value corresponding to an age. The coefficient Va3 may, for example, be an upper limit in the range of ages of a plurality of users who use the seat experiencing system SYS4. To be specific, for example, in cases where the ages of a plurality of users range from 20 to 90, Va3=90 may be adopted.

The smartphone SP computes the muscle strength age E1 by the formulae (11) and (13) and thus sets the muscle strength age E1 such that the greater the amount of motion of the user on the seat S, the less the muscle strength age E1 is made.

The smartphone SP computes a sitting posture age As of a user with consideration given to the leftward or rightward deviation of the body, the retention of the posture, and the muscle strength of the user, based on the lateral balance age A1, the posture retention age D1, and the muscle strength age E1, by the following formula (14):

$$As = Ta1 \times A1 + Ta2 \times D1 + Ta3 \times E1 \qquad (14)$$

where Ta1, Ta2 and Ta3 are coefficients.

It is to be understood that the coefficients Ta1, Ta2 and Ta3 may be set, respectively, at values which are less than 1 and of which the sum is approximately 1. For example, the coefficients Ta1, Ta2 and Ta3 may be set at 0.3, respectively, or may be set such that the coefficients have values different from one another for the purpose of weighting.

The lateral balance age A1 is computed, based on the first evaluation values B2 and C2, by the formulae (3), (6) and (7) mentioned above. The posture retention age D1 is computed, based on the second evaluation value D2, by the formula (10) mentioned above, and the muscle strength age E1 is computed, based on the third evaluation value E2, by the formula (13) mentioned above. Accordingly, the smartphone SP determines the sitting posture age As based on the first evaluation values B2, C2, the second evaluation value D2, and the third evaluation value E2.

Next, a detailed description will be given of an operation of the smartphone SP.

Figure 31:
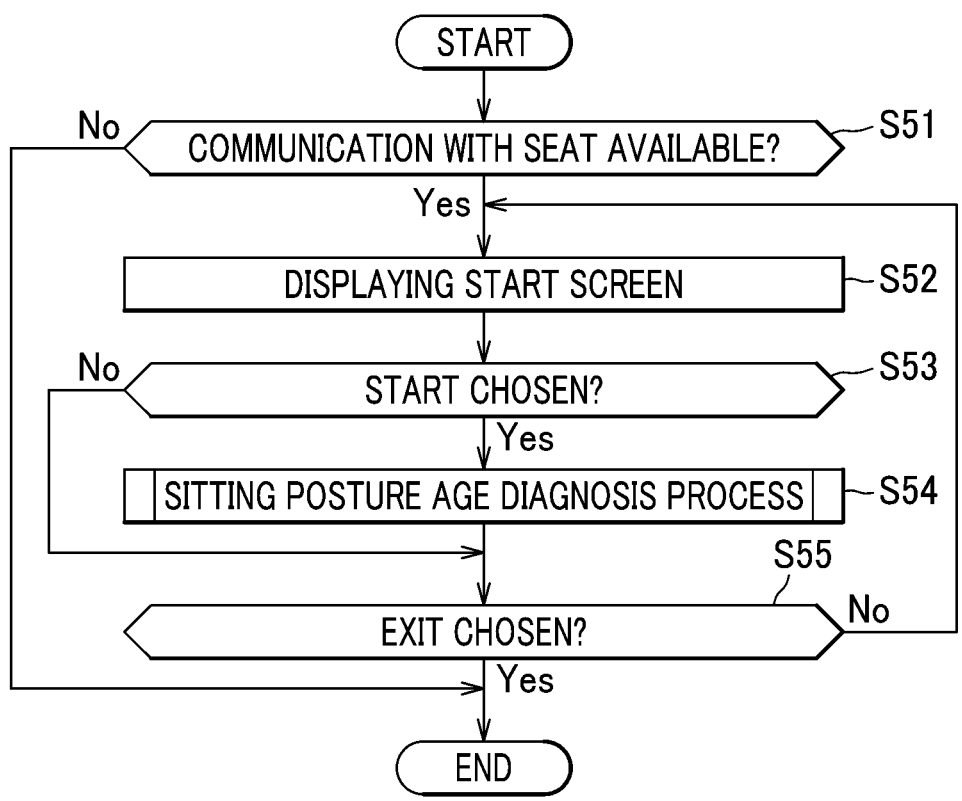
FIG. 31 is a flowchart showing a process to be executed in a smartphone.

In response to a user's operation of launching an application for carrying out a sitting posture age diagnosis, the smartphone SP starts the process shown in FIG. 31 (START). In this process, the smartphone SP first makes a determination as to whether communication with the seat S is available (S51).

If it is determined in step S51 that the communication is not available (No), then the smartphone SP brings this process to an end. If it is determined in step S51 that the communication is available (Yes), then the smartphone SP presents a start screen for the sitting posture age diagnosis (see FIG. 33) on the display DSP (S52).

Figure 33:
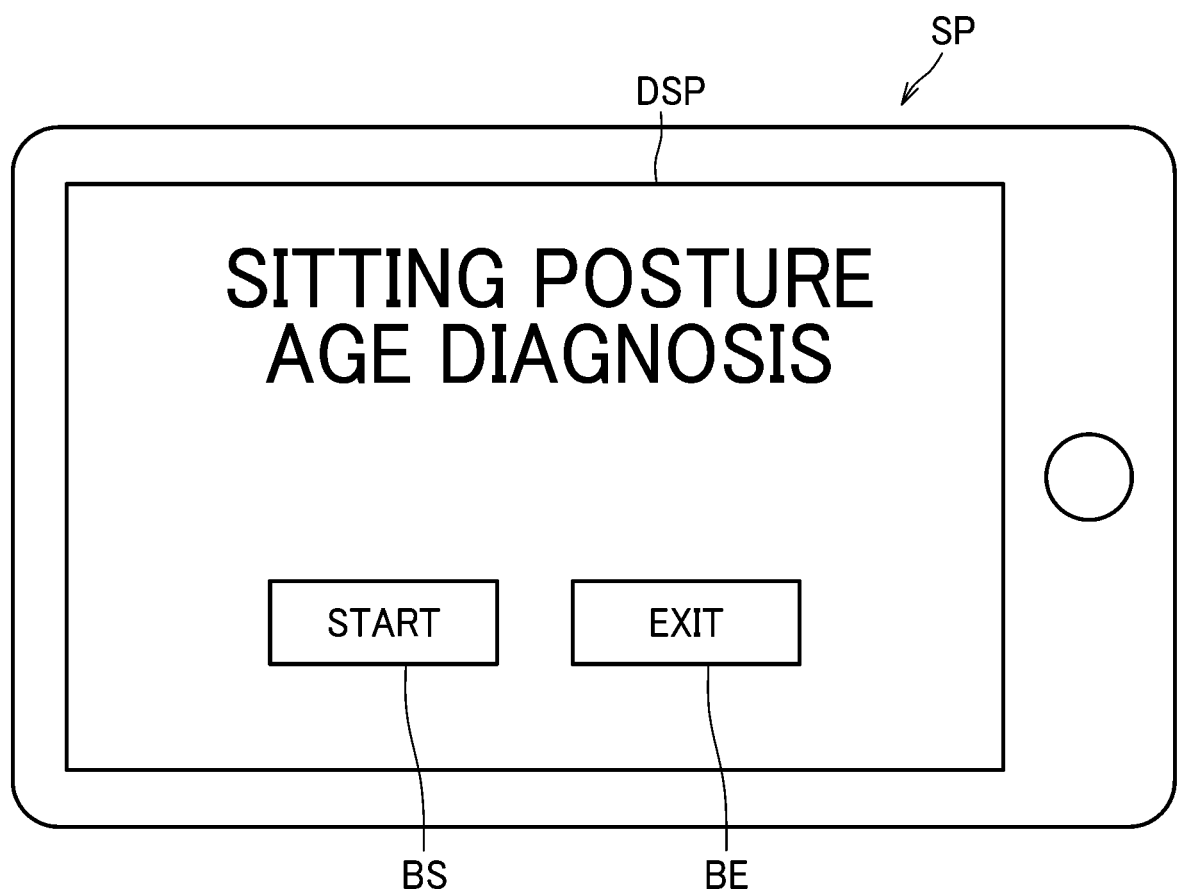
FIG. 33 is a diagram showing a start screen.

In the start screen shown in FIG. 33, there are shown a start button BS for starting the sitting posture age diagnosis and a button BE for exiting the sitting posture age diagnosis.

After step S52, the smartphone SP makes a determination as to whether or not the start button BS has been chosen (S53). If it is determined in step S53 that the start button BS has been chosen (Yes), then the smartphone SP starts the sitting posture age diagnosis process (S54). The sitting posture age diagnosis process will be described later in detail.

If the sitting posture age diagnosis process comes to an end, the smartphone SP displays the start screen shown in FIG. 33. Referring back to FIG. 31, after step S54, or if the result of determination in step S53 turns out to be No, then the smartphone SP makes a determination as to whether or not the button BE for exiting the sitting posture age diagnosis has been chosen (S55). If it is determined in step S55 that the button BE has not been chosen (No), then the smartphone SP goes back to the process in step S52. If it is determined in step S55 that the button BE has been chosen (Yes), then the smartphone SP brings this process to an end.

Figure 32:
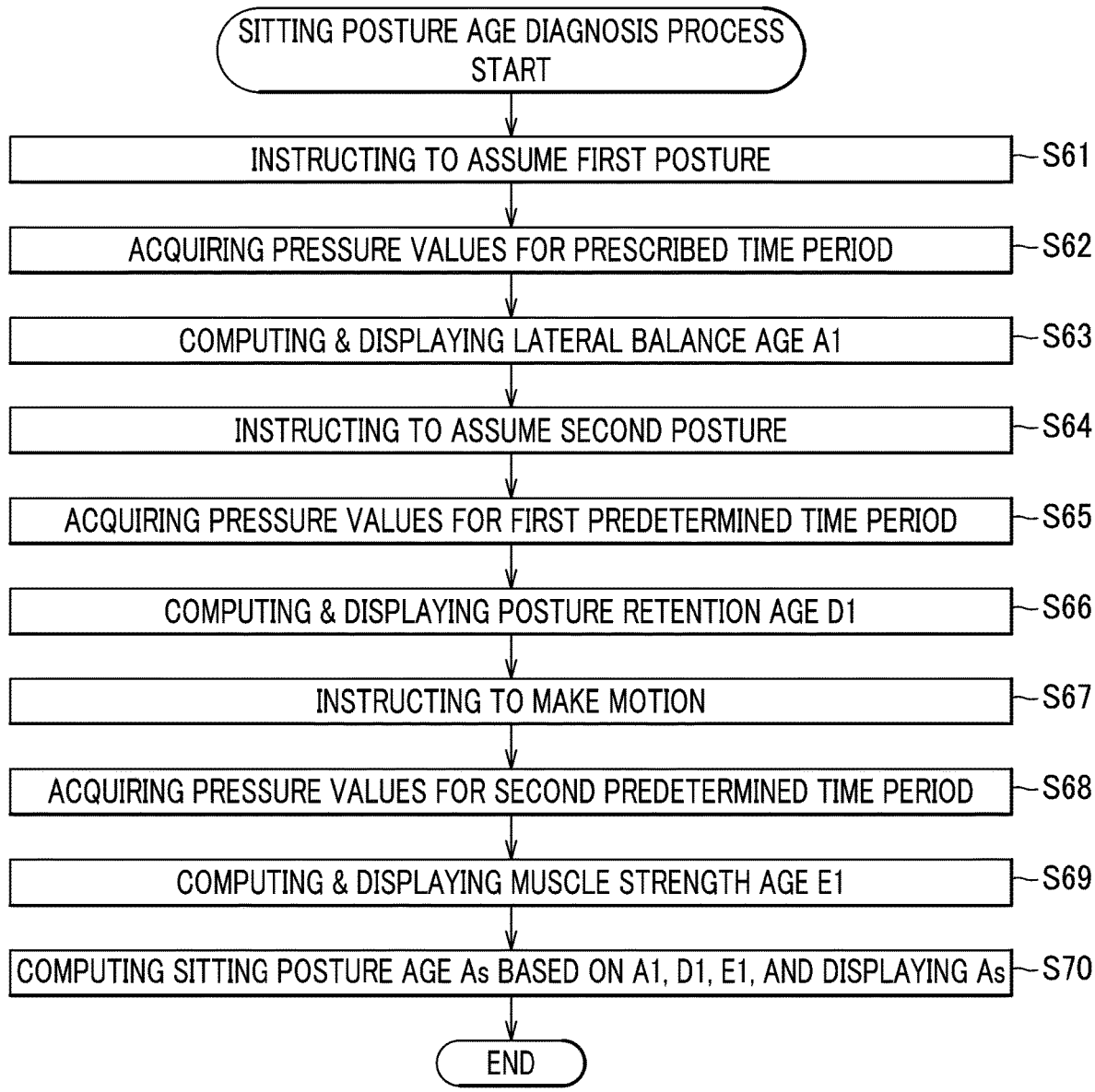
FIG. 32 is a flowchart showing a sitting posture age diagnosis process.

As shown in FIG. 32, in the sitting posture age diagnosis process, the smartphone SP first presents a first instruction screen as shown in FIG. 34(a) on the display DSP to give a user an instruction for prompting the user to have oneself seated in a first posture on the seat S (S61). In the first instruction screen, for example, a message which reads, for example, "Rest your back closely on the seat for the prescribed time" or the like, and/or a picture showing a user seated on the seat S in the first posture, or the like is shown.

The instruction for prompting a user to assume the first posture, given as described above, makes the user sit back in the seat S and relax; thus, a determination of the leftward or rightward deviation of the body of the user can be made accurately. After step S61, the smartphone SP acquires the pressure values from the left and right pressure sensors 21 to 25 corresponding to the lower body, the waist and the back of the user for the prescribed time period, successively for each control cycle (S62). Herein, the prescribed time period may be a relatively short time period, such as five seconds, or the like.

After step S62, the smartphone SP computes the lateral balance age A1 based on the pressure values as acquired, and presents the computed lateral balance age A1 on the display DSP as shown in FIG. 34(b) (S63). To be more specific, the smartphone SP computes the lateral balance age A1 based on the upper-body balance age B1 (as computed based on the pressure values received from the pressure sensors 24, 25) and the lower-body balance age C1 (as computed based on the pressure values received from the pressure sensors 21 to 23).

The smartphone SP makes a determination, in step S63, based on the first evaluation values B2, C2, the upper-body deviation degree B3, and the lower-body deviation degree C3, as described above, as to which side (leftward or rightward) and to what degree the upper-body and the lower-body of the user deviate. Then, the smartphone SP presents the determination results (specifically, evaluation such as good, not so good, or poor) by the type of a cursor CS shown on a gauge GA, and presents the upper-body deviation degree B3 and the lower-body deviation degree C3 by the location of the cursor CS and illustration depicting the locations of the pressure sensors, etc., as illustrated in FIG. 34(b).

Herein, the gauge GA is a gauge with a horizontally extending straight line marked by indices, and a label "Good" indicating that the determination result is good is put on the central index.

The cursor CS is located in such a position that the greater the upper-body leftward or rightward deviation degree, the farther away from the index labeled "Good" the cursor CS is. The type of the cursor changes according to the determination result. For example, if the determination result is good, then the cursor CS is represented by a 'clear weather' mark; if the determination result is not so good, then the cursor CS is represented by a 'cloudy weather' mark; and if the determination result is poor, then the cursor CS is represented by a 'rainy weather' mark (see FIG. 36(b)).

For example, when the smartphone SP has determined that the upper body of the user deviates a little leftward, the smartphone SP shows the 'cloudy weather' mark for the cursor CS corresponding to the upper body of the user, in a position shifted a predetermined distance leftward from the center of the gauge GA. When the smartphone SP has determined that the lower body of the user makes no nonnegligible leftward or rightward postural deviation but deviates slightly rightward, the smartphone SP shows the 'clear weather' mark for the cursor CS corresponding to the lower body of the user, in a position shifted slightly rightward from the center of the gauge GA.

In the illustration depicting the locations of the pressure sensors, a left or right pressure sensor which detects the greater pressure value is shown in an exaggerated manner for each pair of the pressure sensors.

The smartphone SP displays the determination result by a message as well. For example, when the smartphone SP has determined that the upper body of the user deviates a little leftward, the smartphone SP shows a message which reads "Inclined to deviate slightly to the left." The smartphone SP also shows a message about the determination result for the lower body of the user in the same manner.

After step S63, the smartphone SP shows a second instruction screen as shown in FIG. 35(a), on the display DSP to give the user an instruction for prompting the user to have oneself seated in a second posture on the seat S (S64). In the second instruction screen, a message which reads, for example, "Keep your back off the seat for the first predetermined time" or the like, and/or a picture showing a user seated on the seat S in the second posture, or the like is shown.

The instruction for prompting a user to assume the second posture, given as described above, makes the upper body of the user unstable, which makes it difficult for an aged user, or the like to keep his/her posture; thus, a determination as to retention of the posture can be made properly. After step S64, the smartphone SP acquires the pressure values from the left and right pressure sensors 24 corresponding to the waist of the user for the first predetermined time period, successively for each control cycle (S65). Herein, the first predetermined time period may be set at a time period longer than the aforementioned prescribed time period, such as 30 seconds.

After step S65, the smartphone SP computes the posture retention age D1 based on the pressure values as acquired, and presents the computed posture retention age D1 on the display DSP as shown in FIG. 35(b) (S66). The smartphone SP, in step S66, also makes a determination, based on the posture retention degree D3 as described above, as to how good the user has been retaining his/her posture. Then, the smartphone SP notifies the user of the determination result by the gauge GB and the cursor CS, as illustrated in FIG. 35(b).

Herein, the gauge GA is a gauge with a horizontally extending straight line marked by indices, and a label "Good" indicating that the determination result is good is put on the right-end index and a label "Bad" indicating that the determination result is poor is put on the left-end index. A message shown under the cursor CS and the gauge GB is selected in a manner as described above.

After step S66, the smartphone SP shows a third instruction screen as shown in FIG. 36(a), on the display DSP to give the user an instruction for prompting the user to make a predetermined motion (S67). In the third instruction screen, a message which reads, for example, "Move your legs up and down alternately for the second predetermined time period" or the like, and/or a picture showing a user moving his/her legs alternately on the seat S, or the like is shown.

The instruction given as described above makes it possible for a user to readily understand, through the illustrated message, what motion is to be made; thus, a determination as to how much the amount of motion of the user is can be made properly. After step S67, the smartphone SP acquires the pressure values from the left and right pressure sensors 23 corresponding to the thighs of the user for the second predetermined time period, successively for each control cycle (S68). Herein, the second predetermined time period may be set at a time period longer than the aforementioned prescribed time period, such as 30 seconds.

After step S68, the smartphone SP computes the muscle strength age E1 based on the pressure values as acquired, and presents the computed muscle strength age E1 on the display DSP as shown in FIG. 36(b) (S69). The smartphone SP, in step S69, also makes a determination, based on the muscle strength level E3 as described above, as to how much is the amount of motion the user has made. Then, the smartphone SP notifies the user of the determination result by the gauge GB and the cursor CS, as illustrated in FIG. 36(b).

Figure 37:
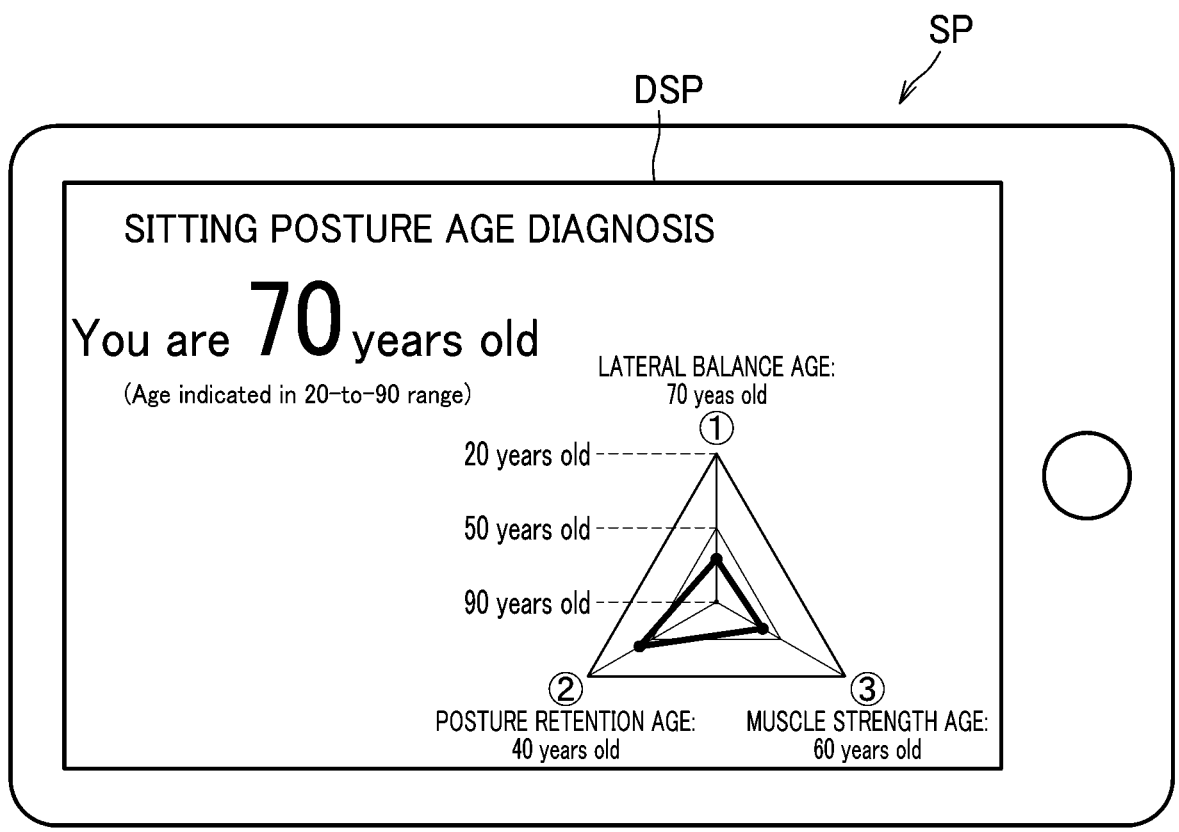
FIG. 37 is a diagram showing a screen for displaying a sitting posture age.

After step S69, the smartphone SP computes a sitting posture age As based on the lateral balance age A1, the posture retention age D1, and the muscle strength age E1, and presents the computed sitting posture age As on the display DSP, as shown in FIG. 37 (S70), and brings this process to an end. It is to be understood that the smartphone SP may show the lateral balance age A1, the posture retention age D1, and the muscle strength age E1, as well, on the screen showing the sitting posture age As. In FIG. 37, the lateral balance age A1, the posture retention age D1, and the muscle strength age E1 are shown in the form of a radar chart, but may be shown in the form of a bar graph, etc., instead.

Next, a detailed description will be given of an example of a specific operation of the seat experiencing system SYS4.

When communication capabilities of the devices (S, SP) which constitute the seat experiencing system SYS4 as shown in FIG. 30 are enabled, and a user operates the smartphone SP to launch the sitting posture age diagnosis, the process proceeds in sequence from step S51 (Yes) to step S52 in the process shown in FIG. 31. Thus, the start screen shown in FIG. 33 is presented on the display DSP. When the user chooses the start button BS, the determination in step S53 turns out to be Yes, and thus the sitting posture age diagnosis process is executed.

Once the sitting posture age diagnosis process is executed, first, the process goes to step S61 shown in FIG. 32, in which the first instruction screen shown in FIG. 34(a) is presented on the display DSP. The user follows the instruction in the first instruction screen, and attempts to keep the first posture of resting his/her back closely on the seat S for the prescribed time period. Thereafter, the smartphone SP acquires pressure values from the left and right pressure sensors 21 to 25 for the prescribed time period, and computes the lateral balance age A1 based on the pressure values (S62 and S63). Specifically, the smartphone SP determines the lateral balance age A1 such that the greater the leftward or rightward postural deviation of the upper body and the lower body of the user, the greater the age is (i.e., the greater value the lateral balance age A1 takes on).

Thereafter, the smartphone SP presents the second instruction screen as shown in FIG. 35(a), on the display DSP (S64). The user follows the instruction in the second instruction screen, and attempts to keep the posture of keeping his/her back off the seat S for the first predetermined time period. Thereafter, the smartphone SP acquires pressure values from the left and right pressure sensors 24 for the first predetermined time period, and computes the posture retention age D1 based on the pressure values (S65 and S66). Specifically, the smartphone SP determines the posture retention age D1 such that the more the user's body sways, the greater the age is (i.e., the greater value the posture retention age D1 takes on).

Thereafter, the smartphone SP presents the third instruction screen as shown in FIG. 36(a), on the display DSP (S67). The user follows the instruction in the third instruction screen, and moves his/her legs up and down alternately for the second predetermined time period. Thereafter, the smartphone SP acquires pressure values from the left and right pressure sensors 23 for the second predetermined time period, and computes muscle strength age E1 based on the pressure values (S68 and S69). Specifically, the smartphone SP determines the muscle strength age E1 such that the greater the amount of motion of the user, the less the age is (i.e., the less value the muscle strength age E1 takes on).

Thereafter, the smartphone SP computes the sitting posture age As based on the lateral balance age A1, the posture retention age D1, and the muscle strength age E1, and displays the sitting posture age As, as shown in FIG. 37 (S70). After displaying the sitting posture age As, the smartphone SP presents the start screen as shown in FIG. 33, on the display DSP.

In the seat experiencing system SYS4 configured according to the present embodiment as described above, the following advantageous effects can be achieved.

The sitting posture age As corresponding to the posture or the motion of the user seated on the seat S can be determined based on the pressure values acquired from the pressure sensors 21 to 25. In particular, according to the present embodiment in which the sitting posture age As is determined based on the first evaluation values B2 and C2, the second evaluation value D2, and the third evaluation value E2, the sitting posture age As can be determined precisely.

Since the evaluation values are computed based on the pressure values acquired from the pressure sensors 21 to 25, the evaluation values can be computed more precisely in comparison with an alternative configuration, for example, in which evaluation values are computed based on information acquired from optical sensors.

The pressure sensors may comprise a left sensor located at a left part of the seat body, and a right sensor located at a right part of the seat body, and the controller may be configured such that the greater a magnitude of a difference between a pressure value from the left sensor and a pressure value from the right sensor, the greater the first evaluation value is made.

Since the greater the magnitude of the difference between the pressure value from the left sensor and the pressure value from the right sensor, the greater the first evaluation values B2 and C2 are made, the sitting posture age As can be determined properly in such a way that the user having an upper or lower body deviated leftward or rightward more is older in age.

Since the greater the range of variation of the pressure value for the first predetermined time period, the greater the second evaluation value D2 is made, the sitting posture age As can be properly determined so that a person who is more difficult to retain his/her posture for the first predetermined time period is older in age.

Since the greater the amount of the motion, the less the third evaluation value E2 is made, the sitting posture age As can be properly determined so that a person who makes a motion of a greater amount is younger in age.

Although the sixth embodiment has been described above, a specific configuration may be modified where appropriate, and implemented as in alternative embodiments which will be described below.

In the above-described embodiment, two first evaluation values corresponding to the upper body and the lower body of a user respectively are used to compute the sitting posture age, but this is not a prerequisite. For example, only the first evaluation value corresponding to the upper body of the user may be used to compute the sitting posture age, or only the first evaluation value corresponding to the lower body of the user may be used to compute the sitting posture age.

In the above-described embodiment, the leftward or rightward postural deviation of the upper body is detected by two pairs of the left sensor and the right sensor corresponding to the waist and the back, but this is not a prerequisite; as long as the left and right sensors are provided in positions at the same distance from upper or lower ends of the backbone extending in the upward-and-downward direction (i.e., at the same height), in pair(s), the number of pairs may be one, or three or more. To be more specific, for example, the leftward or rightward postural deviation of the upper body may be detected by a single pair of the left sensor and the right sensor corresponding to the shoulders.

In the above-described embodiment, the leftward or rightward postural deviation of the lower body is detected by three pairs of the left sensor and the right sensor corresponding to the thighs and the buttocks, but this is not a prerequisite; as long as the left and right sensors are provided in positions at the same distance from front or rear ends of the legs extending in the frontward-and-rearward direction, in pairs, the number of pairs may be one, or any number more than two other than three.

In the above-described embodiment, the sitting posture age As is determined based on the first evaluation values $B2$ and $C2$, the second evaluation value $D2$, and the third evaluation value $E2$, but this is not a prerequisite. For example, the sitting posture age may be determined based on one evaluation value selected among the first evaluation value(s), the second evaluation value, and the third evaluation value, or two evaluation values as selected may be used to determine the sitting posture age.

The smartphone may be configured to provide a screen for allowing a user to enter his/her real age in the sitting posture age diagnosis. In this configuration, for example, the real age and the sitting posture age diagnosis result may be uploaded to the cloud server. With this feature, the sitting posture ages of coeval users can be presented for viewing on the screen of the smartphone. In addition, here, an average of sitting posture ages of the coeval users may be computed to display the average on the screen of the smartphone.

In the above-described embodiment, the smartphone SP is taken as an example of the controller, but this is not a prerequisite; for example, the controller may be implemented in the ECU 100.

In the above-described embodiment, a user is notified of the sitting posture age through presentation on the screen, but this is not a prerequisite; for example, a voice or the like may be used, instead, to notify a user of the sitting posture age.

The seat experiencing system described above may be applied in autonomous driving vehicles. In this application, the seat experiencing system may be configured to be made available on condition that the vehicle is being operated under the autonomous driving mode. Further, when the vehicle switches back from the autonomous driving mode during the use of the seat experiencing system, the use of the seat experiencing system may be restricted before the switching takes place. In that event, a notification may be made through a voice navigation or a display message by activating an advance notice means, so as not to place restrictions unexpectedly, to the effect that restrictions will be placed after a lapse of a predetermined period of time.

The seat experiencing system may alternatively be configured to be made available only when the vehicle is stopped. A determination as to whether or not the vehicle is stopped may be made, based on a determination as to whether or not the vehicle speed is zero, or whether or not the shift lever is in the parking position, or otherwise.

The controller of the seat experiencing system may be configured to acquire information about abnormal events which would occur in the external environment or in the seat experiencing system itself. In this configuration, the seat experiencing system may be configured to place limitations on its service to be offered, upon receipt of information about abnormal event(s). Examples of the abnormal events in the seat experiencing system itself may include an anomaly in a sensor, an anomaly (break) in a harness, an anomaly of the ECU, an anomaly in communication (including an anomaly in the terminal), an anomaly in temperature regulators, such as a heater, fan, or the like, provided in the seat, an anomaly in an actuator for actuating a part or the whole body of the seat, an anomaly in other sensors, such as a seat weight sensor, a temperature sensor, or the like, an anomaly related to the remaining amount of consumables or the usage state, e.g., an aromatic substance for use in the seat is nearing depletion, and an anomaly in the seat controller itself. Examples of the abnormal events in the external environment may include a situation under which execution of apps is undesirable, such as an approach of another vehicle, bad wheeling road condition, a vehicle speed greater than a predetermined value, a strike of an earthquake, destination approaching, the destination having been reached already, it turned out that the game will not come to an end before reaching a destination, the fuel about to run out, the battery about to run down, the temperature or humidity too high in the vehicle or outside, etc.

The limitations may be placed in response to a single occurrence of an abnormal event, or after a plurality of occurrences of the abnormal event. The method of placing limitations may be configured to vary with the level of the abnormality. For example, at the first level, a notification of a recommended option to stop using may be made by a text message, a voice message or the like; at the second level, a notification of a serious proposal to avoid using may be made by a text message, a voice message or the like; and at a third level, the system may be forcefully terminated.

The seat experiencing system may also be configured such that if some of the sensors provided at a specific area are found faulty, the sitting posture diagnosis using the other sensors found not faulty are recommended. For example, if sensors at the seat surface of the seat cushion are found faulty, sitting posture diagnosis using sensors at the side portions provided at the both sides of the seat surface of the seat cushion and bulging up from the seat surface are recommended.

In the above-described embodiment, the pressure sensors 21 to 26 are taken as examples of a sensor, but this is not a prerequisite; for example, the sensor may be an optical sensor, a capacitance sensor, or the like.

The sensors may be provided at left and right side portions (portions bulging from the seat surface) of the seat cushion or the seat back, or at the headrest, the armrests, or parts around the seat (e.g., the instrument panel, the door, the floor, etc.).

In the above-described embodiment, the car seat for use in an automobile is taken as and example of the seat S, but this is not a prerequisite; the seat may be any other type of vehicle seat, such as seats for use in a ship, an aircraft, etc. The seat may not be limited to such a vehicle seat, and may be, for example, a legless chair or the like.

In the above-described embodiment, the smartphone SP is taken as an example of a terminal, but this is not a prerequisite; the terminal may be, for example, a tablet, or any other type of portable terminal other than the smartphone SP. The terminal may be equipped in the seat, and provided integrally with the seat. The terminal may be a terminal which constitutes a car navigation system.

Any of the elements explained in relation to the sixth embodiment and modified examples may be implemented in combination as desired.

Furthermore, any of the elements explained in relation to each of the embodiments and modified examples in this description may be implemented in combination as desired.

The invention claimed is:

1. A seat application management device for managing a usage pattern of a seat provided with a sensor, the seat application management device is configured to execute, in response to an operation of a user:
   an application execution process of providing an interface that allows the user to select at least one application from among a plurality of applications each of which utilizes data acquired from the sensor to offer an experience using the seat to a seated occupant, and executing the selected application; and
   a record presentation process of retrieving and presenting an execution result of an executed application.

2. The seat application management device according to claim 1, wherein the seat application management device is capable of communicating with a server, and
   wherein the record presentation process comprises retrieving, from the server, execution results of applications executed by the user and by another user.

3. The seat application management device according to claim 2, wherein the record presentation process comprises presenting a record of the user and a record of the another user, arranged in a ranking list.

4. The seat application management device according to claim 1, wherein the sensor comprises a plurality of pressure sensors.

5. The seat application management device according to claim 1, wherein the execution result comprises a usage history of the plurality of applications, and
   wherein the record presentation process comprises presenting the usage history of the plurality of applications associated with a specific user.

6. The seat application management device according to claim 1, wherein the application comprises a game using the seat, and
   wherein the execution result comprises a game score.

7. The seat application management device according to claim 1, wherein the execution result comprises at least one of pieces of data selected from: an amount of calories burned, an application execution date, an application execution time, the number of times of execution of the application, an application execution place, and an application title.

8. A seat experiencing system comprising:
   a seat provided with a sensor; and
   a seat application management device for managing a usage pattern of the seat,
   wherein the seat application management device is configured to execute, in response to an operation of a user:
      an application execution process of providing an interface that allows the user to select at least one application from among a plurality of applications each of which utilizes data acquired from the sensor to offer an experience using the seat to a seated occupant, and executing the selected application; and
      a record presentation process of retrieving and presenting an execution result of an executed application.

9. The seat experiencing system according to claim 8, wherein the seat comprises a seat body on which a person is to be seated,
   wherein the sensor comprises a plurality of sensors for detecting a person seated on the seat body, the plurality of sensors including a first sensor and a second sensor located in a position different from a position in which the first sensor is located,
   wherein the seat experiencing system further comprises a seating determination unit configured to make a determination, based on detection results of the sensors, as to whether or not a person has got seated on the seat body, in such a manner that:
   the seating determination unit determines that a person has got seated on the seat body, on condition that the person seated on the seat body has been detected by the first sensor and the person seated on the seat body has been detected by the second sensor, and
   the seating determination unit determines that a person has risen from the seat body, on condition that the person seated on the seat body has become undetected by the first sensor and the person seated on the seat body has become undetected by the second sensor.

10. The seat experiencing system according to claim 9, wherein the first sensor and the second sensor are pressure sensors, and
    wherein the seating determination unit is configured:
       to determine that a person has got seated on the seat body, on condition that a measurement value from the first sensor has become equal to or greater than a first sitting threshold and a measurement value from the second sensor has become equal to or greater than a second sitting threshold, and
       to determine that a person has risen from the seat body, on condition that the measurement value from the first sensor has become equal to or smaller than a first rising threshold smaller than the first sitting threshold and the measurement value from the second sensor has become equal to or smaller than a second rising threshold smaller than the second sitting threshold.

11. The seat experiencing system according to claim 10, wherein the seat body comprises a seat bottom on which a person is to be seated, and
    wherein the first sensor is located in a position corresponding to buttocks of a person to be seated on the seat bottom, and the second sensor is located in a position corresponding to thighs of a person to be seated on the seat bottom.

12. The seat experiencing system according to claim 11, wherein the first sensor comprises at least one right first sensor and at least one left first sensor, and
    wherein the second sensor comprises at least one right second sensor and at least one left second sensor.

13. The seat experiencing system according to claim 9, further comprising a time-measuring unit configured to measure time based on a result of the determination made by the seating determination unit, wherein the time-measuring unit starts measurement of time at a time when the seating determination unit has determined that a person has risen from the seat body, ends the measurement of time at a time when the seating determination unit has determined that a person has got seated on the seat body, and determines by calculation an elapsed time that has elapsed from the time of starting the measurement of time to the time of ending the measurement of time.

14. The seat experiencing system according to claim 9, further comprising a time-measuring unit configured to measure time based on a result of the determination made by the seating determination unit, wherein the time-measuring unit starts measurement of time at a time when the seating determination unit has determined that a person has got seated on the seat body, and executes a predetermined operation for prompting the person seated on the seat body to rise from the seat body after a lapse of a predetermined time period from the time of starting the measurement of time, and stops the predetermined operation at a time when the seating determination unit has determined that the person has risen from the seat body.

15. The seat experiencing system according to claim 14, wherein the predetermined operation comprises an operation of producing a predetermined sound, which includes playing music.

16. The seat experiencing system according to claim 9, further comprising a time-measuring unit configured to measure time based on a result of the determination made by the seating determination unit, wherein the time-measuring unit starts measurement of time at a time when the seating determination unit has determined that a person has got seated on the seat body, ends the measurement of time at a time when the seating determination unit has determined that a person has risen from the seat body, and determines by calculation an elapsed time that has elapsed from the time of starting the measurement of time to the time of ending the measurement of time.

17. The seat experiencing system according to claim 9, wherein the seating determination unit determines that a person has risen from the seat body when a first time period has elapsed from a time at which the person seated on the seat body has become undetected by the first sensor and the person seated on the seat body has become undetected by the second sensor.

18. The seat experiencing system according to claim 9, wherein the seating determination unit determines that a person has got seated on the seat body when a second time period has elapsed from a time at which the person seated on the seat body has been detected by the first sensor and the person seated on the seat body has been detected by the second sensor.

19. A seat application management program product comprising at least one non-transitory computer-readable storage medium having one or more program instructions stored therein for managing a usage pattern of a seat provided with a sensor, the program instructions being configured to cause a computer to execute, in response to an operation of a user:

an application execution process of providing an interface that allows the user to select at least one application from among a plurality of applications each of which utilizes data acquired from the sensor to offer an experience using the seat to a seated occupant, and executing the selected application; and a record presentation process of retrieving and presenting an execution result of an executed application.

\* \* \* \* \*